United States Patent
Freimer et al.

(10) Patent No.: US 6,750,010 B1
(45) Date of Patent: Jun. 15, 2004

(54) METHODS FOR TREATING BIPOLAR MOOD DISORDER ASSOCIATED WITH MARKERS ON CHROMOSOME 18P

(75) Inventors: Nelson B. Freimer, San Francisco, CA (US); Lodewijk Sandkuijl, Delft (NL); Pedro Leon, San Jose (CR); Victor I. Reus, San Francisco, CA (US); Michael Escamilla, San Francisco, CA (US); Lynne Allison McInnes, San Francisco, CA (US); Susan K. Service, Watsonville, CA (US)

(73) Assignees: The Regents of the University of California, Oakland, CA (US); Univerisity of Costa Rica, San Jose (CR)

( * ) Notice: Subject to any disclaimer, the term of this patent is extended or adjusted under 35 U.S.C. 154(b) by 0 days.

(21) Appl. No.: 08/976,560

(22) Filed: Nov. 24, 1997

Related U.S. Application Data

(63) Continuation of application No. 08/916,683, filed on Aug. 22, 1997, now abandoned.
(60) Provisional application No. 60/023,438, filed on Aug. 23, 1996.

(51) Int. Cl.$^7$ ............................ C12Q 1/68; C12P 19/34; C07H 21/02; C07H 21/04
(52) U.S. Cl. ...................... 435/6; 435/91.2; 536/23.1; 536/23.5; 536/24.2; 536/24.31
(58) Field of Search .............................. 536/23.1, 23.5, 536/24.2, 24.31; 435/6, 91.2

(56) References Cited

U.S. PATENT DOCUMENTS 5,283,185 A    2/1994   Epand et al. ............ 435/172.3

OTHER PUBLICATIONS

Nothen et al. Molecular Psychiatry (1999) 4: 76–84.*
Gershon et al. Neuro Psychopharmacology (1998) 18(4) 233–242.*
Ewald et al. Psychiatric Genetics (1997) 7:1–12.*
Esterling et al. Molecular Psychiatry (1997) 2:501–504.*
McInnes et al. PNAS (1996) 93(23): 13060–13065.*
Overhauser, J. et al. "Report of the Third International Workshop on Human Chromosome 18 mapping 1995", Cytogenetics and Cell Genetics, vol. 71, No. 2, 1995, pp. 106–119.
Ballabio et al., "*The rise and fall of positional cloning?*" Nat Genet., vol. 3, pp. 277–279. (1993).
Baron et al., "*Diminished support for linkage between manic depressive illness and X–chromosome markers in three Israeli pedigrees,*" Nature, vol. 3, pp. 49–55 (1993).
Baron et al., "Genetic linkage between X–chromosome markers and bipolar affective illness," Nature, vol. 326, pp. 289–292 (1987).
Berrettini et al., "*Chromosome 18 DNA markers and manic–depressive illness: Evidence for a susceptibility gene,*" Proc. Nat'l Acad, Sci., vol. 91, pp. 5918–5921, U.S.A. (1994).
Bertelson et al., "A Danish Twin Study of Manic–Depressive Disorders," Br. J. Psychiatry. vol. 130, pp. 330–351 (1977).
Boehnke, M., "*Allele Frequency Estimation from Data on Relatives,*" Am. J. Hum. Genet., vol. 48, pp. 22–25 (1991).
Browne and Litt, "*Characterization of (CA)n microsatellites with degenerate sequencing primers,*" Nucleic Acids Res., vol. 20, p. 141 (1992).
Buckler et al., "*Exon amplificaton: a strategy to isolate mammalian genes based on RNA splicing,*" Proc Natl Acad Sci, vol. 88, pp. 4005–4009, U.S.A. (1991).
Cohen et al., "*A first–generation physical map of the human genome,*" Nature, vol. 366, pp. 698–701 (1993).
Coon, Hilary et al., "Analysis of Chromosome 18 DNA Markers in Multiplex Pedigrees with Manic Depression," Biol Psychiatry, vol. 39, pp. 689–696 (1996).
Copeman, J.B. et al., "*Linkage disequilibrium mapping of a type 1 diabetes susceptibility gene (IDDM7) to chromosome 2q31–q33,*" Nature Genet., vol. 9, pp. 80–85 (1995).
Cotton et al., "*Reactivity of cytosine and thymine in single–base–pair mismatches with hydroxylamine and osmium tetroxide and its application to the study of mutations,*" Proc Natl Acad Sc, vol. 85, pp. 4397–4401, U.S.A. (1988).
De La Chapelle, "*Disease gene mapping in isolated human populations: the example of Finland,*" J Med Genet., vol. 30, pp. 857–865 (1993).
Delisi, Lynn E., "*Failure to Find a Chromosome 18 Pericentric Linkage in Families With Schizophrenia,*" Am J. of Med. Genetics, vol. 60, pp. 532–534 (1995).
Dirienzo, A. et al., "*Mutational processes of simple–sequence repeat loci in human population,*" Proc. Nat'l Acad. Sci., vol. 91, pp. 3166–3170, U.S.A. (1994).

(List continued on next page.)

*Primary Examiner*—Carla Myers
(74) *Attorney, Agent, or Firm*—Carol L. Francis; Paula A. Borden; Bozicevic, Field & Francis, LLP

(57) ABSTRACT

The present invention is directed to methods of detecting the presence of a bipolar mood disorder susceptibility locus in an individual, comprising analyzing a sample of DNA for the presence of a DNA polymorphism on the short arm of chromosome 18 between the telomere and D18S481, wherein the DNA polymorphism is associated with a form of bipolar mood disorder. The invention for the first time provides strong evidence of a susceptibility gene for bipolar mood disorder that is located in the terminal 5 cM region of the short arm of chromosome 18. The disclosure describes the use of linkage analysis and genetic markers in this 5 cM region to fine map the region and the use of genetic markers to genetically diagnose (genotype) bipolar mood disorder in individuals, to confirm phenotypic diagnoses of bipolar mood disorder, to determine appropriate treatments for patients with particular genotypic subtypes. Isolated polynucleotides useful for genetic linkage analysis of BP-I and methods for obtaining such isolated polynucleotides are also described.

11 Claims, 57 Drawing Sheets

OTHER PUBLICATIONS

Edwards, J.H., "The analysis of X-linkage," Ann, Hum. Genet., vol. 34, pp. 229–250 (1971).

Endicott, J. et al., "A Diagnostic Interview," Arch. Gen. Psych., vol. 35, pp. 837–844 (1978).

Egeland et al., "Bipolar affective disorders linked to DNA markers on chromosome 11," Nature, vol. 325, pp. 783–787 (1987).

Escamilla, M.A. et al., "Use of Linkage Disequilibrium Approaches to Map Genes for Bipolar Disorder in the Costa Rican Population," Neuropsychiat. Genet., vol. 67, pp. 244–253 (1996).

Felgner et al., "Lipofection: A Highly Efficient, Lipid–Mediated DNA–Transfection Procedures," Proc. Nat'l Acad. Sci., vol. 84:7413–7417, U.S.A. (1987).

Freimer, N.B. et al., "An Approach to Investigating Linkage for Bipolar Disorder Using Large Costa Rican Pedigrees," Neuropsychiat. Genet, vol. 67, pp. 254–263 (1996).

Freimer, N.B. et al., "Genetic Mapping using haplotype, association and linkage methods suggests a locus for severe bipolar disorder (BPI) at 18q22–q23," Nature Genetics, vol. 12, pp. 436–441 (1996).

Freimer and Reus, "The Genetics of Bipolar Disorder and Schizophrenia," Ch:64, pp. 951–965 (1992).

Goodwin, F.K. et al., "Manic Depressive Illness," Oxford University Press, pp. 373–401, New York (1990).

Gyapay, F. et al., "The 1993094 Généthon human genetic linkage map," Nature Genet., vol. 7, pp. 246–339 (1994).

Hästbacka et al., "The Diastrophic Dysplasia Gene Encodes a Novel Sulfate Transporter: Positional Cloning by Fine–Structure Linkage Disequilibrium Mapping," Cell, vol. 78, pp. 1073–1087 (1994).

Houwen et al., "Genome screening by searching for shared segments: mapping a gene for benign recurrent intrahepatic cholestasis," Nat Genet., vol. 8, pp. 380–386 (1994).

Hudson et al., "Isolation and Chromosomal Assignment of 100 Highly Informative Human Simple Sequence Repeat Polymorphisms," Genomics, vol. 13, pp. 622–629 (1992).

Hummerich et al., "Distribution of trinucleotide repeat sequences across a 2 Mbp region containing the Huntington's disease gene," Hum Mol Genet, vol. 3, pp. 73–8 (1994).

Jou, et al., "Localization of the $\alpha_2$ –Macroglobulin Receptor–Associated Protein 1 Gene (LRPAP1) and Other Gene Fragments to Human Chromosome 4p16.3 by Direct cDNA–Selection," Genomics, vol. 24, pp. 410–413 (1994).

Kelsoe et al., "Re–evaluation of the linkage relationship between chromosome 11p loci and the gene for bipolar affective disorder in the Old Order Amish," Nature, vol. 342, pp. 238–243 (1989).

Kerem et al., "Identification of the Cystic Fibrosis Gene: Genetic Analysis," Science, vol. 245, pp. 1073–1080 (1989).

Lander, E.S. et al., "Mapping Complex Genetic Traits in Humans: New Methods Using a Complete RFLP Linkage Map,"Cold Springs Harber, vol. 51, pp. 49–62 (1986).

Lathrop et al., "Strategies for multilocus linkage analysis in humans," Proc. Nat'l Acad. Sci., vol. 81, pp. 3443–3446, U.S.A. (1984).

Leon et al., "The gene for an inherited form of deafness maps to chromosome 5q31," Proc. Nat'l Acad. Sci., vol. 89:5181–5184, U.S.A. (1992).

Lovett, M. et al., "Direct selection: A method for the isolation of cDNAs encoded by large genomic regions," Proc. Nat'l Acad. Sci., vol. 88, pp. 9628–9632, U.S.A. (1991).

MacDonald et al., "The Huntington's disease candidate region exhibits many different haplotypes," Nat Genet., vol. 1, pp. 99–103. (1992).

Maier et al., "Linkage analysis between pericentrometric markers on chromosome 18 and bipolar disorder: A replication test," Psych. Res., vol. 59, pp. 7–15 (1995).

McInnis, L.A. et al., "Mapping genes for psychiatric disorders and behavioral traits," Curr. Opin, in Genet. And Development, vol. 5, pp. 376–381 (1995).

Muller et al., "Laboratory Methods—Efficient Transfection and Expression of Heterologous Genes in PC12 Cells," DNA and Cell Biol., vol. 9, pp. 221–229 (1990).

Murray, J.C. et al., "A Comprehensive Human Linkage Map with Centimorgan Density," Science, vol. 265, pp. 2049–2054 (1994).

Nurnberger, J.L. et al., "Diagnostic Interview for Genetic Studies," Arch. Gen, Psychiat, vol. 51, pp. 849–859 (1994).

Nylander et al., "Anticipation in Swedish families with bipolar affective disorder," J Med Genet., vol. 31, pp. 686–689 (1994).

Pauls et al., "Linkage Analyses of Chromosome 18 Markers Do Not Identify a Major Susceptibility Locus for Bipolar Affective Disorders in the Old Order Amish," Am. J. Hum. Genet., vol. 57, pp. 636–643 (1995).

Pauls et al., "Risks of affective illness among first–degree relatives of bipolar I old–order Amish probands," Arch Gen Psychiatry, vol. 49, pp. 703–708 (1992).

Petrukhin, K.E. et al., "A Microsatellite Genetic Linkage Map of Human Chromosome 13," Genomics, vol. 15, pp. 76–85 (1993).

Spielman et al., "Transmission Test for Linkage Disequilibrium: The Insulin Gene Region and Insulin–dependent Diabetes Mellitus (IDDM)," Am. J. Hum. Genet., vol. 52. p. 506 (1993).

Stine et al., "Evidence for Linkage of Bipolar Disorder to Chromosome 18 with a Parent–of–Origin Effect," Am J Hum Genet., vol. 57, pp. 1384–1394 (1995).

Straub et al., "A possible vulnerability locus for bipolar affective disorder on chromosome 21q22.3," Nature Genet., vol. 8, pp. 291–296 (Nov. 1994).

Terwilliger, Am. J. Hum. Genet., "A Powerful Likelihood Method for the Analysis of Linkage Disequilibrium between Trait Loci and One or More Polymorphic Marker Loci," vol. 56, p. 777 (1995).

Uhrhammer, N. et al., "Sublocalization of an Ataxia–Telangiectasia Gene Distal to D11S384 by Ancestral Haplotyping in Costa Rican Families," Am. J. Hum. Genet., vol. 57, pp. 103–111 (1992).

Weber, J.L., "Informativeness of Human $(dC-dA)_n$ $(dG-dT)_n$ Polymorphisms," Genomics, vol. 7, pp. 524–530 (1990).

Weissenbach et al., "A second–generation linkage map of the human genome," Nature, vol. 359, pp. 794–801 (1992).

Yoshikawa et al., "Isolation of Chromosome 18–Specific Brain Transcripts as Positional Candidates for Bipolar Disorder," Am. J. Hum. Genet. vol. 74, pp. 140–149 (1997).

* cited by examiner

| Marker Name | distance from pter | Family CR001 | | Family CR004 | | Combined | |
|---|---|---|---|---|---|---|---|
| | | $Z_{max} \geq 0.8$ | Theta | $Z_{max} \geq 1.2$ | Theta | $Z_{max} \geq 1.6$ | Theta |
| D1S456 | 224.6 | 1.32 | 0.0 | 0.0 | 0.50 | 0.0 | 0.50 |
| D2S130 | 230.1 | 0.89 | 0.0 | 0.12 | 0.35 | 0.36 | 0.26 |
| D3S1285 | 91.0 | 0.00 | 0.50 | 2.59 | 0.00 | 1.15 | 0.16 |
| D4S171 | 207.9 | 1.07 | 0.07 | 0.01 | 0.05 | 0.22 | 0.29 |
| D5S427 | 69.6 | 1.39 | 0.0 | 0.0 | 0.50 | 0.7 | 0.18 |
| D7S510 | 60.5 | 0.04 | 0.40 | 2.04 | 0.0 | 0.82 | 0.17 |
| D11S929 | 36.3 | 0.80 | 0.11 | 0.03 | 0.42 | 0.43 | 0.24 |
| D11S1392 | 38.6 | 0.86 | 0.07 | 0.90 | 0.23 | 1.58 | 0.19 |
| D11S1312 | 42.0 | 0.47 | 0.13 | 1.77 | 0.0 | 1.95 | 0.05 |
| D13S175 | 7.4 | 0.83 | 0.0 | 0.0 | 0.50 | 0.24 | 0.15 |
| D15S126 | 45.5 | 1.09 | 0.0 | 0.0 | 0.48 | 0.06 | 0.40 |
| D16S521 | 4.6 | 1.46 | 0.0 | 0.41 | 0.26 | 1.18 | 0.17 |
| D16S515 | 94.8 | 0.93 | 0.09 | 0.01 | 0.46 | 0.39 | 0.25 |
| D16S486 | 133.6 | 0.27 | 0.19 | 1.29 | 0.20 | 1.60 | 0.20 |
| D17S849 | 0.60 | 0.0 | 0.50 | 1.22 | 0.07 | 0.32 | 0.14 |
| D18S59 | 1.1 | 1.43 | 0.0 | 0.0 | 0.50 | 0.02 | 0.46 |
| D18S1105 | 2.8 | 0.97 | 0.0 | 0.01 | 0.47 | 0.01 | 0.46 |
| D18S71 | 43.8 | 0.96 | 0.0 | 0.0 | 0.50 | 0.0 | 0.50 |
| D18S64 | 84.0 | 0.33 | 0.11 | 1.34 | 0.15 | 1.67 | 0.13 |
| D18S55 | 95.5 | 0.0 | 0.50 | 2.09 | 0.13 | 1.51 | 0.18 |
| D18S61 | 103.8 | 0.0 | 0.50 | 2.26 | 0.12 | 1.94 | 0.16 |
| D18S488 | 105.6 | 0.0 | 0.50 | 1.26 | 0.14 | 1.02 | 0.19 |
| D18S1161 | 113.0 | 0.0 | 0.50 | 1.79 | 0.16 | 1.76 | 0.17 |

FIG. 2

|   | STS | Chrom | Map Position | | Contig | |
|---|---|---|---|---|---|---|
|   |   |   | Genetic | RH | Single | Double |
| 1 | WI-9527 | Chr18 | - | - | WC18.0 | WC-1465 |
| 2 | CHLC.GGAT2G04 | Chr18 | - | - | WC18.0 | WC-1465 |
| 3 | CHLC.GGAT2G04.1217 | Chr18 | - | - | WC18.0 | WC-1465 |
| 4 | D18S59 | Chr18 | 0 cM | - | WC18.0 | WC-1465 |
| 5 | D18S1140 | Chr18 | 0 cM | - | WC18.0 | WC-1465 |
| 6 | WI-7796 | Chr18 | - | 15 cR | WC18.0 | - |
| 7 | WI-9074 | Chr18 | - | 12 cR | WC18.0 | WC-1465 |
| 8 | WI-5528 | Chr18 | - | 7 cR | WC18.0 | - |
| 9 | D18S476 | Chr18 | 1 cM | 0 cR | WC18.0 | - |
| 10 | WI-7226 | Chr18 | - | - | WC18.0 | WC-909 |
| 11 | AFMB324ZE5 | Chr18 | - | - | WC18.0 | WC-909 |
| 12 | AFMB082ZF1 | Chr18 | - | 5 cR | WC18.0 | WC-909 |
| 13 | D18S1146 | Chr18 | 1 cM | - | WC18.0 | WC-909 |
| 14 | WI-3058 | Chr18 | - | 5 cR | WC18.0 | WC-909 |
| 15 | D18S1105 | Chr18 | 1 cM | - | WC18.0 | WC-909 |
| 16 | WI-3730 | Chr18 | - | 5 cR | WC18.0 | WC-1576 |
| 17 | AFM077YD11 | Chr18 | - | - | WC18.0 | WC-1576 |
| 18 | D18S1098 | Chr18 | 4 cM | - | WC18.0 | WC-1576 |
| 19 | WI-7469 | Chr18 | - | 16 cR | WC18.0 | WC-1576 |
| 20 | WI-7871 | Chr18 | - | 22 cR | WC18.0 | WC-1576 |
| 21 | D18S481 | Chr18 | 5 cM | 21 cR | WC18.0 | WC-1576 |
| 22 | WI-4747 | Chr18 | - | - | WC18.0 | WC-1576 |
| 23 | D18S1154 | Chr18 | 6 cM | - | WC18.0 | WC-1576 |
| 24 | CHLC.ATA14B09 | Chr18 | - | - | WC18.0 | WC-1576 |
| 25 | WI-7466 | Chr18 | - | 27 cR | WC18.0 | WC-1576 |
| 26 | D18S54 | Chr18 | 6 cM | 25 cR | WC18.0 | WC-1576 |
| 27 | D18S63 | Chr18 | 6 cM | - | WC18.0 | WC-1576 |
| 28 | D18S459 | Chr18 | 6 cM | 25 cR | WC18.0 | WC-1576 |
| 29 | WI-6014 | Chr18 | - | - | WC18.0 | WC-1576 |
| 30 | WI-4219 | Chr18 | - | 28 cR | WC18.0 | WC-143 |
| 31 | AFM238YG3 | Chr18 | - | - | WC18.0 | WC-143 |
| 32 | D18S471 | Chr18 | 17 cM | 28 cR | WC18.0 | WC-143 |
| 33 | D18S458 | Chr18 | 17 cM | - | WC18.0 | WC-143 |

*FIG. 6A*

| | | | | | | |
|---|---|---|---|---|---|---|
| 34 | D18S452 | Chr18 | 17 cM | - | WC18.0 | WC-143 |
| 35 | D18S62 | Chr18 | 17 cM | - | WC18.0 | WC-143 |
| 36 | WI-5627 | Chr18 | - | 28 cR | WC18.0 | WC-143 |
| 37 | CHLC.GATA82D03 | Chr18 | - | 28 cR | WC18.0 | WC-143 |
| 38 | FB25F12 | Chr18 | - | - | WC18.0 | WC-143 |
| 39 | CHLC.GATA51H07 | Chr18 | - | - | WC18.0 | WC-143 |
| 40 | CHLC.GATA88A12 | Chr18 | - | 30 cR | WC18.0 | WC-143 |
| 41 | WI-9619 | Chr18 | - | - | WC18.0 | WC-143 |
| 42 | AFMB346YA9 | Chr18 | - | - | WC18.0 | WC-143 |
| 43 | AFM323TC9 | Chr18 | - | - | WC18.0 | WC-862 |
| 44 | WI-5607 | Chr18 | - | 36 cR | WC18.0 | WC-862 |
| 45 | WI-9017 | Chr18 | - | 36 cR | WC18.0 | WC-862 |
| 46 | AFM077YF7 | Chr18 | - | - | WC18.0 | WC-934 |
| 47 | WI-8546 | Chr18 | - | - | WC18.0 | WC-934 |
| 48 | CHLC.GGAA16G02 | Chr18 | - | - | WC18.0 | WC-934 |
| 49 | D18S464 | Chr18 | 32 cM | 46 cR | WC18.0 | WC-934 |
| 50 | NIB1802 | Chr18 | - | 56 cR | WC18.0 | WC-934 |
| 51 | D18S1153 | Chr18 | 34 cM | - | WC18.0 | WC-934 |
| 52 | D18S1150 | Chr18 | 36 cM | - | WC18.0 | WC-934 |
| 53 | WI-4589 | Chr18 | - | 58 cR | WC18.0 | WC-934 |
| 54 | WI-4319 | Chr18 | - | 62 cR | WC18.0 | WC-934 |
| 55 | D18S1158 | Chr18 | 38 cM | - | WC18.0 | WC-934 |
| 56 | D18S1116 | Chr18 | 40 cM | - | WC18.0 | WC-377 |
| 57 | CHLC.GATA11A06.668 | Chr18 | - | 48 cR | WC18.0 | WC-377 |
| 58 | CHLC.GATA11A06 | Chr18 | - | 54 cR | WC18.0 | WC-377 |
| 59 | D18S53 | Chr18 | 41 cM | - | WC18.0 | WC-377 |
| 60 | WI-9134 | Chr18 | - | 52 cR | WC18.0 | WC-377 |
| 61 | IB1114 | Chr18 | - | - | WC18.0 | WC-377 |
| 62 | D18S482 | Chr18 | 41 cM | 56 cR | WC18.0 | WC-377 |
| 63 | WI-2382 | Chr18 | - | - | WC18.0 | WC-377 |
| 64 | WI-6819 | Chr18 | - | - | WC18.0 | WC-377 |
| 65 | D18S71 | Chr18 | 43 cM | 84 cR | WC18.0 | WC-377 |
| 66 | AFMA058YG5 | Chr18 | - | 80 cR | WC18.0 | WC-377 |
| 67 | WI-5506 | Chr18 | - | 90 cR | WC18.0 | WC-377 |
| 68 | D18S453 | Chr18 | 43 cM | 93 cR | WC18.0 | WC-738 |
| 69 | D18S73 | Chr18 | 43 cM | - | WC18.0 | WC-377 |
| 70 | STSG-10174 | Chr18 | - | - | WC18.0 | WC-377 |

*FIG. 6B*

| 71 | CHLC.CCT5D07 | Chr18 | –      | 101 cR | WC18.0 | WC-377  |
| 72 | W-10768      | Chr18 | –      | –      | WC18.0 | WC-1182 |
| 73 | D18S1149     | Chr18 | 49 cM  | –      | WC18.0 | WC-1182 |
| 74 | W-1869       | Chr18 | –      | –      | WC18.0 | WC-1182 |
| 75 | D18S1104     | Chr18 | 49 cM  | –      | WC18.0 | WC-1182 |
| 76 | AFMA205YH5   | Chr18 | –      | –      | WC18.0 | WC-1182 |
| 77 | AFMB340VE5   | Chr18 | –      | –      | WC18.0 | WC-1182 |
| 78 | CHLC.GATA41G05 | Chr18 | –    | 185 cR | WC18.0 | WC-1182 |
| 79 | AFMB319WF9   | Chr18 | –      | –      | WC18.0 | WC-1182 |
| 80 | D18S44       | Chr18 | –      | –      | WC18.0 | WC-1182 |

Details on contig assembly.

*FIG. 6C*

18p allele frequencies

| MARKERNAME | | aff 105 | ntrans | control | | |
|---|---|---|---|---|---|---|
| D18SAVA5 | 225 | 0.04 | 0.02 | | | |
| | 227 | 0.29 | 0.24 | | | |
| | 229 | 0.22 | 0.15 | | | |
| | 231 | 0.04 | 0.08 | | | |
| | 233 | 0.14 | 0.23 | | | |
| | 235 | 0.25 | 0.22 | | | |
| | 237 | 0.02 | 0.03 | | | |
| | 239 | 0.00 | 0.00 | | | |
| | | | | | | |
| D18SCA211 | 183 | 0.02 | 0.04 | 0.01 | | |
| | 189 | 0.00 | 0.01 | 0.01 | | |
| | 191 | 0.01 | 0.00 | 0.03 | | |
| | 193 | 0.24 | 0.17 | 0.33 | | |
| | 195 | 0.21 | 0.19 | 0.18 | | |
| | 197 | 0.06 | 0.11 | 0.03 | | |
| | 199 | 0.06 | 0.04 | 0.01 | | |
| | 201 | 0.10 | 0.14 | 0.10 | | |
| | 203 | 0.02 | 0.04 | 0.06 | | |
| | 205 | 0.16 | 0.18 | 0.14 | | |
| | 207 | 0.09 | 0.04 | 0.06 | | |
| | 209 | 0.02 | 0.02 | 0.02 | | |
| | 211 | 0.01 | 0.00 | 0.00 | | |
| | 215 | 0.00 | 0.00 | 0.00 | | |
| | 217 | 0.00 | 0.00 | 0.01 | | |
| D18SCA212 | 200 | 0.40 | 0.40 | 0.39 | | |
| | 202 | 0.31 | 0.32 | 0.29 | | |
| | 204 | 0.05 | 0.05 | 0.03 | | |
| | 206 | 0.04 | 0.06 | 0.10 | | |
| | 214 | 0.01 | 0.00 | 0.00 | | |
| | 216 | 0.14 | 0.12 | 0.15 | | |

*FIG. 7A*

18p allele frequencies

| MARKERNAME | | off 105 | ntrans | control | | |
|---|---|---|---|---|---|---|
| | 218 | 0.04 | 0.00 | 0.04 | | |
| | | | | | | |
| | | | | | | |
| D18S1140 | 256 | 0.06 | 0.07 | 0.06 | | |
| | 268 | 0.77 | 0.72 | 0.73 | | |
| | 270 | 0.02 | 0.00 | 0.06 | | |
| | 272 | 0.03 | 0.03 | 0.03 | | |
| | 274 | 0.00 | 0.00 | 0.00 | | |
| | 276 | 0.03 | 0.06 | 0.02 | | |
| | 278 | 0.02 | 0.06 | 0.05 | | |
| | 280 | 0.04 | 0.06 | 0.02 | | |
| | 282 | 0.01 | 0.00 | 0.02 | | |
| | | | | | | |
| | | | | | | |
| | | | | | | |
| MARKERNAME | | off 105 | ntrans | control | | |
| | | | | | | |
| D18S59 | 148 | 0.16 | 0.26 | 0.21 | | |
| | 150 | 0.07 | 0.09 | 0.14 | | |
| | 152 | 0.02 | 0.06 | 0.01 | | |
| | 154 | 0.36 | 0.19 | 0.28 | 0.17 | 0.08 |
| | 156 | 0.04 | 0.04 | 0.08 | | |
| | 158 | 0.22 | 0.21 | 0.13 | | |
| | 160 | 0.04 | 0.08 | 0.05 | | |
| | 162 | 0.05 | 0.06 | 0.05 | | |
| | 164 | 0.02 | 0.01 | 0.02 | | |
| | 168 | 0.00 | 0.00 | 0.01 | | |
| | | | | | | |
| D18STA201 | 214 | 0.02 | 0.00 | 0.00 | | |
| | 220 | 0.09 | 0.09 | 0.04 | | |
| | 222 | 0.01 | 0.00 | 0.01 | | |
| | 228 | 0.01 | 0.01 | 0.00 | | |
| | 230 | 0.25 | 0.22 | 0.16 | 0.03 | 0.09 |

*FIG. 7B*

18p allele frequencies

| MARKERNAME | | off 105 | ntrans | control | | |
|---|---|---|---|---|---|---|
| | 232 | 0.07 | 0.04 | 0.07 | | |
| | 234 | 0.02 | 0.00 | 0.00 | | |
| | 236 | 0.01 | 0.00 | 0.00 | | |
| | 238 | 0.01 | 0.00 | 0.00 | | |
| | 242 | 0.09 | 0.09 | 0.04 | | |
| | 244 | 0.13 | 0.13 | 0.19 | | |
| | 246 | 0.09 | 0.09 | 0.11 | | |
| | 248 | 0.06 | 0.11 | 0.10 | | |
| | 250 | 0.07 | 0.07 | 0.06 | | |
| | 252 | 0.07 | 0.10 | 0.12 | | |
| | 254 | 0.02 | 0.03 | 0.03 | | |
| | 256 | 0.01 | 0.01 | 0.03 | | |
| | 258 | 0.01 | 0.01 | 0.01 | | |
| | 260 | 0.01 | 0.09 | 0.02 | | |
| | 262 | 0.01 | 0.00 | 0.00 | | |
| | | | | | | |
| D18SCA231 | 182 | 0.00 | 0.00 | 0 | | |
| | 184 | 0.20 | 0.23 | 0.26 | | |
| | 186 | 0.70 | 0.66 | 0.68 | | |
| | 188 | 0.00 | 0.01 | 0.01 | | |
| | 190 | 0.02 | 0.00 | 0.02 | | |
| | 192 | 0.00 | 0.00 | 0.01 | | |
| | 194 | 0.02 | 0.02 | 0 | | |
| | 196 | 0.00 | 0.00 | 0 | | |
| | 198 | 0.02 | 0.01 | 0 | | |
| | 200 | 0.01 | 0.01 | 0.01 | | |
| | 202 | 0.02 | 0.03 | 0.01 | | |
| | | | | | | |
| | | | | | | |
| | | | | | | |
| | | | | | | |
| MARKERNAME | | off 105 | ntrans | control | | |

FIG. 7C 18p allele frequencies

| MARKERNAME | | aff 105 | ntrans | control | | |
|---|---|---|---|---|---|---|
| D18SAT201 | 170 | 0.53 | 0.55 | 0.52 | | |
| | 174 | 0.00 | 0.01 | 0.01 | | |
| | 178 | 0.37 | 0.36 | 0.36 | | |
| | 182 | 0.01 | 0.00 | 0.00 | | |
| | 186 | 0.07 | 0.06 | 0.07 | | |
| | 190 | 0.01 | 0.00 | 0.00 | | |
| | 194 | 0.01 | 0.01 | 0.03 | | |
| D18SCA225 | 160 | 0.16 | 0.20 | 0.21 | | |
| | 168 | 0.02 | 0.04 | 0.00 | | |
| | 170 | 0.00 | 0.00 | 0.01 | | |
| | 172 | 0.47 | 0.38 | 0.42 | 0.09 | 0.04 |
| | 174 | 0.22 | 0.24 | 0.26 | | |
| | 176 | 0.04 | 0.04 | 0.05 | | |
| | 178 | 0.04 | 0.04 | 0.02 | | |
| | 180 | 0.02 | 0.01 | 0.01 | | |
| | 184 | 0.03 | 0.00 | 0.02 | | |
| D18SW3442 | 10 | 0.42 | 0.28 | 0.36 | 0.14 | 0.06 |
| | 12 | 0.01 | 0.01 | 0.01 | | |
| | 14 | 0.07 | 0.11 | 0.11 | | |
| | 16 | 0.12 | 0.17 | 0.12 | | |
| | 18 | 0.18 | 0.15 | 0.14 | | |
| | 20 | 0.05 | 0.09 | 0.09 | | |
| | 22 | 0.08 | 0.10 | 0.11 | | |
| | 24 | 0.05 | 0.08 | 0.03 | | |
| | 26 | 0.00 | 0.00 | 0.02 | | |
| | 38 | 0.00 | 0.00 | 0.00 | | |
| D18SCA213 | 112 | 0.12 | 0.17 | 0.07 | | |
| | 120 | 0.00 | 0.05 | 0.01 | | |
| | 122 | 0.03 | 0.03 | 0.04 | | |
| | 124 | 0.44 | 0.37 | 0.46 | | |

*FIG. 7D*

18p allele frequencies

| MARKERNAME | | off 105 | ntrans | control | | |
|---|---|---|---|---|---|---|
| | 126 | 0.30 | 0.24 | 0.35 | | |
| | 128 | 0.08 | 0.11 | 0.06 | | |
| | 130 | 0.00 | 0.00 | 0.00 | | |
| | 132 | 0.03 | 0.02 | 0.01 | | |
| | | | | | | |
| D18SGAT201 | 142 | 0.04 | 0.06 | 0.02 | | |
| | 146 | 0.08 | 0.08 | 0.06 | | |
| | 150 | 0.61 | 0.62 | 0.69 | | |
| | 154 | 0.15 | 0.15 | 0.12 | | |
| | 158 | 0.11 | 0.07 | 0.10 | | |
| | 162 | 0.02 | 0.02 | 0.00 | | |
| | | | | | | |
| D18SGAT203 | | | | | | |
| | 188 | 0.42 | 0.37 | 0.38 | | |
| | 192 | 0.12 | 0.14 | 0.17 | | |
| | 196 | 0.01 | 0.04 | 0.01 | | |
| | 200 | 0.02 | 0.04 | 0.01 | | |
| | 204 | 0.06 | 0.02 | 0.04 | | |
| | 208 | 0.19 | 0.21 | 0.20 | | |
| | 212 | 0.11 | 0.11 | 0.11 | | |
| | 216 | 0.09 | 0.07 | 0.08 | | |
| | | | | | | |
| D18SCA219 | 221 | 0.00 | | 0.01 | | |
| | 223 | 0.00 | | 0.00 | | |
| | 225 | 0.00 | | 0.00 | | |
| | 233 | 0.00 | | 0.00 | | |
| | 235 | 0.22 | | 0.21 | | |
| | 239 | 0.02 | | 0.01 | | |
| | 241 | 0.54 | | 0.63 | | |
| | 243 | 0.07 | | 0.07 | | |
| | 245 | 0.13 | | 0.06 | | |
| | | | | | | |
| MARKERNAME | | off 105 | ntrans | control | | |
| | | | | | | |

*FIG. 7E*

18p allele frequencies

| MARKERNAME | | off 105 | ntrans | control | | |
|---|---|---|---|---|---|---|
| D18S1105 | 101 | 0.16 | 0.11 | | | |
| | 103 | 0.12 | 0.08 | | | |
| | 105 | 0.03 | 0.02 | | | |
| | 81 | 0.02 | 0.01 | | | |
| | 83 | 0.01 | 0.02 | | | |
| | 85 | 0.51 | 0.54 | | | |
| | 87 | 0.01 | 0.06 | | | |
| | 91 | 0.00 | 0.00 | | | |
| | 95 | 0.01 | 0.04 | | | |
| | 97 | 0.04 | 0.04 | | | |
| | 99 | 0.08 | 0.06 | | | |
| | | | | | | |
| D18SCA209 | 173 | 0.57 | 0.53 | 0.69 | | |
| | 175 | 0.02 | 0.03 | 0.04 | | |
| | 177 | 0.20 | 0.18 | 0.09 | | |
| | 179 | 0.01 | 0.03 | 0.00 | | |
| | 181 | 0.19 | 0.24 | 0.18 | | |
| | 187 | 0.00 | 0.00 | 0.00 | | |
| | | | | | | |
| D18SCA202 | 182 | 0.16 | 0.14 | | | |
| | 184 | 0.02 | 0.00 | | | |
| | 186 | 0.01 | 0.01 | | | |
| | 190 | 0.09 | 0.02 | | | |
| | 192 | 0.10 | 0.16 | | | |
| | 194 | 0.10 | 0.09 | | | |
| | 196 | 0.37 | 0.35 | | | |
| | 198 | 0.09 | 0.10 | | | |
| | 200 | 0.05 | 0.08 | | | |
| | 202 | 0.00 | 0.03 | | | |
| | 208 | 0.00 | 0.00 | | | |
| | | | | | | |
| D18S1146 | 270 | 0.32 | 0.35 | | | |
| | 272 | 0.07 | 0.10 | | | |
| | 274 | 0.60 | 0.51 | | | |

*FIG. 7F*

18p allele frequencies

| MARKERNAME | | aff 105 | ntrans | control | | |
|---|---|---|---|---|---|---|
| | 276 | 0.02 | 0.04 | | | |
| | | | | | | |
| | | | | | | |
| D18S166D05 | 300 | 0.17 | 0.21 | 0.19 | | |
| | 304 | 0.16 | 0.12 | 0.14 | | |
| | 308 | 0.18 | 0.18 | 0.13 | | |
| | 312 | 0.35 | 0.26 | 0.36 | * * | |
| | 316 | 0.08 | 0.18 | 0.11 | | |
| | 320 | 0.04 | 0.04 | 0.03 | | |
| | 324 | 0.01 | 0.01 | 0.02 | | |
| | | | | | | |
| | | | | | | |
| D18S476 | 261 | 0.00 | 0.01 | 0.01 | | |
| | 263 | 0.01 | 0.04 | 0.04 | | |
| | 265 | 0.05 | 0.12 | 0.04 | | |
| | 267 | 0.20 | 0.26 | 0.23 | | |
| | 269 | 0.08 | 0.09 | 0.04 | | |
| | 271 | 0.56 | 0.38 | 0.54 | * * * | |
| | 273 | 0.04 | 0.08 | 0.07 | | |
| | 275 | 0.04 | 0.03 | 0.03 | | |

FIG. 7G

Affected haplotypes

| 18p | PAN | MAN | ca212 | | 1140 | | 59 | | ca231 | | ta201 |
|---|---|---|---|---|---|---|---|---|---|---|---|
| 200 | 279 | 280 | 218 | 1 | 268 | 1 | 158 | 1 | 186 | 1 | 242 |
| 200 | | | 200 | 1 | 268 | 1 | 158 | 1 | 186 | 1 | 248 |
| 204 | 309 | 349 | 200 | 1 | 282 | 1 | 150 | 1 | 202 | 1 | 220 |
| 204 | | | 206 | 1 | 268 | 1 | 158 | 1 | 184 | 1 | 250 |
| 206 | 1 | 2 | 218 | 0 | 276 | 0 | 156 | 0 | 186 | 0 | 252 |
| 206 | | | 200 | 0 | 268 | 0 | 148 | 0 | 184 | 0 | 248 |
| 207 | 277 | 278 | 200 | 1 | 268 | 1 | 154 | 1 | 194 | 1 | 220 |
| 207 | | | 204 | 1 | 268 | 1 | 158 | 1 | 184 | 1 | 230 |
| 209 | 0 | 0 | 200 | 1 | 268 | 0 | 154 | 1 | 186 | 0 | 242 |
| 209 | | | 200 | 1 | 256 | 0 | 150 | 1 | 184 | 0 | 254 |
| 213 | 0 | 0 | 216 | 0 | 272 | 1 | 150 | 1 | 186 | 0 | 250 |
| 213 | | | 200 | 0 | 282 | 1 | 150 | 1 | 184 | 0 | 238 |
| 214 | 460 | 459 | 202 | 1 | 268 | 1 | 158 | 1 | 200 | 1 | 220 |
| 214 | | | 216 | 1 | 276 | 1 | 154 | 1 | 186 | 1 | 242 |
| 215 | 1 | 270 | 218 | 1 | 276 | 1 | 160 | 0 | 186 | 1 | 242 |
| 215 | | | 200 | 1 | 268 | 1 | 154 | 0 | 186 | 1 | 230 |
| 216 | 1 | 259 | 204 | 1 | 278 | 0 | 156 | 1 | 186 | 0 | 230 |
| 216 | | | 200 | 1 | 268 | 0 | 162 | 1 | 184 | 0 | 252 |
| 218 | 273 | 272 | 200 | 1 | 268 | 1 | 162 | 1 | 186 | 1 | 220 |
| 218 | | | 200 | 1 | 268 | 1 | 158 | 1 | 186 | 1 | 246 |
| 219 | 0 | 0 | 202 | 1 | 256 | 1 | 154 | 1 | 186 | 1 | 230 |
| 219 | | | 200 | 1 | 268 | 1 | 168 | 1 | 184 | 1 | 250 |
| 220 | 267 | 2 | 216 | 0 | 268 | 1 | 152 | 1 | 186 | 1 | 230 |
| 220 | | | 200 | 0 | 268 | 1 | 154 | 1 | 186 | 1 | 232 |
| 221 | 0 | 0 | 202 | 1 | 268 | 1 | 160 | 1 | 184 | 0 | 250 |
| 221 | | | 202 | 1 | 268 | 1 | 154 | 1 | 186 | 0 | 250 |
| 223 | 0 | 0 | 202 | 1 | 280 | 0 | 148 | 0 | 184 | 0 | 256 |
| 223 | | | 202 | 1 | 268 | 0 | 154 | 0 | 186 | 0 | 252 |
| 225 | 264 | 2 | 200 | 1 | 268 | 1 | 164 | 1 | 186 | 1 | 230 |
| 225 | | | 200 | 1 | 268 | 1 | 158 | 1 | 186 | 1 | 246 |
| 226 | 1 | 2 | 202 | 1 | 268 | 0 | 154 | 0 | 186 | 0 | 230 |
| 226 | | | 202 | 1 | 256 | 0 | 148 | 0 | 184 | 0 | 254 |
| 228 | 1 | 260 | 200 | 1 | 268 | 1 | 150 | 1 | 202 | 1 | 220 |
| 228 | | | 200 | 1 | 268 | 1 | 158 | 1 | 186 | 1 | 242 |

FIG. 8A

| | at201 | PD | ca225 | | w3442 | | ca213 | | ga201 | | ga203 | |
|---|---|---|---|---|---|---|---|---|---|---|---|---|
| 1 | 178 | 1 | 160 | 1 | 14 | 1 | 112 | 1 | 150 | 1 | 188 | 1 |
| 1 | 170 | 1 | 160 | 1 | 14 | 1 | 124 | 1 | 150 | 1 | 208 | 1 |
| 1 | 170 | 1 | 160 | 1 | 18 | 1 | 124 | 1 | 154 | 1 | 208 | 1 |
| 1 | 170 | 1 | 184 | 1 | 22 | 1 | 112 | 1 | 158 | 1 | 212 | 1 |
| 0 | 186 | 0 | 174 | 0 | 18 | 0 | 124 | 1 | 150 | 0 | 212 | 0 |
| 0 | 170 | 0 | 160 | 0 | 14 | 0 | 124 | 1 | 146 | 0 | 188 | 0 |
| 1 | 170 | 1 | 178 | 1 | 18 | 1 | 128 | 1 | 146 | 1 | 192 | 1 |
| 1 | 178 | 1 | 176 | 1 | 22 | 1 | 112 | 1 | 154 | 1 | 216 | 1 |
| 1 | 170 | 1 | 172 | 1 | 10 | 1 | 126 | 0 | 146 | 1 | 188 | 1 |
| 1 | 186 | 1 | 172 | 1 | 16 | 1 | 124 | 0 | 158 | 1 | 188 | 1 |
| 1 | 170 | 1 | 160 | 1 | 10 | 1 | 124 | 1 | 150 | 1 | 212 | 1 |
| 1 | 170 | 1 | 180 | 1 | 14 | 1 | 124 | 1 | 150 | 1 | 196 | 1 |
| 1 | 178 | 1 | 176 | 1 | 10 | 1 | 126 | 1 | 150 | 1 | 188 | 1 |
| 1 | 170 | 1 | 176 | 1 | 18 | 1 | 124 | 1 | 150 | 1 | 188 | 1 |
| 1 | 178 | 1 | 174 | 1 | 14 | 1 | 124 | 1 | 154 | 0 | 192 | 1 |
| 1 | 170 | 1 | 160 | 1 | 14 | 1 | 124 | 1 | 150 | 0 | 188 | 1 |
| 1 | 178 | 1 | 170 | 1 | 16 | 1 | 130 | 1 | 154 | 0 | 216 | 1 |
| 1 | 170 | 1 | 160 | 1 | 14 | 1 | 128 | 1 | 150 | 0 | 192 | 1 |
| 1 | 186 | 1 | 172 | 0 | 10 | 1 | 112 | 1 | 150 | 1 | 212 | 1 |
| 1 | 170 | 1 | 174 | 0 | 20 | 1 | 124 | 1 | 158 | 1 | 188 | 1 |
| 1 | 178 | 1 | 172 | 1 | 10 | 1 | 124 | 1 | 154 | 1 | 188 | 1 |
| 1 | 170 | 1 | 174 | 1 | 16 | 1 | 126 | 1 | 146 | 1 | 188 | 1 |
| 1 | 178 | 1 | 176 | 1 | 10 | 1 | 126 | 1 | 154 | 1 | 208 | 1 |
| 1 | 178 | 1 | 172 | 1 | 10 | 1 | 126 | 1 | 142 | 1 | 212 | 1 |
| 1 | 178 | 0 | 174 | 0 | 18 | 0 | 124 | 1 | 154 | 1 | 216 | 1 |
| 1 | 170 | 0 | 172 | 0 | 10 | 0 | 126 | 1 | 158 | 1 | 188 | 1 |
| 0 | 186 | 0 | 174 | 0 | 18 | 1 | 124 | 1 | 158 | 0 | 212 | 0 |
| 0 | 178 | 0 | 172 | 0 | 18 | 1 | 124 | 1 | 146 | 0 | 208 | 0 |
| 1 | 178 | 0 | 172 | 0 | 26 | 0 | 124 | 1 | 158 | 1 | 216 | 1 |
| 1 | 170 | 0 | 168 | 0 | 10 | 0 | 124 | 1 | 158 | 1 | 188 | 1 |
| 0 | 178 | 0 | 172 | 0 | 10 | 0 | 124 | 1 | 150 | 0 | 188 | 1 |
| 0 | 170 | 0 | 174 | 0 | 16 | 0 | 124 | 1 | 142 | 0 | 188 | 1 |
| 1 | 170 | 1 | 174 | 0 | 18 | 1 | 128 | 1 | 150 | 1 | 192 | 1 |
| 1 | 178 | 1 | 172 | 0 | 18 | 1 | 124 | 1 | 158 | 1 | 208 | 1 |

*FIG. 8B*

Affected haplotypes

| ca219 | | 1105 | | ca209 | | ca202 | | 1146 | | 166d05 | | 476 | |
|---|---|---|---|---|---|---|---|---|---|---|---|---|---|
| 241 | 1 | 85 | 1 | 173 | 1 | 192 | 1 | 272 | 1 | 312 | 1 | 271 | 1 |
| 233 | 1 | 99 | 1 | 181 | 1 | 196 | 1 | 270 | 1 | 304 | 1 | 271 | 1 |
| 241 | 1 | 85 | 1 | 173 | 1 | 182 | 1 | 274 | 0 | 312 | 1 | 273 | 1 |
| 245 | 1 | 103 | 1 | 177 | 1 | 194 | 1 | 270 | 0 | 308 | 1 | 267 | 1 |
| 241 | 1 | 85 | 1 | 173 | 1 | 198 | 0 | 274 | 1 | 308 | 0 | 275 | 0 |
| 241 | 1 | 85 | 1 | 173 | 1 | 194 | 0 | 274 | 1 | 304 | 0 | 271 | 0 |
| 241 | 1 | 87 | 1 | 173 | 1 | 182 | 1 | 272 | 1 | 300 | 1 | 271 | 1 |
| 235 | 1 | 101 | 1 | 181 | 1 | 196 | 1 | 274 | 1 | 312 | 1 | 271 | 1 |
| 235 | 1 | 85 | 1 | 173 | 1 | 182 | 1 | 274 | 1 | 312 | 1 | 271 | 1 |
| 243 | 1 | 85 | 1 | 173 | 1 | 192 | 1 | 274 | 1 | 316 | 1 | 267 | 1 |
| 245 | 1 | 103 | 1 | 177 | 1 | 194 | 0 | 274 | 0 | 312 | 1 | 271 | 1 |
| 235 | 1 | 91 | 1 | 181 | 1 | 182 | 0 | 270 | 0 | 316 | 1 | 271 | 1 |
| 241 | 1 | 85 | 1 | 173 | 1 | 182 | 1 | 274 | 1 | 312 | 1 | 271 | 1 |
| 241 | 1 | 103 | 1 | 177 | 1 | 196 | 1 | 274 | 1 | 312 | 1 | 271 | 1 |
| 241 | 1 | 85 | 1 | 173 | 1 | 196 | 0 | 270 | 1 | 300 | 1 | 271 | 0 |
| 235 | 1 | 85 | 1 | 181 | 1 | 190 | 0 | 274 | 1 | 312 | 1 | 267 | 0 |
| 235 | 1 | 81 | 1 | 173 | 1 | 182 | 1 | 274 | 1 | 324 | 1 | 271 | 0 |
| 223 | 1 | 83 | 1 | 173 | 1 | 192 | 1 | 274 | 1 | 300 | 1 | 267 | 0 |
| 245 | 1 | 103 | 1 | 177 | 1 | 196 | 1 | 274 | 1 | 312 | 1 | 271 | 1 |
| 241 | 1 | 85 | 1 | 173 | 1 | 182 | 1 | 270 | 1 | 312 | 1 | 265 | 1 |
| 241 | 1 | 105 | 0 | 173 | 1 | 196 | 1 | 270 | 1 | 304 | 1 | 267 | 1 |
| 241 | 1 | 101 | 0 | 173 | 1 | 196 | 1 | 270 | 1 | 308 | 1 | 271 | 1 |
| 241 | 1 | 87 | 0 | 173 | 1 | 192 | 1 | 274 | 1 | 312 | 1 | 271 | 1 |
| 241 | 1 | 85 | 0 | 173 | 1 | 196 | 1 | 274 | 1 | 304 | 1 | 267 | 1 |
| 245 | 1 | 97 | 1 | 177 | 1 | 194 | 1 | 274 | 1 | 312 | 0 | 271 | 1 |
| 235 | 1 | 99 | 1 | 181 | 1 | 198 | 1 | 274 | 1 | 300 | 0 | 271 | 1 |
| 241 | 0 | 95 | 0 | 181 | 0 | 198 | 0 | 274 | 1 | 320 | 0 | 273 | 0 |
| 235 | 0 | 85 | 0 | 173 | 0 | 196 | 0 | 274 | 1 | 308 | 0 | 271 | 0 |
| 235 | 1 | 101 | 0 | 181 | 0 | 196 | 0 | 272 | 1 | 312 | 1 | 271 | 1 |
| 235 | 1 | 85 | 0 | 173 | 0 | 200 | 1 | 274 | 1 | 308 | 1 | 271 | 1 |
| 241 | 0 | 85 | 0 | 173 | 1 | 200 | 0 | 274 | 0 | 312 | 0 | 271 | 0 |
| 243 | 0 | 101 | 0 | 173 | 0 | 196 | 0 | 270 | 0 | 304 | 0 | 267 | 0 |
| 241 | 1 | 85 | 1 | 173 | 1 | 182 | 1 | 274 | 1 | 316 | 1 | 271 | 0 |
| 241 | 1 | 99 | 1 | 173 | 1 | 200 | 1 | 274 | 1 | 300 | 1 | 269 | 0 |

FIG. 8C

Affected haplotypes

| 18p | PAN | MAN | ca212 | | 1140 | | 59 | | ca231 | | ta201 |
|---|---|---|---|---|---|---|---|---|---|---|---|
| 229 | 257 | 2 | 200 | 1 | 268 | 0 | 154 | 1 | 186 | 1 | 244 |
| 229 | | | 216 | 1 | 256 | 0 | 158 | 1 | 186 | 1 | 244 |
| 230 | 0 | 0 | 202 | 1 | 268 | 1 | 160 | 1 | 186 | 1 | 230 |
| 230 | | | 202 | 1 | 268 | 1 | 158 | 1 | 186 | 1 | 248 |
| 231 | 299 | 298 | 216 | 1 | 268 | 1 | 158 | 1 | 186 | 1 | 220 |
| 231 | | | 218 | 1 | 268 | 1 | 158 | 1 | 186 | 1 | 244 |
| 232 | 1 | 310 | 206 | 1 | 268 | 1 | 150 | 1 | 186 | 1 | 222 |
| 232 | | | 200 | 1 | 268 | 1 | 158 | 1 | 186 | 1 | 230 |
| 234 | 1 | 261 | 200 | 1 | 268 | 1 | 148 | 1 | 184 | 1 | 252 |
| 234 | | | 200 | 1 | 268 | 1 | 158 | 1 | 186 | 1 | 262 |
| 235 | 0 | 0 | 200 | 1 | 276 | 0 | 150 | 1 | 186 | 0 | 248 |
| 235 | | | 202 | 1 | 268 | 0 | 156 | 1 | 184 | 0 | 214 |
| 237 | 0 | 0 | 200 | 1 | 268 | 1 | 158 | 1 | 186 | 1 | 214 |
| 237 | | | 200 | 1 | 268 | 1 | 154 | 1 | 186 | 1 | 230 |
| 238 | 456 | 457 | 202 | 1 | 268 | 1 | 154 | 1 | 186 | 1 | 230 |
| 238 | | | 200 | 1 | 268 | 1 | 158 | 1 | 186 | 1 | 230 |
| 239 | 312 | 2 | 218 | 1 | 268 | 1 | 160 | 1 | 186 | 0 | 248 |
| 239 | | | 200 | 1 | 268 | 1 | 158 | 1 | 184 | 0 | 242 |
| 240 | 1 | 2 | 200 | 1 | 268 | 1 | 158 | 0 | 186 | 1 | 242 |
| 240 | | | 200 | 1 | 268 | 1 | 148 | 0 | 186 | 1 | 230 |
| 241 | 1 | 342 | 216 | 1 | 268 | 1 | 158 | 1 | 184 | 0 | 246 |
| 241 | | | 200 | 1 | 268 | 1 | 158 | 1 | 186 | 0 | 250 |
| 242 | 0 | 0 | 216 | 1 | 268 | 1 | 156 | 0 | 186 | 1 | 244 |
| 242 | | | 200 | 1 | 268 | 1 | 154 | 0 | 186 | 1 | 244 |
| 243 | 347 | 274 | 200 | 1 | 268 | 1 | 154 | 1 | 186 | 1 | 230 |
| 243 | | 1 | 218 | 1 | 268 | 1 | 150 | 1 | 186 | 1 | 252 |
| 245 | 0 | 0 | 200 | 1 | 268 | 1 | 154 | 1 | 186 | 1 | 232 |
| 245 | | | 202 | 1 | 268 | 1 | 150 | 1 | 186 | 1 | 242 |
| 246 | 1 | 262 | 204 | 0 | 270 | 1 | 158 | 1 | 186 | 1 | 246 |
| 246 | | | 202 | 0 | 268 | 1 | 154 | 1 | 186 | 1 | 242 |
| 247 | 303 | 302 | 202 | 1 | 268 | 1 | 154 | 1 | 186 | 1 | 230 |
| 247 | | | 200 | 1 | 268 | 1 | 154 | 1 | 186 | 1 | 242 |
| 248 | 334 | 333 | 200 | 1 | 268 | 1 | 154 | 1 | 184 | 1 | 232 |
| 248 | | | 202 | 1 | 268 | 1 | 154 | 1 | 186 | 1 | 244 |

FIG. 8D

| | at201 | | PD | ca225 | | w3442 | | ca213 | | ga201 | | ga203 | |
|---|---|---|---|---|---|---|---|---|---|---|---|---|---|
| 1 | 170 | 1 | 1 | 174 | 1 | 10 | 1 | 126 | 1 | 150 | 1 | 192 | 1 |
| 1 | 186 | 1 | 1 | 174 | 1 | 24 | 1 | 124 | 1 | 146 | 1 | 216 | 1 |
| 1 | 170 | 1 | 1 | 172 | 0 | 18 | 1 | 122 | 1 | 150 | 1 | 208 | 1 |
| 1 | 170 | 1 | 1 | 160 | 0 | 12 | 1 | 124 | 1 | 150 | 1 | 216 | 1 |
| 1 | 170 | 1 | 1 | 172 | 1 | 20 | 1 | 124 | 1 | 150 | 1 | 204 | 1 |
| 1 | 170 | 1 | 1 | 174 | 1 | 22 | 1 | 126 | 1 | 150 | 1 | 204 | 1 |
| 1 | 170 | 1 | 1 | 172 | 1 | 20 | 1 | 124 | 1 | 154 | 0 | 188 | 1 |
| 1 | 170 | 1 | 1 | 178 | 1 | 10 | 1 | 126 | 1 | 150 | 0 | 188 | 1 |
| 1 | 170 | 1 | 1 | 174 | 1 | 10 | 1 | 126 | 1 | 162 | 1 | 208 | 1 |
| 1 | 170 | 1 | 1 | 174 | 1 | 24 | 1 | 126 | 1 | 150 | 1 | 192 | 1 |
| 1 | 170 | 1 | 1 | 172 | 1 | 10 | 1 | 112 | 1 | 154 | 0 | 192 | 1 |
| 1 | 170 | 1 | 1 | 174 | 1 | 22 | 1 | 124 | 1 | 150 | 0 | 192 | 1 |
| 1 | 178 | 1 | 1 | 172 | 1 | 16 | 1 | 126 | 0 | 150 | 1 | 208 | 1 |
| 1 | 186 | 1 | 1 | 172 | 1 | 16 | 1 | 124 | 0 | 154 | 1 | 208 | 1 |
| 1 | 178 | 1 | 1 | 172 | 1 | 10 | 1 | 128 | 1 | 150 | 1 | 208 | 1 |
| 1 | 170 | 1 | 1 | 178 | 1 | 14 | 1 | 112 | 1 | 150 | 1 | 188 | 1 |
| 1 | 170 | 1 | 1 | 172 | 1 | 16 | 1 | 124 | 1 | 154 | 0 | 208 | 1 |
| 1 | 178 | 1 | 1 | 172 | 1 | 18 | 1 | 124 | 1 | 150 | 0 | 188 | 1 |
| 0 | 178 | 1 | 1 | 172 | 1 | 18 | 1 | 128 | 0 | 154 | 0 | 188 | 1 |
| 0 | 178 | 1 | 1 | 172 | 1 | 18 | 1 | 124 | 0 | 146 | 0 | 188 | 1 |
| 1 | 170 | 1 | 1 | 172 | 1 | 20 | 1 | 126 | 0 | 150 | 1 | 188 | 1 |
| 1 | 170 | 1 | 1 | 172 | 1 | 10 | 1 | 124 | 0 | 142 | 1 | 188 | 1 |
| 1 | 186 | 1 | 1 | 174 | 1 | 14 | 0 | 126 | 1 | 150 | 1 | 192 | 0 |
| 1 | 170 | 1 | 1 | 160 | 1 | 10 | 0 | 126 | 1 | 150 | 1 | 188 | 0 |
| 1 | 178 | 0 | 0 | 172 | 0 | 10 | 1 | 124 | 1 | 150 | 1 | 188 | 0 |
| 1 | 170 | 0 | 0 | 160 | 0 | 38 | 1 | 124 | 1 | 146 | 1 | 208 | 0 |
| 1 | 178 | 0 | 0 | 172 | 1 | 10 | 1 | 126 | 1 | 154 | 1 | 216 | 1 |
| 1 | 170 | 0 | 0 | 172 | 1 | 16 | 1 | 124 | 1 | 150 | 1 | 192 | 1 |
| 1 | 178 | 0 | 0 | 172 | 1 | 16 | 1 | 126 | 1 | 150 | 1 | 188 | 1 |
| 1 | 170 | 0 | 0 | 172 | 1 | 22 | 1 | 122 | 1 | 150 | 1 | 216 | 1 |
| 1 | 178 | 1 | 1 | 174 | 1 | 10 | 1 | 124 | 1 | 158 | 1 | 188 | 1 |
| 1 | 170 | 1 | 1 | 176 | 1 | 10 | 1 | 126 | 1 | 150 | 1 | 216 | 1 |
| 1 | 170 | 1 | 1 | 160 | 1 | 20 | 1 | 112 | 1 | 150 | 1 | | 0 |
| 1 | 170 | 1 | 1 | 174 | 1 | 16 | 1 | 112 | 1 | 146 | 1 | | 0 |

*FIG. 8E*

Affected haplotypes

| ca219 | | 1105 | | ca209 | | ca202 | | 1146 | | 166d05 | | 476 | |
|---|---|---|---|---|---|---|---|---|---|---|---|---|---|
| 241 | 1 | 85 | 1 | 177 | 1 | 196 | 1 | 270 | 1 | 304 | 1 | 271 | 1 |
| 245 | 1 | 99 | 1 | 177 | 1 | 192 | 1 | 274 | 1 | 308 | 1 | 265 | 1 |
| 245 | 1 | 97 | 1 | 177 | 1 | 196 | 0 | 274 | 1 | 304 | 1 | 275 | 0 |
| 245 | 1 | 99 | 1 | 177 | 1 | 192 | 0 | 270 | 1 | 308 | 1 | 267 | 0 |
| 243 | 1 | 103 | 1 | 175 | 1 | 198 | 1 | 274 | 1 | 300 | 1 | 271 | 1 |
| 245 | 1 | 85 | 1 | 173 | 1 | 194 | 1 | 274 | 1 | 312 | 1 | 271 | 1 |
| 235 | 1 | 101 | 0 | 181 | 0 | 196 | 1 | 270 | 1 | 316 | 1 | 267 | 1 |
| 235 | 1 | 85 | 0 | 173 | 0 | 196 | 1 | 274 | 1 | 300 | 1 | 271 | 1 |
| 241 | 1 | 85 | 1 | 173 | 1 | 200 | 0 | 270 | 1 | 304 | 1 | 273 | 1 |
| 241 | 1 | 85 | 1 | 177 | 1 | 198 | 0 | 274 | 1 | 308 | 1 | 271 | 1 |
| 241 | 0 | 101 | 0 | 177 | 1 | 182 | 1 | 274 | 1 | 312 | 1 | 273 | 1 |
| 235 | 0 | 85 | 0 | 177 | 1 | 190 | 1 | 274 | 1 | 300 | 1 | 275 | 1 |
| 241 | 1 | 85 | 1 | 173 | 1 | 194 | 1 | 274 | 1 | 308 | 1 | 271 | 1 |
| 239 | 1 | 85 | 1 | 173 | 1 | 196 | 1 | 270 | 1 | 308 | 1 | 271 | 1 |
| 245 | 0 | 85 | 1 | 177 | 1 | 198 | 1 | 274 | 1 | 320 | 1 | 271 | 1 |
| 241 | 0 | 85 | 1 | 173 | 1 | 196 | 1 | 274 | 1 | 308 | 1 | 265 | 1 |
| 241 | 1 | 99 | 0 | 177 | 1 | 198 | 1 | 270 | 1 | 312 | 1 | 271 | 0 |
| 241 | 1 | 85 | 0 | 173 | 1 | 182 | 1 | 270 | 1 | 312 | 1 | 263 | 0 |
| 241 | 0 | 101 | 0 | 187 | 0 | 200 | 0 | 270 | 1 | 312 | 0 | 271 | 1 |
| 235 | 0 | 85 | 0 | 173 | 0 | 182 | 0 | 270 | 1 | 300 | 0 | 271 | 1 |
| 241 | 0 | 101 | 1 | 181 | 0 | 196 | - | 274 | 1 | 308 | 0 | 275 | 0 |
| 235 | 0 | 83 | 1 | 173 | 0 | 196 | 1 | 274 | 1 | 304 | 0 | 267 | 0 |
| 241 | 1 | 85 | 1 | 173 | 1 | 196 | 1 | 270 | 1 | 300 | 1 | 275 | 1 |
| 235 | 1 | 101 | 1 | 181 | 1 | 196 | 1 | 272 | 1 | 300 | 1 | 271 | 1 |
| 241 | 1 | 85 | 1 | 173 | 1 | 182 | 1 | 270 | 1 | 300 | 1 | 271 | 1 |
| 239 | 1 | 103 | 1 | 173 | 1 | 194 | 1 | 274 | 1 | 312 | 1 | 271 | 1 |
| 241 | 1 | 85 | 1 | 173 | 1 | 194 | 1 | 274 | 1 | 316 | 1 | 271 | 1 |
| 241 | 1 | 85 | 1 | 173 | 1 | 196 | 1 | 270 | 1 | 308 | 1 | 271 | 1 |
| 241 | 1 | 105 | 1 | 173 | 1 | 196 | 1 | 274 | 1 | 312 | 0 | 271 | 0 |
| 235 | 1 | 101 | 1 | 181 | 1 | 182 | 1 | 270 | 1 | 300 | 0 | 267 | 0 |
| 243 | 1 | 85 | 1 | 173 | 1 | 196 | 1 | 274 | 1 | 300 | 1 | 271 | 1 |
| 241 | 1 | 85 | 1 | 173 | 1 | 190 | 1 | 270 | 1 | 316 | 1 | 271 | 1 |
| 241 | 1 | 85 | 1 | 177 | 1 | 196 | 1 | 274 | 1 | 304 | 1 | 271 | 0 |
| 241 | 1 | 85 | 1 | 173 | 1 | 196 | 1 | 270 | 1 | 312 | 1 | 267 | 0 |

*FIG. 8F*

Affected haplotypes

| 18p | PAN | MAN | ca212 | | 1140 | | 59 | | ca231 | | ta201 |
|---|---|---|---|---|---|---|---|---|---|---|---|
| 249 | 1 | 2 | 200 | 0 | 268 | 0 | 154 | 0 | 186 | 1 | 230 |
| 249 | | | 216 | 0 | 256 | 0 | 148 | 0 | 186 | 1 | 246 |
| 251 | 301 | 300 | 216 | 1 | 272 | 1 | 150 | 1 | 184 | 1 | 250 |
| 251 | | | 216 | 1 | 268 | 1 | 158 | 1 | 186 | 1 | 244 |
| 252 | 1 | 285 | 200 | 0 | 268 | 1 | 154 | 1 | 186 | 1 | 230 |
| 252 | | | 204 | 0 | 268 | 1 | 158 | 1 | 186 | 1 | 246 |
| 253 | 1 | 258 | 216 | 0 | 268 | 1 | 160 | 1 | 186 | 1 | 228 |
| 253 | | | 200 | 0 | 268 | 1 | 154 | 1 | 186 | 1 | 230 |
| 254 | 467 | 2 | 202 | 1 | 268 | 1 | 160 | 1 | 186 | 1 | 230 |
| 254 | | | 200 | 1 | 268 | 1 | 154 | 1 | 186 | 1 | 230 |
| 265 | 1 | 266 | 216 | 1 | 272 | 1 | 150 | 1 | 184 | 1 | 250 |
| 265 | | | 202 | 1 | 268 | 1 | 154 | 1 | 186 | 1 | 230 |
| 311 | 1 | 458 | 216 | 1 | 268 | 1 | 154 | 1 | 186 | 1 | 244 |
| 311 | | | 200 | 1 | 268 | 1 | 162 | 1 | 186 | 1 | 242 |
| 314 | 348 | 313 | 200 | 1 | 268 | 1 | 148 | 1 | 184 | 1 | 248 |
| 314 | | | 216 | 1 | 268 | 1 | 162 | 1 | 184 | 1 | 250 |
| 316 | 1 | 317 | 214 | 1 | 268 | 1 | 154 | 1 | 186 | 1 | 230 |
| 316 | | | 200 | 1 | 268 | 1 | 154 | 1 | 186 | 1 | 242 |
| 319 | 318 | 2 | 202 | 0 | 272 | 0 | 158 | 0 | 184 | 0 | 244 |
| 319 | | | 200 | 0 | 256 | 0 | 154 | 0 | 186 | 0 | 244 |
| 321 | 1 | 320 | 202 | 0 | 268 | 1 | 158 | 0 | | 0 | |
| 321 | | | 200 | 0 | 268 | 1 | 154 | 0 | | 0 | |
| 324 | 0 | 0 | 202 | 1 | 268 | 1 | 158 | 1 | 186 | 1 | 232 |
| 324 | | | 216 | 1 | 268 | 1 | 150 | 1 | 196 | 1 | 220 |
| 326 | 325 | 336 | 206 | 1 | 280 | 1 | 152 | 1 | 198 | 1 | 232 |
| 326 | | | 202 | 1 | 268 | 1 | 154 | 1 | 186 | 1 | 232 |
| 329 | 1 | 330 | 200 | 1 | 268 | 1 | 154 | 0 | 186 | 1 | 248 |
| 329 | | | 206 | 1 | 268 | 1 | 148 | 0 | 186 | 1 | 234 |
| 211 | 1 | 2 | 200 | 0 | 268 | 1 | 154 | 0 | 186 | 0 | 230 |
| 211 | | | 204 | 0 | 268 | 1 | 148 | 0 | 198 | 0 | 252 |
| 353 | 1 | 352 | 218 | 1 | 280 | 0 | 148 | 1 | 186 | 1 | 246 |
| 353 | | | 200 | 1 | 268 | 0 | 148 | 1 | 186 | 1 | 246 |
| 356 | 362 | 2 | 216 | 1 | 268 | 1 | 154 | 1 | 186 | 0 | 248 |
| 356 | | | 204 | 1 | 268 | 1 | 164 | 1 | 190 | 0 | 232 |

*FIG. 8C*

| | at201 | PD | ca225 | | w3442 | | ca213 | | ga201 | | ga203 | |
|---|---|---|---|---|---|---|---|---|---|---|---|---|
| 0 | 194 | 0 | 172 | 0 | 10 | 0 | 124 | 1 | 150 | 1 | 188 | 1 |
| 0 | 178 | 0 | 174 | 0 | 16 | 0 | 124 | 1 | 150 | 1 | 188 | 1 |
| 1 | 170 | 1 | 160 | 1 | 10 | 1 | 124 | 1 | 150 | 1 | 212 | 1 |
| 1 | 186 | 1 | 174 | 1 | 20 | 1 | 124 | 1 | 150 | 1 | 188 | 1 |
| 1 | 178 | 1 | 172 | 1 | 10 | 1 | 124 | 0 | 150 | 1 | 188 | 1 |
| 1 | 170 | 1 | 160 | 1 | 18 | 1 | 126 | 0 | 150 | 1 | 216 | 1 |
| 1 | 170 | 1 | 160 | 1 | 16 | 1 | 124 | 1 | 150 | 1 | 188 | 1 |
| 1 | 178 | 1 | 160 | 1 | 16 | 1 | 126 | 1 | 150 | 1 | 216 | 1 |
| 1 | 170 | 0 | 172 | 1 | 18 | 1 | 122 | 1 | 150 | 1 | 208 | 0 |
| 1 | 178 | 0 | 172 | 1 | 10 | 1 | 124 | 1 | 142 | 1 | 188 | 0 |
| 1 | 170 | 1 | 160 | 1 | 10 | 1 | 126 | 0 | 150 | 1 | 212 | 1 |
| 1 | 178 | 1 | 172 | 1 | 10 | 1 | 124 | 0 | 150 | 1 | 188 | 1 |
| 1 | 170 | 1 | 160 | 1 | 10 | 1 | 126 | 1 | 150 | 1 | 188 | 1 |
| 1 | 186 | 1 | 174 | 1 | 10 | 1 | 124 | 1 | 158 | 1 | 208 | 1 |
| 1 | 170 | 1 | 168 | 1 | 18 | 0 | 124 | 1 | 150 | 1 | 208 | 1 |
| 1 | 170 | 1 | 172 | 1 | 10 | 0 | 126 | 1 | 150 | 1 | 188 | 1 |
| 1 | 178 | 1 | 172 | 1 | 10 | 1 | 124 | 1 | 150 | 1 | 208 | 0 |
| 1 | 170 | 1 | 172 | 1 | 10 | 1 | 126 | 1 | 150 | 1 | 188 | 0 |
| 1 | 178 | 0 | 184 | 0 | 10 | 1 | 126 | 0 | 150 | 1 | 188 | 1 |
| 1 | 170 | 0 | 174 | 0 | 10 | 1 | 112 | 0 | 150 | 1 | 188 | 1 |
| 0 | 178 | 1 | 178 | 0 | 18 | 1 | 128 | 0 | | 0 | | 0 |
| 0 | 170 | 1 | 172 | 0 | 10 | 1 | 124 | 0 | | 0 | | 0 |
| 1 | 178 | 1 | 172 | 0 | 24 | 1 | 112 | 1 | 150 | 1 | 212 | 1 |
| 1 | 170 | 1 | 160 | 0 | 18 | 1 | 128 | 1 | 154 | 1 | 208 | 1 |
| 1 | 170 | 1 | 172 | 1 | 16 | 1 | 124 | 1 | 150 | 1 | 188 | 1 |
| 1 | 178 | 1 | 172 | 1 | 16 | 1 | 132 | 1 | 150 | 1 | 192 | 1 |
| 1 | 170 | 1 | 160 | 1 | 14 | 1 | 128 | 1 | 150 | 1 | 188 | 1 |
| 1 | 170 | 1 | 172 | 1 | 22 | 1 | 124 | 1 | 150 | 1 | 208 | 1 |
| 0 | 178 | 1 | 172 | 1 | 10 | 0 | 126 | 0 | 150 | 0 | 188 | 1 |
| 0 | 178 | 1 | 172 | 1 | 18 | 0 | 112 | 0 | 154 | 0 | 188 | 1 |
| 1 | 170 | 1 | 160 | 1 | 18 | 1 | 132 | 1 | 154 | 1 | 192 | 1 |
| 1 | 170 | 1 | 172 | 1 | 18 | 1 | 112 | 1 | 146 | 1 | 192 | 1 |
| 1 | 178 | 0 | 172 | 1 | 10 | 0 | 124 | 1 | 150 | 1 | 208 | 1 |
| 1 | 170 | 0 | 172 | 1 | 18 | 0 | 126 | 1 | 150 | 1 | 216 | 1 |

FIG. 8H

Affected haplotypes

| ca219 | | 1105 | | ca209 | | ca202 | | 1146 | | 166d05 | | 476 | |
|---|---|---|---|---|---|---|---|---|---|---|---|---|---|
| 241 | 1 | 85 | 0 | 173 | 1 | 192 | 0 | 272 | 0 | 312 | 0 | 273 | 0 |
| 241 | 1 | 103 | 0 | 173 | 1 | 182 | 0 | 270 | 0 | 304 | 0 | 267 | 0 |
| 245 | 1 | 103 | 1 | 181 | 0 | 194 | 1 | 270 | 1 | 312 | 1 | 271 | 1 |
| 235 | 1 | 101 | 1 | 177 | 0 | 202 | 1 | 274 | 1 | 312 | 1 | 271 | 1 |
| 241 | 0 | 103 | 1 | 181 | 0 | 196 | 1 | 276 | 0 | 304 | 1 | 271 | 1 |
| 235 | 0 | 101 | 1 | 173 | 0 | 208 | 1 | 274 | 0 | 300 | 1 | 267 | 1 |
| 241 | 1 | 85 | 1 | 173 | 1 | 198 | 1 | 274 | 1 | 304 | 1 | 271 | 1 |
| 241 | 1 | 85 | 1 | 173 | 1 | 190 | 1 | 274 | 1 | 312 | 1 | 271 | 1 |
| 245 | 1 | 97 | 1 | 177 | 1 | 196 | 1 | 274 | 1 | 304 | 1 | 275 | 0 |
| 235 | 1 | 99 | 1 | 181 | 1 | 196 | 1 | 274 | 1 | 304 | 1 | 271 | 0 |
| 245 | 1 | 103 | 1 | 177 | 1 | 194 | 1 | 270 | 1 | 312 | 1 | 271 | 1 |
| 245 | 1 | 85 | 1 | 173 | 1 | 192 | 1 | 274 | 1 | 308 | 1 | 267 | 1 |
| 235 | 1 | 101 | 1 | 181 | 1 | 196 | 0 | 272 | 1 | 300 | 1 | 271 | 0 |
| 241 | 1 | 85 | 1 | 173 | 1 | 184 | 0 | 274 | 1 | 320 | 1 | 269 | 0 |
| 245 | 1 | 85 | 1 | 177 | 1 | 196 | 1 | 274 | 1 | 312 | 1 | 271 | 1 |
| 235 | 1 | 101 | 1 | 181 | 1 | 182 | 1 | 270 | 1 | 312 | 1 | 269 | 1 |
| 241 | 0 | 103 | 0 | 181 | 0 | 190 | 1 | 274 | 1 | 312 | 0 | 271 | 0 |
| 235 | 0 | 101 | 0 | 173 | 0 | 190 | 1 | 274 | 1 | 304 | 0 | 267 | 0 |
| 241 | 1 | 101 | 1 | 181 | 0 | 196 | 0 | 274 | 1 | 312 | 1 | 271 | 1 |
| 235 | 1 | 103 | 1 | 173 | 0 | 192 | 0 | 274 | 1 | 300 | 1 | 271 | 1 |
| | 0 | 101 | 1 | | 0 | | 0 | 270 | 1 | 304 | 1 | | 0 |
| | 0 | 85 | 1 | | 0 | | 0 | 272 | 1 | 300 | 1 | | 0 |
| 241 | 1 | 85 | 1 | 173 | 1 | 194 | 0 | 274 | 0 | 312 | 1 | 269 | 1 |
| 241 | 1 | 101 | 1 | 177 | 1 | 182 | 0 | 270 | 0 | 312 | 1 | 267 | 1 |
| 241 | 1 | 85 | 1 | 173 | 1 | 182 | 1 | 276 | 1 | 320 | 1 | 269 | 1 |
| 241 | 1 | 85 | 1 | 173 | 1 | 194 | 1 | 270 | 1 | 300 | 1 | 271 | 1 |
| 241 | 1 | 85 | 1 | 173 | 1 | 200 | 1 | 272 | 0 | 304 | 1 | 271 | 1 |
| 241 | 1 | 85 | 1 | 173 | 1 | 182 | 1 | 270 | 0 | 316 | 1 | 271 | 1 |
| 241 | 0 | 85 | 1 | 181 | 1 | 190 | 0 | 274 | 1 | 316 | 0 | 267 | 0 |
| 235 | 0 | 85 | 1 | 181 | 1 | 182 | 0 | 274 | 1 | 312 | 0 | 263 | 0 |
| 235 | 1 | 81 | 1 | 179 | 1 | 196 | 0 | 274 | 1 | 312 | 1 | 269 | 1 |
| 235 | 1 | 85 | 1 | 179 | 1 | 182 | 0 | 274 | 1 | 312 | 1 | 271 | 1 |
| 235 | 1 | 85 | 0 | 181 | 1 | 194 | 1 | 274 | 1 | 300 | 1 | 275 | 0 |
| 241 | 1 | 101 | 0 | 173 | 1 | 196 | 1 | 270 | 1 | 300 | 1 | 271 | 0 |

*FIG. 81*

Affected haplotypes

| 18p | PAN | MAN | ca212 | | 1140 | | 59 | | ca231 | | ta201 |
|---|---|---|---|---|---|---|---|---|---|---|---|
| 357 | 1 | 358 | 202 | 0 | 268 | 1 | 154 | 0 | 186 | 1 | 232 |
| 357 | | | 214 | 0 | 278 | 1 | 158 | 0 | 186 | 1 | 248 |
| 359 | 378 | 365 | 202 | 1 | 268 | 1 | 154 | 1 | 186 | 1 | 230 |
| 359 | | | 202 | 1 | 272 | 1 | 158 | 1 | 184 | 1 | 244 |
| 367 | 1 | 366 | 202 | 1 | 268 | 1 | 154 | 1 | 186 | 1 | 232 |
| 367 | | | 202 | 1 | 268 | 1 | 154 | 1 | 186 | 1 | 242 |
| 372 | 1 | 370 | 200 | 1 | 268 | 1 | 154 | 1 | 186 | 0 | |
| 372 | | | 216 | 1 | 268 | 1 | 148 | 1 | 184 | 0 | |
| 384 | 389 | 2 | 202 | 1 | 268 | 1 | 156 | 1 | 186 | 1 | 246 |
| 384 | | | 202 | 1 | 268 | 1 | 154 | 1 | 186 | 1 | 250 |
| 409 | 408 | 410 | 216 | 1 | 268 | 1 | 148 | 1 | 200 | 1 | 220 |
| 409 | | | 202 | 1 | 268 | 1 | 154 | 1 | 186 | 1 | 230 |
| 435 | 1 | 433 | 200 | 1 | 280 | 1 | 148 | 1 | 184 | 1 | 252 |
| 435 | | | 202 | 1 | 268 | 1 | 156 | 1 | 194 | 1 | 220 |
| 443 | 1 | 444 | 206 | 1 | 280 | 1 | 148 | 1 | 186 | 1 | 246 |
| 443 | | | 202 | 1 | 256 | 1 | 154 | 1 | 186 | 1 | 230 |
| 458 | 1 | 551 | 200 | 1 | 268 | 1 | 162 | 1 | 186 | 1 | 230 |
| 458 | | | 200 | 1 | 268 | 1 | 154 | 1 | 186 | 1 | 234 |
| 488 | 1 | 508 | 216 | 1 | 268 | 1 | 160 | 1 | 184 | 1 | 232 |
| 488 | | | 216 | 1 | 268 | 1 | 160 | 1 | 184 | 1 | 232 |
| 501 | 528 | 527 | 200 | 1 | 268 | 1 | 154 | 1 | 186 | 1 | 230 |
| 501 | | | 206 | 1 | 268 | 1 | 154 | 1 | 186 | 1 | 244 |
| 505 | 1 | 502 | 202 | 1 | 268 | 1 | 158 | 1 | 186 | 1 | 244 |
| 505 | | | 200 | 1 | 268 | 1 | 158 | 1 | 186 | 1 | 244 |
| 516 | 1 | 517 | 202 | 0 | 268 | 1 | 158 | 0 | | 0 | |
| 516 | | | 200 | 0 | 268 | 1 | 148 | 0 | | 0 | |
| 537 | 532 | 534 | 202 | 1 | 256 | 1 | 154 | 1 | 186 | 1 | 230 |
| 537 | | | 216 | 1 | 268 | 1 | 154 | 1 | 184 | 1 | 230 |
| 531 | 1 | 529 | 202 | 0 | 268 | 1 | 150 | 1 | 184 | 1 | 254 |
| 531 | | | 200 | 0 | 268 | 1 | 154 | 1 | 186 | 1 | 244 |
| 574 | 0 | 0 | 206 | 1 | 274 | 0 | 152 | 1 | 194 | 1 | 236 |
| 574 | | | 200 | 1 | 268 | 0 | 148 | 1 | 184 | 1 | 252 |
| 578 | 576 | 579 | 202 | 1 | 280 | 1 | 154 | 1 | 186 | 1 | 214 |
| 578 | | | 202 | 1 | 268 | 1 | 154 | 1 | 186 | 1 | 230 |

*FIG. 8J*

| at201 | | PD | ca225 | | w3442 | | ca213 | | ga201 | | ga203 | |
|---|---|---|---|---|---|---|---|---|---|---|---|---|
| 1 | 178 | 1 | 160 | 1 | 10 | 1 | 128 | 0 | 150 | 1 | 196 | 1 |
| 1 | 178 | 1 | 184 | 1 | 10 | 1 | 124 | 0 | 150 | 1 | 208 | 1 |
| 1 | 178 | 1 | 172 | 1 | 10 | 1 | 126 | 1 | 154 | 1 | 188 | 1 |
| 1 | 178 | 1 | 184 | 1 | 10 | 1 | 112 | 1 | 150 | 1 | 188 | 1 |
| 1 | 178 | 1 | 172 | 1 | 10 | 1 | 126 | 1 | 158 | 0 | 208 | 1 |
| 1 | 178 | 1 | 172 | 1 | 10 | 1 | 112 | 1 | 142 | 0 | 208 | 1 |
| 0 | | | 0 | 172 | 1 | 10 | 1 | 124 | 0 | 150 | 1 | | 0 |
| 0 | | | 0 | 174 | 1 | 10 | 1 | 126 | 0 | 150 | 1 | | 0 |
| 1 | 170 | 1 | 174 | 1 | 10 | 1 | 126 | 1 | 150 | 1 | 188 | 1 |
| 1 | 170 | 1 | 174 | 1 | 10 | 1 | 126 | 1 | 158 | 1 | 188 | 1 |
| 1 | 170 | 1 | 184 | 1 | 24 | 1 | 132 | 1 | 154 | 1 | 208 | 1 |
| 1 | 178 | 1 | 172 | 1 | 10 | 1 | 124 | 1 | 150 | 1 | 216 | 1 |
| 1 | 178 | 1 | 178 | 0 | 22 | 1 | 126 | 1 | 150 | 1 | 204 | 1 |
| 1 | 170 | 1 | 172 | 0 | 22 | 1 | 126 | 1 | 150 | 1 | 204 | 1 |
| 1 | 178 | 1 | 176 | 0 | 14 | 1 | 128 | 1 | 154 | 0 | 192 | 1 |
| 1 | 178 | 1 | 172 | 0 | 10 | 1 | 124 | 1 | 150 | 0 | 188 | 1 |
| 1 | 178 | 1 | 172 | 1 | 22 | 1 | 126 | 1 | 150 | 1 | 208 | 0 |
| 1 | 178 | 1 | 172 | 1 | 12 | 1 | 128 | 1 | 154 | 1 | 188 | 0 |
| 1 | 170 | 1 | 172 | 1 | 18 | 1 | 122 | 1 | 150 | 1 | 208 | 1 |
| 1 | 170 | 1 | 172 | 1 | 18 | 1 | 122 | 1 | 150 | 1 | 208 | 1 |
| 1 | 178 | 1 | 176 | 1 | 10 | 1 | 126 | 1 | 150 | 1 | 216 | 1 |
| 1 | 170 | 1 | 172 | 1 | 16 | 1 | 126 | 1 | 154 | 1 | 208 | 1 |
| 1 | 170 | 1 | 172 | 1 | 22 | 1 | 126 | 1 | 150 | 1 | 188 | 1 |
| 1 | 170 | 1 | 172 | 1 | 16 | 1 | 126 | 1 | 150 | 1 | 188 | 1 |
| 0 | | | 0 | | | 0 | 10 | 1 | 128 | 0 | | 0 | 208 | 0 |
| 0 | | | 0 | | | 0 | 10 | 1 | 124 | 0 | | 0 | 200 | 0 |
| 1 | 178 | 0 | 172 | 1 | 10 | 1 | 124 | 1 | 150 | 1 | 188 | 1 |
| 1 | 170 | 0 | 172 | 1 | 10 | 1 | 126 | 1 | 146 | 1 | 216 | 1 |
| 1 | 170 | 1 | 160 | 1 | 18 | 0 | 124 | 1 | 158 | 1 | 188 | 1 |
| 1 | 170 | 1 | 174 | 1 | 10 | 0 | 124 | 1 | 150 | 1 | 192 | 1 |
| 1 | 170 | 1 | 174 | 0 | 18 | 1 | 124 | 1 | 150 | 1 | 192 | 0 |
| 1 | 186 | 1 | 172 | 0 | 18 | 1 | 124 | 1 | 146 | 1 | 188 | 0 |
| 1 | 170 | 1 | 174 | 1 | 18 | 1 | 124 | 1 | 150 | 1 | 192 | 1 |
| 1 | 178 | 1 | 172 | 1 | 10 | 1 | 124 | 1 | 162 | 1 | 188 | 1 |

*FIG. 8K*

Affected haplotypes

| ca219 | | 1105 | | ca209 | | ca202 | | 1146 | | 166d05 | | 476 | |
|---|---|---|---|---|---|---|---|---|---|---|---|---|---|
| 243 | 0 | 103 | 0 | 177 | 0 | 196 | 0 | 274 | 0 | 308 | 1 | 271 | 1 |
| 241 | 0 | 85 | 0 | 173 | 0 | 190 | 0 | 270 | 0 | 312 | 1 | 265 | 1 |
| 235 | 1 | 99 | 1 | 181 | 1 | 196 | 1 | 274 | 1 | 308 | 1 | 271 | 0 |
| 235 | 1 | 101 | 1 | 181 | 1 | 196 | 1 | 272 | 1 | 308 | 1 | 267 | 0 |
| 241 | 1 | 85 | 1 | 177 | 0 | 192 | 1 | 270 | 1 | 316 | 0 | 269 | 0 |
| 245 | 1 | 85 | 1 | 173 | 0 | 184 | 1 | 274 | 1 | 308 | 0 | 265 | 0 |
| 241 | 1 | 99 | 1 | 177 | 1 | | 0 | 274 | 0 | 308 | 1 | 267 | 1 |
| 241 | 1 | 105 | 1 | 173 | 1 | | 0 | 270 | 0 | 300 | 1 | 271 | 1 |
| 241 | 0 | 103 | 1 | 181 | 0 | 190 | 1 | 274 | 1 | 312 | 1 | 271 | 1 |
| 235 | 0 | 97 | 1 | 173 | 0 | 198 | 1 | 270 | 1 | 300 | 1 | 267 | 1 |
| 241 | 1 | 99 | 1 | 177 | 0 | 182 | 1 | 274 | 1 | 308 | 1 | 271 | 1 |
| 241 | 1 | 85 | 1 | 173 | 0 | 196 | 1 | 274 | 1 | 300 | 1 | 271 | 1 |
| 245 | 1 | 85 | 1 | 177 | 1 | 182 | 1 | 274 | 1 | 312 | 1 | 273 | 1 |
| 245 | 1 | 85 | 1 | 177 | 1 | 182 | 1 | 274 | 1 | 312 | 1 | 267 | 1 |
| 241 | 1 | 85 | 1 | 175 | 1 | 196 | 1 | 274 | 1 | 320 | 1 | 261 | 1 |
| 241 | 1 | 101 | 1 | 173 | 1 | 196 | 1 | 270 | 1 | 304 | 1 | 267 | 1 |
| 241 | 0 | 85 | 1 | 173 | 1 | 186 | 1 | 270 | 1 | 316 | 1 | 269 | 1 |
| 239 | 0 | 85 | 1 | 173 | 1 | 182 | 1 | 270 | 1 | 312 | 1 | 273 | 1 |
| 235 | 1 | 101 | 1 | 181 | 1 | 184 | 1 | 274 | 1 | 324 | 1 | 269 | 1 |
| 235 | 1 | 101 | 1 | 181 | 1 | 184 | 1 | 274 | 1 | 324 | 1 | 269 | 1 |
| 241 | 1 | 85 | 1 | 173 | 1 | 190 | 1 | 274 | 0 | 316 | 1 | 271 | 1 |
| 245 | 1 | 101 | 1 | 175 | 1 | 196 | 1 | 270 | 0 | 308 | 1 | 271 | 1 |
| 241 | 1 | 85 | 1 | 173 | 1 | 196 | 0 | 270 | 1 | 316 | 1 | 267 | 1 |
| 243 | 1 | 85 | 1 | 173 | 1 | 192 | 0 | 274 | 1 | 308 | 1 | 267 | 1 |
| 241 | 0 | 99 | 0 | 181 | 0 | 196 | 0 | 274 | 1 | 312 | 1 | 271 | 0 |
| 235 | 0 | 85 | 0 | 173 | 0 | 192 | 0 | 274 | 1 | 312 | 1 | 267 | 0 |
| 241 | 1 | 101 | 0 | 173 | 1 | 196 | 1 | 270 | 1 | 304 | 1 | 267 | 1 |
| 241 | 1 | 85 | 0 | 173 | 1 | 194 | 1 | 270 | 1 | 312 | 1 | 267 | 1 |
| 241 | 1 | 99 | 1 | 173 | 1 | 192 | 1 | 274 | 1 | 312 | 1 | 271 | 1 |
| 225 | 1 | 83 | 1 | 173 | 1 | 192 | 1 | 270 | 1 | 308 | 1 | 269 | 1 |
| 241 | 1 | 85 | 1 | 173 | 1 | 182 | 1 | 274 | 0 | 312 | 0 | 271 | 1 |
| 241 | 1 | 85 | 1 | 181 | 1 | 182 | 1 | 270 | 0 | 308 | 0 | 269 | 1 |
| 245 | 1 | 103 | 1 | 177 | 1 | 196 | 0 | 270 | 1 | 304 | 1 | 267 | 1 |
| 241 | 1 | 105 | 1 | 173 | 1 | 192 | 0 | 274 | 1 | 316 | 1 | 271 | 1 |

*FIG. 8L*

| 18p | PAN | MAN | ca212 | | 1140 | | 59 | | ca231 | | ta201 | |
|---|---|---|---|---|---|---|---|---|---|---|---|---|
| 587 | 580 | 582 | 202 | 1 | 256 | 1 | 158 | 1 | 186 | 1 | 248 | |
| 587 | | | 202 | 1 | 268 | 1 | 154 | 1 | 186 | 1 | 244 | |
| 361 | 1 | 360 | 204 | 0 | 270 | 1 | 158 | 1 | 186 | 1 | 244 | |
| 361 | | | 202 | 0 | 276 | 1 | 148 | 1 | 186 | 1 | 236 | |
| 368 | 0 | 0 | 204 | 1 | 268 | 1 | 164 | 1 | 186 | 1 | 242 | |
| 368 | | | 202 | 1 | 256 | 1 | 154 | 1 | 186 | 1 | 230 | |
| 374 | 1 | 2 | 200 | 1 | 268 | 1 | 154 | 1 | 186 | 1 | 230 | |
| 374 | | | 200 | 1 | 268 | 1 | 154 | 1 | 186 | 1 | 230 | |
| 399 | 0 | 0 | 202 | 1 | 268 | 1 | 148 | 1 | 184 | 1 | | |
| 399 | | | 204 | 1 | 272 | 1 | 158 | 1 | 186 | 1 | | |
| 411 | 1 | 2 | 216 | 0 | 270 | 0 | 164 | 0 | 184 | 0 | 252 | |
| 411 | | | 202 | 0 | 268 | 0 | 154 | 0 | 186 | 0 | 230 | |
| 413 | 414 | 412 | 200 | 1 | 268 | 1 | 158 | 1 | 186 | 1 | 230 | |
| 413 | | | 202 | 1 | 280 | 1 | 148 | 1 | 186 | 1 | 244 | |
| 236 | 697 | 698 | 216 | 1 | 268 | 1 | 158 | 1 | 186 | 1 | 220 | |
| 236 | | | 216 | 1 | 268 | 1 | 158 | 1 | 186 | 1 | 220 | |
| 421 | 0 | 0 | 200 | 1 | 268 | 1 | 148 | 1 | 184 | 0 | 252 | |
| 421 | | | 202 | 1 | 268 | 1 | 152 | 1 | 186 | 0 | 242 | |
| 424 | 1 | 2 | 200 | 1 | 268 | 1 | 158 | 0 | 194 | 0 | 220 | |
| 424 | | | 200 | 1 | 268 | 1 | 154 | 0 | 186 | 0 | 232 | |
| 452 | 1 | 2 | 202 | 0 | 256 | 0 | 148 | 0 | 184 | 1 | 252 | |
| 452 | | | 200 | 0 | 268 | 0 | 154 | 0 | 184 | 1 | 250 | |
| 473 | 1 | 472 | 202 | 1 | 268 | 1 | 162 | 1 | 186 | 1 | 246 | |
| 473 | | | 218 | 1 | 268 | 1 | 148 | 1 | 186 | 1 | 244 | |
| 484 | 482 | 2 | 200 | 1 | 276 | 1 | 148 | 1 | 182 | 0 | 246 | |
| 484 | | | 206 | 1 | 256 | 1 | 154 | 1 | 186 | 0 | 244 | |
| 487 | 1 | 486 | 200 | 1 | 268 | 1 | 158 | 1 | 190 | 0 | 248 | |
| 487 | | | 202 | 1 | 278 | 1 | 148 | 1 | 186 | 0 | 246 | |
| 331 | 1 | 476 | 202 | 0 | 268 | 1 | 154 | 1 | 186 | 1 | 234 | |
| 331 | | | 200 | 0 | 268 | 1 | 154 | 1 | 186 | 1 | 230 | |
| 489 | 0 | 0 | 202 | 1 | 268 | 1 | 158 | 1 | 186 | 1 | 244 | |
| 489 | | | 200 | 1 | 268 | 1 | 148 | 1 | 202 | 1 | 220 | |
| 498 | 1 | 635 | 200 | 1 | 268 | 1 | 160 | 1 | 186 | 1 | 246 | |
| 498 | | | 200 | 1 | 268 | 1 | 164 | 1 | 186 | 1 | 246 | |

Affected haplotypes

*FIG. 8M*

| | at201 | | PD | ca225 | | w3442 | | ca213 | | ga201 | | ga203 | |
|---|---|---|---|---|---|---|---|---|---|---|---|---|---|
| 1 | 170 | 1 | 1 | 174 | 1 | 16 | 1 | 124 | 1 | 150 | 1 | 208 | 1 |
| 1 | 170 | 1 | 1 | 172 | 1 | 10 | 1 | 132 | 1 | 150 | 1 | 208 | 1 |
| 1 | 170 | 1 | 1 | 172 | 1 | 10 | 1 | 126 | 1 | 150 | 1 | 208 | 1 |
| 1 | 170 | 1 | 1 | 172 | 1 | 20 | 1 | 128 | 1 | 150 | 1 | 212 | 1 |
| 0 | 178 | 0 | 0 | 172 | 1 | 10 | 1 | 124 | 0 | 150 | 1 | 192 | 1 |
| 0 | 170 | 0 | 0 | 160 | 1 | 10 | 1 | 126 | 0 | 154 | 1 | 212 | 1 |
| 1 | 178 | 1 | 1 | 174 | 0 | 10 | 1 | 126 | 0 | 150 | 0 | 188 | 0 |
| 1 | 178 | 1 | 1 | 160 | 0 | 10 | 1 | 124 | 0 | 142 | 0 | 212 | 0 |
| 0 | 170 | 1 | 1 | 174 | 0 | 16 | 1 | 124 | 1 | 142 | 1 | 188 | 1 |
| 0 | 178 | 1 | 1 | 172 | 0 | 18 | 1 | 126 | 1 | 150 | 1 | 200 | 1 |
| 0 | 170 | 0 | 0 | 174 | 0 | 18 | 0 | 124 | 1 | 150 | 0 | 188 | 1 |
| 0 | 178 | 0 | 0 | 160 | 0 | 10 | 0 | 124 | 1 | 142 | 0 | 188 | 1 |
| 1 | 178 | 1 | 1 | 178 | 1 | 18 | 1 | 112 | 1 | 150 | 1 | 188 | 1 |
| 1 | 170 | 1 | 1 | 176 | 1 | 24 | 1 | 126 | 1 | 154 | 1 | 188 | 1 |
| 1 | 170 | 1 | 1 | 172 | 1 | 20 | 1 | 124 | 1 | 150 | 1 | 204 | 1 |
| 1 | 170 | 1 | 1 | 172 | 1 | 20 | 1 | 124 | 1 | 150 | 1 | 204 | 1 |
| 1 | 170 | 1 | 1 | 174 | 1 | 10 | 1 | 126 | 1 | 150 | 1 | 188 | 1 |
| 1 | 190 | 1 | 1 | 172 | 1 | 10 | 1 | 126 | 1 | 150 | 1 | 188 | 1 |
| 0 | 170 | 0 | 0 | 178 | 0 | 24 | 0 | 128 | 0 | 150 | 0 | 208 | 0 |
| 0 | 178 | 0 | 0 | 160 | 0 | 18 | 0 | 112 | 0 | 146 | 0 | 192 | 0 |
| 0 | 170 | 1 | 1 | 174 | 0 | 16 | 0 | 124 | 1 | 158 | 0 | 188 | 1 |
| 0 | 170 | 1 | 1 | 160 | 0 | 10 | 0 | 124 | 1 | 150 | 0 | 188 | 1 |
| 1 | 170 | 1 | 1 | 180 | 1 | 22 | 0 | 126 | 1 | 150 | 1 | 212 | 1 |
| 1 | 170 | 1 | 1 | 160 | 1 | 10 | 0 | 124 | 1 | 146 | 1 | 188 | 1 |
| 1 | 170 | 1 | 1 | 174 | 1 | 14 | 1 | 124 | 1 | 150 | 1 | 188 | 1 |
| 1 | 170 | 1 | 1 | 174 | 1 | 10 | 1 | 126 | 1 | 150 | 1 | 212 | 1 |
| 1 | 170 | 1 | 1 | 174 | 1 | 12 | 0 | 126 | 1 | 158 | 1 | 192 | 1 |
| 1 | 182 | 1 | 1 | 180 | 1 | 10 | 0 | 112 | 1 | 150 | 1 | 208 | 1 |
| 1 | 178 | 0 | 0 | 172 | 1 | 24 | 1 | 126 | 0 | 158 | 0 | 212 | 0 |
| 1 | 170 | 0 | 0 | 172 | 1 | 10 | 1 | 112 | 0 | 150 | 0 | 188 | 0 |
| 1 | 170 | 1 | 1 | 172 | 1 | 10 | 1 | 124 | 1 | 150 | 1 | 204 | 1 |
| 1 | 178 | 1 | 1 | 172 | 1 | 10 | 1 | 132 | 1 | 162 | 1 | 208 | 1 |
| 1 | 170 | 1 | 1 | 172 | 1 | 14 | 1 | 122 | 1 | 150 | 1 | 208 | 1 |
| 1 | 170 | 1 | 1 | 172 | 1 | 18 | 1 | 112 | 1 | 150 | 1 | 188 | 1 |

*FIG. 8N*

Affected haplotypes

| ca219 | | 1105 | | ca209 | | ca202 | | 1146 | | 166d05 | | 476 | |
|---|---|---|---|---|---|---|---|---|---|---|---|---|---|
|  |  | 0 | 85 | 1 | 173 | 1 | 190 | 1 | 274 | 1 | 312 | 1 | 271 | 1 |
|  |  | 0 | 101 | 1 | 181 | 1 | 198 | 1 | 272 | 1 | 312 | 1 | 263 | 1 |
| 241 | 1 | 99 | 1 | 177 | 0 | 198 | 1 | 274 | 1 | 312 | 1 | 271 | 1 |
| 241 | 1 | 101 | 1 | 173 | 0 | 196 | 1 | 276 | 1 | 304 | 1 | 265 | 1 |
| 241 | 1 | 85 | 1 | 173 | 1 | 196 | 1 | 270 | 1 | 304 | 1 | 271 | 1 |
| 241 | 1 | 85 | 1 | 173 | 1 | 190 | 1 | 270 | 1 | 312 | 1 | 271 | 1 |
| 241 | 1 | 85 | 0 | 173 | 1 | 200 | 0 | 270 | 1 | 312 | 0 | 271 | 1 |
| 241 | 1 | 101 | 0 | 173 | 1 | 186 | 0 | 270 | 1 | 304 | 0 | 271 | 1 |
| 243 | 1 | 85 | 1 | 173 | 1 | 200 | 1 | 274 | 1 | 312 | 1 | 271 | 1 |
| 235 | 1 | 95 | 1 | 181 | 1 | 196 | 1 | 274 | 1 | 312 | 1 | 271 | 1 |
| 241 | 0 | 85 | 1 | 173 | 1 | 200 | 1 | 274 | 1 | 312 | 0 | 271 | 1 |
| 243 | 0 | 85 | 1 | 173 | 1 | 200 | 1 | 274 | 1 | 308 | 0 | 271 | 1 |
| 241 | 1 | 85 | 1 | 173 | 1 | 194 | 1 | 274 | 1 | 300 | 1 | 275 | 1 |
| 241 | 1 | 85 | 1 | 181 | 1 | 196 | 1 | 274 | 1 | 300 | 1 | 271 | 1 |
| 243 | 1 | 103 | 1 | 175 | 1 | 198 | 1 | 274 | 1 | 300 | 1 | 271 | 1 |
| 243 | 1 | 103 | 1 | 175 | 1 | 196 | 1 | 274 | 1 | 308 | 1 | 271 | 1 |
| 235 | 1 | 97 | 1 | 181 | 1 | 196 | 1 | 274 | 1 | 300 | 1 | 271 | 1 |
| 235 | 1 | 99 | 1 | 181 | 1 | 192 | 1 | 270 | 1 | 312 | 1 | 267 | 1 |
| 241 | 0 | 101 | 0 | 181 | 0 | 194 | 0 | 274 | 0 | 308 | 0 | 271 | 0 |
| 235 | 0 | 85 | 0 | 173 | 0 | 182 | 0 | 272 | 0 | 300 | 0 | 267 | 0 |
| 243 | 0 | 103 | 0 | 173 | 1 | 196 | 1 | 274 | 1 | 308 | 0 | 269 | 0 |
| 241 | 0 | 85 | 0 | 173 | 1 | 196 | 1 | 274 | 1 | 304 | 0 | 267 | 0 |
| 241 | 1 | 87 | 1 | 177 | 0 | 196 | 1 | 274 | 0 | 312 | 1 | 271 | 1 |
| 241 | 1 | 85 | 1 | 173 | 0 | 194 | 1 | 270 | 1 | 300 | 1 | 275 | 1 |
| 241 | 1 | 105 | 1 | 173 | 1 | 196 | 1 | 274 | 0 | 312 | 1 | 271 | 0 |
| 241 | 1 | 85 | 1 | 173 | 1 | 192 | 1 | 270 | 0 | 312 | 1 | 267 | 0 |
| 243 | 0 | 85 | 1 | 173 | 1 | 198 | 1 | 270 | 1 | 304 | 1 | 271 | 1 |
| 241 | 0 | 85 | 1 | 173 | 1 | 196 | 1 | 274 | 1 | 312 | 1 | 271 | 1 |
| 241 | 1 | 85 | 1 | 173 | 1 | 196 | 1 | 274 | 1 | 308 | 1 | 271 | 0 |
| 241 | 1 | 85 | 1 | 173 | 1 | 182 | 1 | 274 | 1 | 320 | 1 | 265 | 0 |
| 245 | 0 | 85 | 1 | 177 | 0 | 198 | 1 | 274 | 1 | 304 | 1 | 271 | 0 |
| 241 | 0 | 85 | 1 | 173 | 1 | 194 | 1 | 274 | 1 | 312 | 1 | 267 | 0 |
| 241 | 1 | 103 | 1 | 177 | 1 | 196 | 1 | 270 | 1 | 316 | 1 | 267 | 1 |
| 235 | 1 | 99 | 1 | 181 | 1 | 192 | 1 | 270 | 1 | 312 | 1 | 271 | 1 |

*FIG. 80*

| 18p | PAN | MAN | ca212 | | 1140 | | 59 | | ca231 | | ta201 | |
|---|---|---|---|---|---|---|---|---|---|---|---|---|
| 566 | 0 | 0 | 216 | 1 | 268 | 1 | 148 | 1 | 202 | 1 | 220 | |
| 566 | | | 202 | 1 | 268 | 1 | 154 | 1 | 186 | 1 | 230 | |
| 514 | 1 | 2 | 202 | 0 | 268 | 1 | 154 | 1 | 186 | 0 | 230 | |
| 514 | | | 200 | 0 | 268 | 1 | 154 | 1 | 184 | 0 | 230 | |
| 536 | 1 | 633 | 202 | 1 | 270 | 0 | 148 | 1 | 184 | 1 | 254 | |
| 536 | | | 200 | 1 | 268 | 0 | 154 | 1 | 186 | 1 | 252 | |
| 605 | 1 | 2 | 216 | 0 | 268 | 1 | 158 | 0 | 198 | 0 | 244 | |
| 605 | | | 200 | 0 | 268 | 1 | 150 | 0 | 186 | 0 | 220 | |
| 540 | 539 | 562 | 200 | 1 | 268 | 1 | 154 | 1 | 186 | 1 | 230 | |
| 540 | | | 216 | 1 | 268 | 1 | 148 | 1 | 186 | 1 | 230 | |
| 684 | 1 | 730 | 202 | 0 | 268 | 1 | 158 | 1 | 186 | 1 | 232 | |
| 684 | | | 200 | 0 | 268 | 1 | 154 | 1 | 186 | 1 | 244 | |
| 608 | 1 | 2 | 206 | 0 | 268 | 1 | 156 | 0 | 192 | 0 | 244 | |
| 608 | | | 202 | 0 | 268 | 1 | 154 | 0 | 186 | 0 | 220 | |
| 637 | 1 | 638 | 216 | 1 | 268 | 1 | 162 | 0 | 186 | 1 | 250 | |
| 637 | | | 200 | 1 | 268 | 1 | 154 | 0 | 186 | 1 | 230 | |
| 649 | 647 | 646 | 200 | 1 | 268 | 1 | 154 | 1 | 186 | 1 | 230 | |
| 649 | | | 200 | 1 | 270 | 1 | 162 | 1 | 184 | 1 | 250 | |
| 653 | 1 | 652 | 200 | 1 | 280 | 0 | 160 | 0 | 184 | 1 | 230 | |
| 653 | | | 200 | 1 | 268 | 0 | 148 | 0 | 186 | 1 | 230 | |
| 491 | 1 | 2 | 204 | 0 | 268 | 1 | 158 | 0 | 194 | 0 | 256 | |
| 491 | | | 202 | 0 | 268 | 1 | 148 | 0 | 184 | 0 | 230 | |
| 493 | 1 | 2 | 202 | 0 | 282 | 0 | 158 | 0 | 186 | 1 | 242 | |
| 493 | | | 200 | 0 | 268 | 0 | 156 | 0 | 186 | 1 | 242 | |
| 506 | 1 | 2 | | 0 | | 0 | | 0 | | 0 | | |
| 506 | | | | 0 | | 0 | | 0 | | 0 | | |
| 661 | 660 | 662 | 200 | 1 | 278 | 1 | 156 | 1 | 198 | 1 | 220 | |
| 661 | | | 200 | 1 | 268 | 1 | 148 | 1 | 184 | 1 | 250 | |
| 667 | 666 | 668 | 202 | 1 | 268 | 1 | 154 | 1 | 186 | 1 | 214 | |
| 667 | | | 202 | 1 | 268 | 1 | 162 | 1 | 186 | 1 | 246 | |
| 669 | 670 | 671 | 202 | 1 | 268 | 1 | 162 | 1 | 186 | 1 | 258 | |
| 669 | | | 200 | 1 | 268 | 1 | 154 | 1 | 186 | 1 | 244 | |
| 676 | 1 | 678 | 202 | 0 | 268 | 1 | 158 | 1 | 190 | 1 | 244 | |
| 676 | | | 200 | 0 | 280 | 1 | 148 | 1 | 184 | 1 | 252 | |

Affected haplotypes

*FIG. 8P*

| | at201 | PD | ca225 | | w3442 | | ca213 | | ga201 | | ga203 | |
|---|---|---|---|---|---|---|---|---|---|---|---|---|
| 0 | 178 | 1 | 174 | 1 | 10 | 1 | 124 | 1 | 150 | 1 | 212 | 1 |
| 0 | 178 | 1 | 172 | 1 | 10 | 1 | 128 | 1 | 150 | 1 | 208 | 1 |
| 1 | 178 | 1 | 172 | 0 | 10 | 1 | 124 | 1 | 154 | 0 | 192 | 1 |
| 1 | 178 | 1 | 168 | 0 | 10 | 1 | 124 | 1 | 146 | 0 | 192 | 1 |
| 1 | 170 | 1 | 168 | 0 | 16 | 1 | 132 | 0 | 162 | 1 | 212 | 0 |
| 1 | 178 | 1 | 172 | 0 | 24 | 1 | 124 | 0 | 154 | 1 | 188 | 0 |
| 0 | 170 | 0 | 172 | 1 | 16 | 0 | 124 | 1 | 158 | 0 | 200 | 0 |
| 0 | 178 | 0 | 172 | 1 | 10 | 0 | 124 | 1 | 150 | 0 | 188 | 0 |
| 1 | 178 | 1 | 172 | 1 | 10 | 1 | 124 | 1 | 150 | 1 | 216 | 1 |
| 1 | 194 | 1 | 172 | 1 | 22 | 1 | 112 | 1 | 154 | 1 | 212 | 1 |
| 1 | 178 | 1 | 160 | 1 | 24 | 1 | 112 | 1 | 150 | 1 | 212 | 1 |
| 1 | 170 | 1 | 160 | 1 | 10 | 1 | 126 | 1 | 150 | 1 | 188 | 1 |
| 0 | 170 | 1 | 178 | 0 | 22 | 0 | 126 | 1 | 150 | 1 | 204 | 0 |
| 0 | 170 | 1 | 174 | 0 | 10 | 0 | 126 | 1 | 150 | 1 | 188 | 0 |
| 1 | 182 | 1 | 172 | 1 | 10 | 1 | 124 | 1 | 142 | 0 | 208 | 1 |
| 1 | 178 | 1 | 172 | 1 | 10 | 1 | 124 | 1 | 150 | 0 | 212 | 1 |
| 1 | 178 | 1 | 172 | 1 | 10 | 1 | 124 | 1 | 150 | 1 | 188 | 1 |
| 1 | 170 | 1 | 180 | 1 | 10 | 1 | 112 | 1 | 154 | 1 | 188 | 1 |
| 1 | 178 | 1 | 184 | 1 | 20 | 1 | 128 | 1 | 154 | 1 | | 0 |
| 1 | 178 | 1 | 168 | 1 | 22 | 1 | 112 | 1 | 150 | 1 | | 0 |
| 0 | 178 | 0 | 180 | 0 | 22 | 0 | 124 | 1 | 158 | 0 | 204 | 0 |
| 0 | 170 | 0 | 174 | 0 | 10 | 0 | 124 | 1 | 154 | 0 | 188 | 0 |
| 1 | 170 | 1 | 174 | 0 | 16 | 0 | 124 | 1 | 158 | 0 | 212 | 0 |
| 1 | 170 | 1 | 172 | 0 | 14 | 0 | 124 | 1 | 150 | 0 | 204 | 0 |
| 0 | | 0 | | 0 | | 0 | | 0 | 150 | 1 | | 0 |
| 0 | | 0 | | 0 | | 0 | | 0 | 150 | 1 | | 0 |
| 1 | 170 | 1 | 174 | 1 | 20 | 1 | 126 | 1 | 154 | 1 | 204 | 1 |
| 1 | 186 | 1 | 174 | 1 | 18 | 1 | 120 | 1 | 150 | 1 | 188 | 1 |
| 1 | 170 | 1 | 160 | 1 | 22 | 1 | 124 | 1 | 146 | 1 | 212 | 1 |
| 1 | 178 | 1 | 172 | 1 | 18 | 1 | 112 | 1 | 158 | 1 | 188 | 1 |
| 1 | 186 | 1 | 174 | 1 | 18 | 1 | 126 | 1 | 150 | 1 | 188 | 1 |
| 1 | 170 | 1 | 160 | 1 | 10 | 1 | 126 | 1 | 150 | 1 | 188 | 1 |
| 1 | 178 | 1 | 172 | 1 | 16 | 1 | 126 | 1 | 158 | 1 | 188 | 1 |
| 1 | 178 | 1 | 172 | 1 | 22 | 1 | 126 | 1 | 150 | 1 | 216 | 1 |

FIG. 8Q

Affected haplotypes

| ca219 | | 1105 | | ca209 | | ca202 | | 1146 | | 166d05 | | 476 | |
|---|---|---|---|---|---|---|---|---|---|---|---|---|---|
| 245 | 1 | 105 | 0 | 177 | 1 | 196 | 1 | 274 | 1 | 300 | 1 | 267 | 1 |
| 245 | 1 | 85 | 0 | 177 | 1 | 198 | 1 | 274 | 1 | 320 | 1 | 271 | 1 |
| 241 | 1 | 97 | 0 | 177 | 0 | 196 | 1 | 274 | 0 | 304 | 0 | 271 | 1 |
| 241 | 1 | 85 | 0 | 173 | 0 | 196 | 1 | 272 | 0 | 300 | 0 | 271 | 1 |
| 241 | 1 | 99 | 0 | 177 | 0 | 196 | 1 | 274 | 1 | 312 | 1 | 271 | 1 |
| 241 | 1 | 85 | 0 | 173 | 0 | 182 | 1 | 274 | 1 | 312 | 1 | 271 | 1 |
| 243 | 0 | 85 | 1 | 173 | 1 | 200 | 0 | 274 | 1 | 308 | 1 | 271 | 1 |
| 235 | 0 | 85 | 1 | 173 | 1 | 194 | 0 | 274 | 1 | 308 | 1 | 271 | 1 |
| 241 | 1 | 85 | 1 | 173 | 1 | 190 | 1 | 274 | 0 | 312 | 1 | 267 | 1 |
| 235 | 1 | 85 | 1 | 173 | 1 | 196 | 1 | 272 | 0 | 316 | 1 | 267 | 1 |
| 241 | 0 | 85 | 1 | 181 | 0 | 196 | 1 | 274 | 0 | 312 | 1 | 269 | 1 |
| 235 | 0 | 101 | 1 | 173 | 0 | 196 | 1 | 272 | 0 | 300 | 1 | 271 | 1 |
| 245 | 0 | 101 | 0 | 173 | 0 | 182 | 0 | 274 | 1 | 312 | 1 | 273 | 0 |
| 241 | 0 | 85 | 0 | 177 | 0 | 190 | 0 | 274 | 1 | 312 | 1 | 267 | 0 |
| 239 | 1 | 85 | 1 | 173 | 1 | 190 | 1 | 270 | 1 | 300 | 1 | 271 | 1 |
| 241 | 1 | 85 | 1 | 173 | 1 | 198 | 1 | 274 | 1 | 304 | 1 | 271 | 1 |
| 241 | 0 | 85 | 1 | 173 | 1 | 198 | 1 | 270 | 1 | 304 | 1 | 271 | 1 |
| 243 | 0 | 85 | 1 | 173 | 1 | 182 | 1 | 274 | 1 | 312 | 1 | 269 | 1 |
| 245 | 1 | 85 | 1 | 179 | 1 | 196 | 1 | 270 | 1 | 308 | 1 | 271 | 1 |
| 241 | 1 | 85 | 1 | 173 | 1 | 196 | 1 | 270 | 1 | 304 | 1 | 265 | 1 |
| 241 | 0 | 103 | 0 | 173 | 1 | 198 | 0 | 274 | 1 | 308 | 1 | 269 | 0 |
| 235 | 0 | 81 | 0 | 173 | 1 | 196 | 0 | 274 | 1 | 308 | 1 | 265 | 0 |
| 241 | 1 | 103 | 0 | 177 | 0 | 196 | 0 | 270 | 1 | 308 | 0 | 271 | 0 |
| 241 | 1 | 85 | 0 | 173 | 0 | 190 | 0 | 270 | 1 | 300 | 0 | 269 | 0 |
| 245 | 0 | | 0 | | 0 | | 0 | | 0 | | 0 | | 0 |
| 241 | 0 | | 0 | | 0 | | 0 | | 0 | | 0 | | 0 |
| 235 | 1 | 81 | 1 | 173 | 1 | 196 | 1 | 276 | 1 | 300 | 1 | 271 | 1 |
| 241 | 1 | 85 | 1 | 173 | 1 | 196 | 1 | 274 | 1 | 308 | 1 | 265 | 1 |
| 245 | 1 | 103 | 1 | 177 | 1 | 196 | 1 | 270 | 1 | 308 | 1 | 271 | 1 |
| 235 | 1 | 97 | 1 | 181 | 1 | 192 | 1 | 274 | 1 | 312 | 1 | 271 | 1 |
| 241 | 1 | 101 | 0 | 173 | 1 | 192 | 1 | 274 | 1 | 316 | 1 | 271 | 1 |
| 235 | 1 | 85 | 0 | 181 | 1 | 190 | 1 | 270 | 1 | 312 | 1 | 271 | 1 |
| 235 | 1 | 97 | 1 | 181 | 1 | 198 | 1 | 274 | 1 | 312 | 0 | 271 | 1 |
| 243 | 1 | 103 | 1 | 173 | 1 | 182 | 1 | 274 | 1 | 308 | 0 | 273 | 1 |

*FIG. 8R*

Affected haplotypes

| 1Bp | PAN | MAN | ca212 | 1140 | | 59 | | ca231 | | ta201 | | dt201 | | PD ca225 | | w3442 | | ca213 | | ga201 | | ga203 | |
|---|---|---|---|---|---|---|---|---|---|---|---|---|---|---|---|---|---|---|---|---|---|---|---|
| 681 | 1 | 2 | 202 | 0 | 256 | 0 | 162 | 0 | 186 | 1 | 260 | 0 | 186 | 0 | 174 | 0 | 18 | 0 | 126 | 0 | 150 | 0 | 192 |
| 681 | | | 200 | 0 | 268 | 0 | 154 | 0 | 186 | 1 | 230 | 0 | 178 | 0 | 172 | 0 | 10 | 0 | 124 | 0 | 150 | 1 | 188 |
| 351 | 354 | 2 | 202 | 1 | 268 | 1 | 154 | 1 | 186 | 1 | 230 | 1 | 178 | 1 | 172 | 1 | 16 | 1 | 126 | 1 | 150 | 1 | 188 |
| 351 | | | 216 | 1 | 268 | 1 | 156 | 1 | 186 | 1 | 244 | 1 | 186 | 1 | 174 | 1 | 24 | 1 | 124 | 1 | 150 | 1 | 208 |
| 355 | 1 | 2 | 216 | 0 | 272 | 0 | 158 | 0 | 190 | 0 | 248 | 0 | 170 | 0 | 172 | 1 | 18 | 0 | 126 | 0 | 158 | 0 | 188 |
| 355 | | | 204 | 0 | 268 | 0 | 152 | 0 | 186 | 0 | 244 | 0 | 178 | 0 | 172 | 1 | 10 | 0 | 124 | 0 | 150 | 0 | 188 |

FIG. 8S

Affected haplotypes

| ca219 | | 1105 | | ca209 | | ca202 | | 1146 | | 166d05 | | 476 | |
|---|---|---|---|---|---|---|---|---|---|---|---|---|---|
| 241 | 1 | 103 | 0 | 177 | 0 | 190 | 0 | 270 | 0 | 304 | 0 | 271 | 1 |
| 241 | 1 | 85 | 0 | 173 | 0 | 196 | 0 | 274 | 0 | 312 | 0 | 271 | 1 |
| 241 | 1 | 101 | 1 | 173 | 1 | 192 | 1 | 274 | 1 | 312 | 1 | 271 | 0 |
| 245 | 1 | 105 | 1 | 177 | 1 | 194 | 1 | 274 | 1 | 320 | 1 | 267 | 0 |
| 241 | 1 | 103 | 0 | 177 | 0 | 196 | 1 | 274 | 0 | 316 | 0 | 267 | 1 |
| 241 | 1 | 85 | 0 | 173 | 0 | 196 | 1 | 270 | 0 | 304 | 0 | 267 | 1 |

*FIG. 8T* nontransmitted chromosomes

| ERSN | KID | sava5 | | ca211 | | ca212 | | 1140 | | 59 | | ca231 |
|---|---|---|---|---|---|---|---|---|---|---|---|---|
| 279 | 200 | 235 | 1 | 193 | 1 | 216 | 1 | 268 | 1 | 148 | 1 | 186 |
| 280 | 200 | 233 | 1 | 205 | 1 | 202 | 1 | 278 | 1 | 148 | 1 | 184 |
| 349 | 204 | 235 | 1 | 197 | 1 | 202 | 1 | 268 | 1 | 156 | 1 | 184 |
| 309 | 204 | 235 | 1 | 195 | 1 | 202 | 1 | 268 | 1 | 148 | 1 | 186 |
| 277 | 207 | 227 | 1 | 205 | 1 | 200 | 1 | 268 | 1 | 148 | 1 | 184 |
| 278 | 207 | 227 | 1 | 195 | 1 | 200 | 1 | 268 | 1 | 158 | 1 | 186 |
| 459 | 214 | 233 | 1 | 197 | 1 | 200 | 1 | 268 | 1 | 152 | 1 | 184 |
| 460 | 214 | 233 | 1 | 203 | 1 | 216 | 1 | 280 | 1 | 158 | 1 | 184 |
| 270 | 215 | 235 | 1 | 193 | 1 | 200 | 1 | 268 | 1 | 154 | 0 | 188 |
| 259 | 216 | 231 | 1 | 193 | 1 | 200 | 1 | 268 | 0 | 150 | 1 | 184 |
| 272 | 218 | 233 | 1 | 195 | 1 | 204 | 1 | 268 | 1 | 150 | 1 | 186 |
| 273 | 218 | 235 | 1 | 193 | 1 | 200 | 1 | 256 | 1 | 154 | 1 | 186 |
| 267 | 220 | 233 | 1 | 205 | 1 | 200 | 0 | 268 | 1 | 158 | 1 | 186 |
| 264 | 225 | 227 | 1 | 201 | 1 | 200 | 1 | 268 | 1 | 150 | 1 | 186 |
| 260 | 228 | 229 | 1 | 197 | 1 | 200 | 1 | 268 | 1 | 164 | 1 | 186 |
| 257 | 229 | 227 | 1 | 207 | 1 | 200 | 1 | 256 | 0 | 160 | 1 | 186 |
| 298 | 231 | 233 | 1 | 193 | 1 | 200 | 1 | 280 | 1 | 158 | 1 | 186 |
| 299 | 231 | 229 | 1 | 207 | 1 | 200 | 1 | 268 | 1 | 148 | 1 | 202 |
| 310 | 232 | 233 | 1 | 205 | 1 | 202 | 1 | 268 | 1 | 148 | 1 | 204 |
| 261 | 234 | 233 | 1 | 189 | 1 | 206 | 1 | 272 | 1 | 154 | 1 | 186 |
| 697 | 236 | 235 | 1 | 197 | 1 | 200 | 1 | 268 | 1 | 154 | 1 | 186 |
| 698 | 236 | 233 | 1 | 195 | 1 | 202 | 1 | 278 | 1 | 148 | 1 | 184 |
| 456 | 238 | 235 | 1 | 199 | 1 | 216 | 1 | 268 | 1 | 160 | 1 | 184 |
| 457 | 238 | 233 | 1 | 197 | 1 | 200 | 1 | 268 | 1 | 160 | 1 | 186 |
| 312 | 239 | 227 | 1 | 197 | 1 | 202 | 1 | 268 | 1 | 148 | 1 | 184 |
| 342 | 241 | 227 | 1 | 193 | 1 | 202 | 1 | 256 | 1 | 158 | 1 | 184 |
| 347 | 243 | 229 | 1 | | 0 | 216 | 1 | 278 | 1 | 150 | 1 | 186 |
| 274 | 243 | 233 | 1 | 193 | 1 | 204 | 1 | 268 | 1 | 160 | 1 | 186 |
| 262 | 246 | 231 | 1 | 193 | 0 | 202 | 0 | 268 | 1 | 148 | 1 | 202 |
| 302 | 247 | 235 | 1 | 195 | 1 | 200 | 1 | 256 | 1 | 150 | 1 | 186 |
| 303 | 247 | 227 | 1 | 195 | 1 | 200 | 1 | 268 | 1 | 158 | 1 | 186 |
| 334 | 248 | 225 | 1 | 183 | 1 | 216 | 1 | 268 | 1 | 152 | 1 | 186 |
| 333 | 248 | 233 | 1 | 205 | 1 | 200 | 1 | 268 | 1 | 152 | 1 | 186 |
| 300 | 251 | 227 | 0 | 193 | 1 | 200 | 1 | 278 | 1 | 148 | 1 | 184 |

*FIG. 9A*

| | ta201 | | at201 | | ca225 | | w3442 | | ca213 | | ga201 | | ga203 | |
|---|---|---|---|---|---|---|---|---|---|---|---|---|---|---|
| 1 | 246 | 1 | 194 | 1 | 172 | 1 | 16 | 1 | 124 | 1 | 150 | 1 | 188 | 1 |
| 1 | 252 | 1 | 170 | 1 | 172 | 1 | 20 | 1 | 124 | 1 | 150 | 1 | 192 | 1 |
| 1 | 252 | 1 | 170 | 1 | 172 | 1 | 20 | 1 | 120 | 1 | 150 | 1 | 216 | 1 |
| 1 | 244 | 1 | 170 | 1 | 172 | 1 | 16 | 1 | 124 | 1 | 142 | 1 | 192 | 1 |
| 1 | 252 | 1 | 186 | 1 | 174 | 1 | 18 | 1 | 124 | 1 | 146 | 1 | 212 | 1 |
| 1 | 230 | 1 | 178 | 1 | 168 | 1 | 20 | 1 | 124 | 1 | 150 | 1 | 200 | 1 |
| 1 | 248 | 1 | 186 | 1 | 174 | 1 | 10 | 1 | 124 | 1 | 142 | 1 | 208 | 1 |
| 1 | 248 | 1 | 170 | 1 | 184 | 1 | 16 | 1 | 124 | 1 | 146 | 1 | 216 | 1 |
| 1 | 246 | 1 | 170 | 1 | 160 | 1 | 24 | 1 | 124 | 1 | 150 | 0 | 188 | 1 |
| 0 | 254 | 1 | 186 | 1 | 172 | 1 | 10 | 1 | 124 | 1 | 150 | 0 | 188 | 1 |
| 1 | 248 | 1 | 178 | 1 | 172 | 0 | 22 | 1 | 126 | 1 | 146 | 1 | 188 | 1 |
| 1 | 230 | 1 | 178 | 1 | 172 | 0 | 10 | 1 | 124 | 1 | 142 | 1 | 188 | 1 |
| 1 | 244 | 1 | 170 | 1 | 160 | 1 | 14 | 1 | 124 | 1 | 158 | 1 | 188 | 1 |
| 1 | 242 | 1 | 170 | 0 | 168 | 0 | 10 | 0 | 126 | 1 | 150 | 1 | 192 | 1 |
| 1 | 250 | 1 | 178 | 1 | 172 | 0 | 14 | 1 | 112 | 1 | 154 | 1 | 188 | 1 |
| 1 | 246 | 1 | 170 | 1 | 172 | 1 | 14 | 1 | 122 | 1 | 150 | 1 | 208 | 1 |
| 1 | 232 | 1 | 178 | 1 | 172 | 1 | 12 | 1 | 112 | 1 | 154 | 1 | 188 | 1 |
| 1 | 220 | 1 | 170 | 1 | 160 | 1 | 14 | 1 | 112 | 1 | 158 | 1 | 208 | 1 |
| 1 | 220 | 1 | 170 | 1 | 160 | 1 | 24 | 1 | 112 | 1 | 150 | 0 | 188 | 1 |
| 1 | 250 | 1 | 178 | 1 | 174 | 1 | 18 | 1 | 126 | 1 | 158 | 1 | 188 | 1 |
| 1 | 230 | 1 | 186 | 1 | 174 | 1 | 10 | 1 | 112 | 1 | 150 | 1 | 208 | 1 |
| 1 | 252 | 1 | 170 | 1 | 172 | 1 | 20 | 1 | 120 | 1 | 150 | 1 | 216 | 1 |
| 1 | 248 | 1 | 170 | 1 | 172 | 1 | 16 | 1 | 124 | 1 | 150 | 1 | 208 | 1 |
| 1 | 230 | 1 | 170 | 1 | 172 | 1 | 18 | 1 | 122 | 1 | 150 | 1 | 208 | 1 |
| 0 | 246 | 1 | 170 | 1 | 178 | 1 | 24 | 1 | 112 | 1 | 150 | 0 | 208 | 1 |
| 0 | 250 | 1 | 170 | 1 | 174 | 1 | 10 | 1 | 124 | 0 | 146 | 1 | 188 | 1 |
| 1 | 244 | 1 | 170 | 0 | 160 | 0 | 10 | 1 | 112 | 1 | 150 | 1 | 188 | 0 |
| 1 | 244 | 1 | 170 | 0 | 160 | 0 | 14 | 1 | 124 | 1 | 162 | 1 | 188 | 0 |
| 1 | 230 | 1 | 170 | 0 | 172 | 1 | 22 | 1 | 124 | 1 | 150 | 1 | 208 | 1 |
| 1 | 242 | 1 | 170 | 1 | 172 | 1 | 10 | 1 | 126 | 1 | 150 | 1 | 192 | 1 |
| 1 | 230 | 1 | 178 | 1 | 168 | 1 | 14 | 1 | 128 | 1 | 150 | 1 | 188 | 1 |
| 1 | 230 | 1 | 178 | 1 | 176 | 1 | 10 | 1 | 126 | 1 | 150 | 1 | 188 | 0 |
| 1 | 230 | 1 | 178 | 1 | 172 | 1 | 10 | 1 | 124 | 1 | 142 | 1 | 188 | 0 |
| 1 | 252 | 1 | 170 | 1 | 172 | 1 | 18 | 1 | 120 | 1 | 150 | 1 | 216 | 1 |

*FIG. 9B* nontransmitted chromosomes

| ca219 | | 1105 | | ca209 | | ca202 | | 1146 | | 166d05 | | 476 | |
|---|---|---|---|---|---|---|---|---|---|---|---|---|---|
| 241 | 1 | 103 | 1 | 173 | 1 | 186 | 1 | 274 | 1 | 316 | 1 | 269 | 1 |
| 241 | 1 | 85 | 1 | 173 | 1 | 182 | 1 | 270 | 1 | 316 | 1 | 263 | 1 |
| 243 | 1 | 85 | 1 | 177 | 1 | 192 | 1 | 270 | 0 | 312 | 1 | 265 | 1 |
| 241 | 1 | 85 | 1 | 173 | 1 | 192 | 1 | 270 | 0 | 312 | 1 | 267 | 1 |
| 241 | 1 | 85 | 1 | 173 | 1 | 198 | 1 | 274 | 1 | 308 | 1 | 271 | 1 |
| 245 | 1 | 101 | 1 | 175 | 1 | 196 | 1 | 274 | 1 | 316 | 1 | 267 | 1 |
| 245 | 1 | 101 | 1 | 177 | 1 | 190 | 1 | 274 | 1 | 312 | 1 | 267 | 1 |
| 241 | 1 | 85 | 1 | 173 | 1 | 202 | 1 | 270 | 1 | 312 | 1 | 269 | 1 |
| 235 | 1 | 95 | 1 | 181 | 1 | 190 | 0 | 274 | 1 | 308 | 1 | 267 | 0 |
| 241 | 1 | 85 | 1 | 173 | 1 | 196 | 1 | 274 | 1 | 304 | 1 | 267 | 0 |
| 235 | 1 | 103 | 1 | 181 | 1 | 196 | 1 | 274 | 1 | 312 | 1 | 265 | 1 |
| 235 | 1 | 99 | 1 | 181 | 1 | 196 | 1 | 274 | 1 | 304 | 1 | 271 | 1 |
| 241 | 1 | 85 | 0 | 173 | 1 | 192 | 1 | 270 | 1 | 312 | 1 | 271 | 1 |
| 241 | 1 | 85 | 0 | 173 | 0 | 196 | 1 | 270 | 1 | 304 | 1 | 271 | 1 |
| 235 | 1 | 93 | 1 | 181 | 1 | 196 | 1 | 274 | 1 | 308 | 1 | 269 | 0 |
| 241 | 1 | 103 | 1 | 177 | 1 | 196 | 1 | 270 | 1 | 316 | 1 | 267 | 1 |
| 235 | 1 | 97 | 1 | 181 | 1 | 198 | 1 | 274 | 1 | 300 | 1 | 271 | 1 |
| 245 | 1 | 85 | 1 | 177 | 1 | 192 | 1 | 270 | 1 | 300 | 1 | 271 | 1 |
| 241 | 1 | 85 | 0 | 173 | 0 | 196 | 1 | 274 | 1 | 308 | 1 | 271 | 1 |
| 235 | 1 | 95 | 1 | 181 | 1 | 198 | 0 | 274 | 1 | 300 | 1 | 267 | 1 |
| 241 | 1 | 85 | 1 | 173 | 1 | 196 | 1 | 274 | 1 | 300 | 1 | 267 | 1 |
| 243 | 1 | 85 | 1 | 177 | 1 | 192 | 1 | 270 | 1 | 312 | 1 | 265 | 1 |
| 241 | 0 | 99 | 1 | 177 | 1 | 198 | 1 | 270 | 1 | 312 | 1 | 263 | 1 |
| 241 | 0 | 97 | 1 | 177 | 1 | 196 | 1 | 274 | 1 | 304 | 1 | 275 | 1 |
| 245 | 1 | 85 | 0 | 177 | 1 | 196 | 1 | 272 | 1 | 308 | 1 | 263 | 0 |
| 235 | 0 | 99 | 1 | 173 | 0 | 196 | 1 | | 0 | 304 | 0 | | 0 |
| 235 | 1 | 101 | 1 | 181 | 1 | 194 | 1 | 274 | 1 | 308 | 1 | 267 | 1 |
| 241 | 1 | 85 | 1 | 177 | 1 | 196 | 1 | 274 | 1 | 304 | 1 | 271 | 1 |
| 245 | 1 | 85 | 1 | 177 | 1 | 198 | 1 | 270 | 1 | 300 | 0 | 267 | 0 |
| 241 | 1 | 85 | 1 | 173 | 1 | 196 | 1 | 270 | 1 | 304 | 1 | 271 | 1 |
| 239 | 1 | 85 | 1 | 181 | 1 | 196 | 1 | 276 | 1 | 300 | 1 | 267 | 1 |
| 241 | 1 | 85 | 1 | 181 | 1 | 194 | 1 | 274 | 1 | 324 | 1 | 267 | 0 |
| 241 | 1 | 99 | 1 | 181 | 1 | 196 | 1 | 274 | 1 | 304 | 1 | 267 | 0 |
| 243 | 1 | 85 | 1 | 177 | 1 | 192 | 0 | 270 | 1 | 312 | 1 | 265 | 1 |

FIG. 9C nontransmitted chromosomes

| ERSN | KID | sava5 | | ca211 | | ca212 | | 1140 | | 59 | | ca231 |
|------|-----|-------|---|-------|---|-------|---|------|---|-----|---|-------|
| 301 | 251 | 227 | 0 | 205 | 1 | 200 | 1 | 276 | 1 | 148 | 1 | 184 |
| 285 | 252 | 231 | 1 | 193 | 1 | 200 | 0 | 268 | 1 | 148 | 1 | 184 |
| 258 | 253 | 229 | 1 | 193 | 1 | 200 | 0 | 268 | 1 | 148 | 1 | 186 |
| 467 | 254 | 229 | 1 | 197 | 1 | 216 | 1 | 280 | 1 | 160 | 1 | 184 |
| 266 | 265 | 227 | 0 | 195 | 1 | 202 | 1 | 268 | 1 | 160 | 1 | 186 |
| 485 | 311 | 227 | 1 | 205 | 1 | 200 | 1 | 268 | 1 | 158 | 1 | 184 |
| 313 | 314 | 227 | 1 | 195 | 1 | 202 | 1 | 268 | 1 | 162 | 1 | 186 |
| 348 | 314 | 227 | 1 | 195 | 1 | 200 | 1 | 268 | 1 | 148 | 1 | 184 |
| 317 | 316 | 227 | 1 | 201 | 1 | 202 | 1 | 268 | 1 | 152 | 1 | 186 |
| 318 | 319 | 227 | 0 | | 0 | | 0 | 256 | 0 | 154 | 0 | |
| 320 | 321 | 237 | 1 | 201 | 0 | 200 | 0 | 268 | 1 | 154 | 0 | 186 |
| 336 | 326 | 227 | 1 | 193 | 1 | 202 | 1 | 268 | 1 | 154 | 1 | 186 |
| 325 | 326 | 227 | 1 | 201 | 1 | 202 | 1 | 276 | 1 | 148 | 1 | 186 |
| 330 | 329 | 233 | 1 | 197 | 1 | 202 | 1 | 268 | 1 | 148 | 0 | 184 |
| 476 | 331 | 229 | 0 | 199 | 1 | 200 | 0 | 276 | 1 | 154 | 1 | |
| 354 | 351 | 233 | 1 | 201 | 0 | 200 | 1 | 268 | 1 | 162 | 1 | 186 |
| 352 | 353 | 225 | 0 | 207 | 1 | 200 | 1 | 268 | 0 | 154 | 1 | 194 |
| 362 | 356 | 231 | 1 | 195 | 1 | 202 | 1 | 268 | 1 | 154 | 1 | 186 |
| 358 | 357 | 235 | 1 | 205 | 1 | 202 | 0 | 256 | 1 | 154 | 0 | 186 |
| 365 | 359 | 233 | 1 | 205 | 1 | 200 | 1 | 268 | 1 | 162 | 1 | 186 |
| 378 | 359 | 231 | 1 | 201 | 1 | 202 | 1 | 268 | 1 | 162 | 1 | 186 |
| 360 | 361 | 227 | 0 | 195 | 1 | 202 | 0 | 268 | 1 | 162 | 1 | 186 |
| 366 | 367 | 227 | 1 | 193 | 1 | 202 | 1 | 268 | 1 | 154 | 1 | 186 |
| 370 | 372 | 227 | 0 | 201 | 1 | 202 | 1 | 268 | 1 | 150 | 1 | 184 |
| 389 | 384 | 231 | 1 | 203 | 1 | 204 | 1 | 272 | 1 | 158 | 1 | 186 |
| 408 | 409 | 229 | 1 | 205 | 1 | 216 | 1 | 276 | 1 | 154 | 1 | 186 |
| 410 | 409 | 229 | 1 | 197 | 1 | 204 | 1 | 272 | 1 | 158 | 1 | 186 |
| 414 | 413 | 227 | 1 | 195 | 1 | 200 | 1 | 268 | 1 | 158 | 1 | 186 |
| 412 | 413 | 235 | 1 | 193 | 1 | 200 | 1 | 256 | 1 | 156 | 1 | 186 |
| 433 | 435 | 227 | 1 | 195 | 1 | 202 | 1 | 266 | 1 | 154 | 1 | 186 |
| 444 | 443 | 235 | 1 | 205 | 1 | 200 | 1 | 268 | 1 | 158 | 1 | 186 |
| 551 | 458 | 235 | 1 | 201 | 1 | 206 | 1 | 268 | 1 | 148 | 1 | 184 |
| 472 | 473 | 233 | 1 | 193 | 1 | 200 | 1 | 268 | 1 | 156 | 1 | 186 |
| 482 | 484 | 233 | 0 | 197 | 1 | 200 | 1 | 268 | 1 | 158 | 1 | 182 |

*FIG. 9D*

| | ta201 | | at201 | | ca225 | | w3442 | | ca213 | | ga201 | | ga203 | |
|---|---|---|---|---|---|---|---|---|---|---|---|---|---|---|
| 1 | 252 | 1 | 170 | 1 | 172 | 1 | 24 | 1 | 124 | 1 | 150 | 1 | 188 | 1 |
| 1 | 252 | 1 | 170 | 1 | 174 | 1 | 16 | 1 | 124 | 0 | 150 | 1 | 192 | 1 |
| 1 | 230 | 1 | 194 | 1 | 172 | 1 | 22 | 1 | 112 | 1 | 154 | 1 | 208 | 1 |
| 1 | 250 | 1 | 170 | 0 | 172 | 1 | 22 | 1 | 126 | 1 | 154 | 1 | 188 | 0 |
| 1 | 260 | 1 | 178 | 1 | 174 | 1 | 16 | 1 | 124 | 0 | 158 | 1 | 208 | 1 |
| 1 | 230 | 1 | 178 | 1 | 184 | 1 | 20 | 1 | 128 | 1 | 154 | 1 | 212 | 1 |
| 1 |  | 0 | 170 | 1 | 172 | 1 | 10 | 0 | 124 | 1 | 150 | 1 | 212 | 1 |
| 1 | 248 | 1 | 170 | 1 | 172 | 1 | 10 | 0 | 128 | 1 | 150 | 1 | 208 | 1 |
| 1 | 244 | 1 | 170 | 1 | 174 | 1 | 14 | 1 | 112 | 1 | 154 | 1 | 188 | 0 |
| 0 |  | 0 |  | 0 |  | 0 | 16 | 1 |  | 0 |  | 0 |  | 0 |
| 0 | 220 | 1 | 170 | 1 | 172 | 0 | 20 | 1 | 124 | 0 | 146 | 0 | 192 | 0 |
| 1 | 244 | 1 | 170 | 1 | 160 | 1 | 18 | 1 | 124 | 1 | 154 | 1 | 208 | 1 |
| 1 | 244 | 1 | 170 | 1 | 176 | 1 | 20 | 1 | 126 | 1 | 150 | 1 | 192 | 1 |
| 1 | 256 | 1 | 178 | 1 | 172 | 1 | 16 | 1 | 124 | 1 | 162 | 1 | 208 | 1 |
| 0 | 244 | 1 | 170 | 0 | 160 | 1 | 10 | 1 | 112 | 0 | 150 | 0 | 188 | 0 |
| 1 | 248 | 1 | 178 | 1 | 160 | 1 | 22 | 1 | 132 | 1 | 150 | 1 | 188 | 1 |
| 1 | 220 | 1 | 170 | 1 | 178 | 1 | 18 | 1 | 128 | 1 | 146 | 1 | 192 | 1 |
| 0 | 230 | 1 | 170 | 0 | 172 | 1 | 10 | 0 | 128 | 1 | 150 | 1 | 208 | 1 |
| 1 | 230 | 1 | 178 | 1 | 172 | 1 | 10 | 1 | 124 | 0 | 154 | 1 | 216 | 1 |
| 1 | 248 | 1 | 178 | 1 | 160 | 1 | 22 | 1 | 132 | 1 | 150 | 1 | 188 | 1 |
| 1 | 230 | 1 | 186 | 1 | 174 | 1 | 18 | 1 | 126 | 1 | 150 | 1 | 188 | 1 |
| 1 | 250 | 1 | 170 | 1 | 172 | 1 | 18 | 1 | 124 | 1 | 150 | 1 | 212 | 1 |
| 1 | 230 | 1 | 178 | 1 | 160 | 1 | 10 | 1 | 124 | 1 | 142 | 0 | 188 | 1 |
| 0 | 244 | 0 | 170 | 1 | 174 | 1 | 14 | 1 | 124 | 0 | 150 | 1 | 188 | 1 |
| 1 | 244 | 1 | 178 | 1 | 172 | 1 | 18 | 1 | 126 | 1 | 150 | 1 | 200 | 1 |
| 1 | 244 | 1 | 178 | 1 | 184 | 1 | 28 | 1 | 112 | 1 | 154 | 1 | 196 | 1 |
| 1 | 244 | 1 | 178 | 1 | 172 | 1 | 18 | 1 | 126 | 1 | 150 | 1 | 188 | 1 |
| 1 | 242 | 1 | 178 | 0 | 174 | 1 | 18 | 1 | 120 | 1 | 150 | 1 | 188 | 1 |
| 1 | 246 | 1 | 170 | 1 | 172 | 1 | 10 | 1 | 124 | 1 | 150 | 1 | 212 | 1 |
| 1 | 242 | 1 | 170 | 1 | 172 | 0 | 16 | 1 | 112 | 1 | 150 | 1 | 204 | 1 |
| 1 | 232 | 1 | 178 | 1 |  | 0 | 24 | 1 | 112 | 1 | 150 | 0 | 188 | 1 |
| 1 | 248 | 1 | 170 | 1 | 174 | 1 | 14 | 1 | 124 | 1 | 158 | 1 | 188 | 0 |
| 1 | 248 | 1 | 178 | 1 | 184 | 1 | 10 | 0 | 112 | 1 | 146 | 1 | 188 | 1 |
| 0 | 248 | 1 | 170 | 1 | 174 | 1 | 16 | 1 | 124 | 1 | 150 | 1 | 188 | 1 |

FIG. 9E nontransmitted chromosomes

| ca219 | | 1105 | | ca209 | | ca202 | | 1146 | | 166d05 | | 476 | |
|---|---|---|---|---|---|---|---|---|---|---|---|---|---|
| 235 | 1 | 101 | 1 | 177 | 0 | 200 | 1 | 272 | 1 | 316 | 1 | 267 | 1 |
| 235 | 0 | 85 | 1 | 173 | 0 | 192 | 1 | 274 | 0 | 308 | 1 | 267 | 1 |
| 235 | 1 | 101 | 1 | 181 | 1 | 196 | 1 | 274 | 1 | 308 | 1 | 265 | 1 |
| 245 | 1 | 103 | 1 | 175 | 1 | 198 | 1 | 274 | 1 | 300 | 1 | 271 | 0 |
| 235 | 1 | 101 | 1 | 181 | 1 | 202 | 1 | 274 | 1 | 316 | 1 | 265 | 1 |
| 245 | 1 | 85 | 1 | 179 | 1 | 184 | 0 | 270 | 1 | 308 | 1 | 269 | 0 |
| 241 | 1 | 85 | 1 | 173 | 1 | 192 | 1 | 270 | 1 | 312 | 1 | 269 | 1 |
| 241 | 1 | 85 | 1 | 173 | 1 | 198 | 1 | 270 | 1 | 308 | 1 | 271 | 1 |
| 235 | 0 | 101 | 0 | 173 | 0 | 190 | 1 | 274 | 1 | 304 | 0 | 267 | 0 |
| 245 | 1 | 85 | 1 |  | 0 |  | 0 | 274 | 1 | 320 | 1 | 269 | 1 |
|  | 0 | 103 | 1 | 173 | 1 | 182 | 1 | 274 | 1 | 312 | 1 | 271 | 0 |
| 241 | 1 | 85 | 1 | 173 | 1 | 182 | 1 | 270 | 1 | 312 | 1 | 273 | 1 |
| 241 | 1 | 85 | 1 | 177 | 1 | 200 | 1 | 274 | 1 | 308 | 1 | 263 | 1 |
| 235 | 1 | 85 | 1 | 173 | 1 | 196 | 1 | 270 | 0 | 316 | 1 | 265 | 1 |
| 241 | 1 | 85 | 1 | 173 | 1 | 182 | 1 | 270 | 1 | 300 | 1 | 265 | 0 |
| 241 | 1 | 85 | 1 | 173 | 1 | 182 | 1 | 270 | 1 | 308 | 1 | 267 | 0 |
| 241 | 1 | 87 | 1 | 173 | 1 | 182 | 0 | 272 | 1 | 300 | 1 | 271 | 1 |
| 245 | 1 | 85 | 0 | 177 | 1 | 198 | 1 | 274 | 1 | 300 | 1 | 271 | 0 |
| 241 | 0 | 85 | 0 | 173 | 0 | 190 | 0 | 270 | 0 | 312 | 1 | 273 | 1 |
| 241 | 1 | 85 | 1 | 173 | 1 | 182 | 1 | 270 | 1 | 312 | 1 | 267 | 0 |
| 241 | 1 | 85 | 1 | 177 | 1 | 192 | 1 | 270 | 1 | 312 | 1 | 267 | 0 |
| 241 | 1 | 85 | 1 | 173 | 1 | 192 | 0 | 270 | 1 | 308 | 1 | 269 | 1 |
| 243 | 1 | 85 | 1 | 173 | 0 | 200 | 1 | 274 | 1 | 308 | 0 | 265 | 0 |
| 243 | 1 | 85 | 1 | 173 | 1 | 190 | 0 | 270 | 0 | 316 | 1 | 273 | 1 |
| 235 | 0 | 95 | 1 | 173 | 0 | 196 | 1 | 274 | 1 | 312 | 1 | 271 | 1 |
| 243 | 1 | 85 | 1 | 173 | 0 | 198 | 1 | 270 | 1 | 300 | 1 | 271 | 1 |
| 241 | 1 | 85 | 1 | 173 | 0 | 196 | 1 | 274 | 1 | 316 | 1 | 267 | 1 |
| 241 | 1 | 85 | 1 | 173 | 1 | 194 | 1 | 270 | 1 | 316 | 1 | 265 | 1 |
| 241 | 1 | 85 | 1 | 173 | 1 | 200 | 1 | 274 | 1 | 316 | 1 | 271 | 1 |
| 241 | 1 | 85 | 1 | 173 | 1 | 194 | 1 | 270 | 1 | 300 | 1 | 271 | 1 |
| 235 | 1 | 105 | 1 | 181 | 1 | 200 | 1 | 272 | 1 | 316 | 1 | 267 | 1 |
| 239 | 0 | 101 | 1 | 173 | 1 | 196 | 1 | 274 | 1 | 300 | 1 | 271 | 1 |
| 241 | 1 | 85 | 1 | 173 | 0 | 192 | 1 | 270 | 0 | 316 | 1 | 265 | 1 |
| 241 | 1 | 83 | 1 | 173 | 1 | 196 | 1 | 270 | 0 | 304 | 1 | 267 | 0 |

*FIG. 9F* nontransmitted chromosomes

| ERSN | KID | sava5 | | ca211 | | ca212 | | 1140 | | 59 | | ca231 |
|------|-----|-------|---|-------|---|-------|---|------|---|-----|---|-------|
| 486 | 487 | 227 | 1 | 201 | 1 | 202 | 1 | 256 | 1 | 154 | 1 | 186 |
| 508 | 488 | 233 | 1 | 205 | 1 | 202 | 1 | 268 | 1 | 148 | 1 | 184 |
| 635 | 498 | 227 | 1 | 193 | 1 | 202 | 1 | 268 | 1 | 148 | 1 | 184 |
| 527 | 501 | 229 | 1 | 183 | 1 | 216 | 1 | 280 | 1 | 158 | 1 | 186 |
| 528 | 501 | 225 | 1 | 183 | 1 | 216 | 1 | 268 | 1 | 152 | 1 | 186 |
| 502 | 505 | 235 | 1 | 205 | 1 | 200 | 1 | 268 | 1 | 148 | 1 | 184 |
| 517 | 516 | | 0 | | 0 | | 0 | | 0 | | 0 | |
| 529 | 531 | 233 | 1 | 205 | 1 | 200 | 0 | 268 | 1 | 158 | 1 | 186 |
| 633 | 536 | 229 | 0 | 201 | 1 | 200 | 1 | 268 | 0 | 154 | 1 | 186 |
| 532 | 537 | 227 | 1 | 201 | 1 | 200 | 1 | 268 | 1 | 150 | 1 | 186 |
| 534 | 537 | 235 | 1 | 205 | 1 | 200 | 1 | 268 | 1 | 158 | 1 | 186 |
| 562 | 540 | 229 | 1 | 195 | 1 | 202 | 1 | 268 | 1 | 160 | 1 | 184 |
| 539 | 540 | 229 | 1 | 207 | 1 | 200 | 1 | 268 | 1 | 154 | 1 | 194 |
| 576 | 578 | 235 | 1 | 199 | 1 | 200 | 1 | 256 | 1 | 158 | 1 | 186 |
| 579 | 578 | 233 | 1 | 199 | 1 | 200 | 1 | 278 | 1 | 148 | 1 | 186 |
| 582 | 587 | 227 | 1 | 201 | 1 | 202 | 1 | 268 | 1 | 148 | 1 | 202 |
| 580 | 587 | 229 | 1 | | 0 | 200 | 1 | 268 | 1 | 154 | 1 | 186 |
| 638 | 637 | 237 | 1 | 203 | 1 | 206 | 1 | 268 | 1 | 154 | 0 | 186 |
| 647 | 649 | 229 | 1 | 195 | 1 | 202 | 1 | 268 | 1 | 154 | 1 | 186 |
| 646 | 649 | 231 | 1 | 201 | 1 | 206 | 1 | 268 | 1 | 154 | 1 | 186 |
| 652 | 653 | 235 | 1 | 201 | 1 | 206 | 1 | 268 | 0 | 154 | 0 | 186 |
| 662 | 661 | 235 | 1 | 209 | 1 | 202 | 1 | 280 | 1 | 154 | 1 | 186 |
| 660 | 661 | 233 | 1 | 183 | 1 | 216 | 1 | 268 | 1 | 158 | 1 | 186 |
| 666 | 667 | 235 | 1 | 203 | 1 | 202 | 1 | 268 | 1 | 158 | 1 | 186 |
| 668 | 667 | 237 | 1 | 209 | 1 | 202 | 1 | 268 | 1 | 150 | 1 | 186 |
| 670 | 669 | 235 | 1 | 205 | 1 | 200 | 1 | 268 | 1 | 148 | 1 | 184 |
| 671 | 669 | 227 | 1 | 195 | 1 | 200 | 1 | 268 | 1 | 158 | 1 | 186 |
| 678 | 676 | 223 | 1 | 201 | 1 | 200 | 0 | 278 | 1 | 156 | 1 | 200 |
| 730 | 684 | 229 | 1 | 195 | 1 | 200 | 0 | 268 | 1 | 148 | 1 | 198 |

*FIG. 9G*

| | ta201 | | at201 | | ca225 | | w3442 | | ca213 | | ga201 | | ga203 | |
|---|---|---|---|---|---|---|---|---|---|---|---|---|---|---|
| 0 | 230 | 1 | 178 | 1 | 172 | 1 | 10 | 0 | 124 | 1 | 150 | 1 | 188 | 1 |
| 1 | 220 | 1 | 170 | 1 | 160 | 1 | 24 | 1 | 112 | 1 | 150 | 1 | 188 | 1 |
| 1 | 254 | 1 | 170 | 1 | 174 | 1 | 16 | 1 | 124 | 1 | 142 | 1 | 188 | 1 |
| 1 | 230 | 1 | 170 | 1 | 172 | 1 | 22 | 1 | 126 | 1 | 146 | 1 | 212 | 1 |
| 1 | 242 | 1 | 170 | 1 | 176 | 1 | 10 | 1 | 126 | 1 | 154 | 1 | 208 | 1 |
| 1 | | 0 | 170 | 1 | 174 | 1 | 10 | 1 | 126 | 1 | 150 | 1 | 188 | 1 |
| 0 | | 0 | | 0 | | 0 | | 0 | | 0 | | 0 | | 0 |
| 1 | 242 | 1 | 170 | 1 | 180 | 1 | 10 | 0 | 128 | 1 | 150 | 1 | 204 | 1 |
| 1 | 230 | 1 | 178 | 1 | 168 | 0 | 10 | 1 | 124 | 0 | 150 | 1 | | 0 |
| 1 | 242 | 1 | 170 | 0 | 172 | 1 | 10 | 1 | 126 | 1 | 150 | 1 | 192 | 1 |
| 1 | 232 | 1 | 170 | 0 | 160 | 1 | 24 | 1 | 112 | 1 | 150 | 1 | 208 | 1 |
| 1 | 250 | 1 | 170 | 1 | 160 | 1 | 18 | 1 | 124 | 1 | 150 | 1 | 212 | 1 |
| 1 | 220 | 1 | 170 | 1 | 178 | 1 | 18 | 1 | 128 | 1 | 150 | 1 | 192 | 1 |
| 1 | 246 | 1 | 170 | 1 | 174 | 1 | 10 | 1 | 124 | 1 | 158 | 1 | 188 | 1 |
| 1 | 246 | 1 | 170 | 1 | 184 | 1 | 16 | 1 | 124 | 1 | 150 | 1 | 208 | 1 |
| 1 | 220 | 1 | 178 | 1 | 184 | 1 | 10 | 1 | 128 | 1 | 150 | 1 | 212 | 1 |
| 1 | 244 | 1 | 170 | 1 | 160 | 1 | 10 | 1 | 126 | 1 | 150 | 1 | 200 | 1 |
| 1 | 228 | 1 | 170 | 1 | 160 | 1 | 22 | 1 | 126 | 1 | 142 | 0 | 212 | 1 |
| 1 | 232 | 1 | 178 | 1 | 160 | 1 | 10 | 1 | 124 | 1 | 150 | 1 | 216 | 1 |
| 1 | 230 | 1 | 178 | 1 | 160 | 1 | 10 | 1 | 124 | 1 | 154 | 1 | 188 | 1 |
| 1 | 230 | 1 | 178 | 1 | 172 | 1 | 16 | 1 | 126 | 1 | 150 | 1 | 188 | 0 |
| 1 | 242 | 1 | 178 | 1 | 172 | 1 | 22 | 1 | 126 | 1 | 150 | 1 | 188 | 1 |
| 1 | | 0 | 170 | 1 | 160 | 1 | 14 | 1 | 122 | 1 | 150 | 1 | 192 | 1 |
| 1 | 246 | 1 | 170 | 1 | 174 | 1 | 10 | 1 | 126 | 1 | 150 | 1 | 192 | 1 |
| 1 | 252 | 1 | 178 | 1 | 172 | 1 | 16 | 1 | 128 | 1 | 150 | 1 | 196 | 1 |
| 1 | 254 | 1 | 170 | 1 | 174 | 1 | 10 | 1 | 126 | 1 | 154 | 1 | 192 | 1 |
| 1 | 230 | 1 | 178 | 1 | 168 | 1 | 16 | 1 | 128 | 1 | 154 | 1 | 188 | 1 |
| 1 | 252 | 1 | 174 | 1 | 174 | 1 | 10 | 1 | 124 | 1 | 150 | 1 | 208 | 1 |
| 1 | 220 | 1 | 170 | 1 | 174 | 1 | 20 | 1 | 126 | 1 | 150 | 1 | 196 | 1 |

*FIG. 9H* nontransmitted chromosomes

| ca219 | | 1105 | | ca209 | | ca202 | | 1146 | | 166d05 | | 476 | |
|---|---|---|---|---|---|---|---|---|---|---|---|---|---|
| 241 | 0 | 103 | 1 | 173 | 1 | 192 | 1 | 274 | 1 | 312 | 1 | 267 | 1 |
| 243 | 1 | 85 | 1 | 173 | 1 | 196 | 1 | 274 | 1 | 308 | 1 | 273 | 1 |
| 243 | 1 | 85 | 1 | 173 | 1 | 200 | 1 | 274 | 1 | 312 | 1 | 271 | 1 |
| 241 | 1 | 85 | 1 | 173 | 1 | 182 | 1 | 270 | 0 | 320 | 1 | 267 | 1 |
| 241 | 1 | 87 | 1 | 173 | 1 | 198 | 1 | 270 | 0 | 312 | 1 | 267 | 1 |
| 235 | 1 | 97 | 1 | 181 | 1 | 192 | 0 | 274 | 1 | 300 | 1 | 271 | 1 |
|  | 0 |  | 0 |  | 0 |  | 0 | 272 | 1 |  | 0 |  | 0 |
| 235 | 1 | 81 | 1 | 173 | 1 | 182 | 1 | 278 | 1 | 320 | 1 | 261 | 1 |
| 241 | 1 | 85 | 0 | 173 | 0 | 200 | 1 | 270 | 1 | 304 | 1 | 271 | 1 |
| 241 | 1 | 85 | 0 | 173 | 1 | 196 | 1 | 270 | 1 | 304 | 1 | 271 | 1 |
| 235 | 1 | 85 | 0 | 181 | 1 | 194 | 1 | 274 | 1 | 308 | 1 | 267 | 1 |
| 239 | 1 | 85 | 1 | 173 | 1 | 194 | 1 | 272 | 0 | 316 | 1 | 271 | 1 |
| 241 | 1 | 85 | 1 | 173 | 1 | 182 | 1 | 272 | 0 | 300 | 1 | 271 | 1 |
| 241 | 1 | 105 | 1 | 173 | 1 | 192 | 0 | 274 | 1 | 312 | 1 | 267 | 1 |
| 241 | 1 | 87 | 1 | 173 | 1 | 192 | 0 | 272 | 1 | 304 | 1 | 275 | 1 |
|  | 0 | 103 | 1 | 173 | 1 | 194 | 1 | 270 | 1 | 316 | 1 | 271 | 1 |
|  | 0 | 101 | 1 | 173 | 1 | 196 | 1 | 272 | 1 | 308 | 1 | 271 | 1 |
| 241 | 1 | 87 | 1 | 173 | 1 | 182 | 1 | 274 | 1 | 320 | 1 | 269 | 1 |
| 241 | 0 | 85 | 1 | 173 | 1 | 194 | 1 | 270 | 1 | 312 | 1 | 267 | 1 |
| 241 | 0 | 85 | 1 | 173 | 1 | 196 | 1 | 274 | 1 | 300 | 1 | 271 | 1 |
| 235 | 1 | 99 | 1 | 181 | 1 | 192 | 1 | 274 | 1 | 312 | 1 | 267 | 1 |
| 235 | 1 | 101 | 1 | 181 | 1 | 196 | 1 | 272 | 1 | 300 | 1 | 271 | 1 |
| 235 | 1 | 85 | 1 | 179 | 1 | 196 | 1 | 274 | 1 | 312 | 1 | 271 | 1 |
| 241 | 1 | 85 | 1 | 173 | 1 | 192 | 1 | 270 | 1 | 312 | 1 | 271 | 1 |
| 241 | 1 | 87 | 1 | 173 | 1 | 182 | 1 | 270 | 1 | 316 | 1 | 273 | 1 |
| 235 | 1 |  | 0 | 181 | 1 | 196 | 1 | 274 | 1 | 300 | 1 | 271 | 1 |
| 239 | 1 | 85 | 0 | 181 | 1 | 196 | 1 | 276 | 1 | 300 | 1 | 267 | 1 |
| 241 | 1 | 83 | 1 | 177 | 1 | 182 | 1 | 276 | 1 | 308 | 0 | 269 | 1 |
| 235 | 0 | 93 | 1 | 173 | 0 | 202 | 1 | 272 | 0 | 300 | 1 | 273 | 1 |
|  |  |  |  |  |  | 79 |  |  |  |  |  |  |  |

FIG. 9I

| cont | sava5 | ca211 | | ca212 | | 1140 | | 59 | | ca231 | | ta201 |
|---|---|---|---|---|---|---|---|---|---|---|---|---|
| | | | | | | controls | | | | | | |
| 98 | miss | 193 | 1 | 200 | 1 | | 0 | 156 | 1 | 186 | 1 | 230 |
| 98 | 17 | 193 | 1 | 216 | 1 | | 0 | 148 | 1 | 186 | 1 | 244 |
| 99 | | 193 | 1 | 206 | 1 | 268 | 1 | 150 | 1 | 184 | 1 | 252 |
| 99 | | 195 | 1 | 200 | 1 | 268 | 1 | 154 | 1 | 184 | 1 | 220 |
| 101 | | 189 | 1 | 206 | 1 | 272 | 1 | 154 | 1 | 186 | 1 | 260 |
| 101 | | 203 | 1 | 200 | 1 | 268 | 1 | 150 | 1 | 186 | 1 | 244 |
| 102 | | 195 | 1 | 202 | 1 | 268 | 1 | 150 | 1 | 202 | 1 | 220 |
| 102 | | 205 | 1 | 200 | 1 | 268 | 1 | 162 | 1 | 186 | 1 | 248 |
| 104 | | 195 | 1 | 200 | 1 | 268 | 1 | 154 | 1 | 186 | 1 | 244 |
| 104 | | 203 | 1 | 216 | 1 | 268 | 1 | 156 | 1 | 186 | 1 | 244 |
| 105 | | 193 | 1 | 202 | 1 | 268 | 1 | 156 | 1 | 186 | 1 | 244 |
| 105 | | 201 | 1 | 216 | 1 | 268 | 1 | 148 | 1 | 186 | 1 | 246 |
| 107 | | | 0 | 206 | 1 | 268 | 1 | 154 | 1 | 186 | 1 | 246 |
| 107 | | | 0 | 202 | 1 | 274 | 1 | 150 | 1 | 184 | 1 | 246 |
| 108 | | 201 | 0 | 200 | 1 | 268 | 1 | 162 | 1 | 186 | 1 | 230 |
| 108 | | 195 | 0 | 202 | 1 | 280 | 1 | 154 | 1 | 186 | 1 | 242 |
| 110 | | 199 | 1 | 218 | 1 | 268 | 1 | 160 | 1 | 184 | 1 | 248 |
| 110 | | 205 | 1 | 200 | 1 | 268 | 1 | 148 | 1 | 184 | 1 | 254 |
| 111 | | 193 | 1 | 202 | 1 | 268 | 1 | 154 | 1 | 186 | 1 | 232 |
| 111 | | 191 | 1 | 202 | 1 | 268 | 1 | 150 | 1 | 184 | 1 | 252 |
| 114 | | 207 | 1 | 202 | 1 | 268 | 1 | 150 | 1 | 200 | 1 | 220 |
| 114 | | 195 | 1 | 200 | 1 | 278 | 1 | 154 | 1 | 186 | 1 | 252 |
| 113 | | 191 | 1 | 202 | 1 | 276 | 1 | 150 | 1 | 184 | 1 | 250 |
| 113 | | 207 | 1 | 216 | 1 | 268 | 1 | 150 | 1 | 186 | 1 | 244 |
| 116 | | 193 | 1 | 202 | 1 | 268 | 1 | 154 | 1 | 186 | 1 | 230 |
| 116 | | 195 | 1 | 202 | 1 | 268 | 1 | 154 | 1 | 186 | 1 | 248 |
| 117 | | 201 | 1 | 200 | 1 | 268 | 1 | 154 | 1 | 186 | 1 | 232 |
| 117 | | 195 | 1 | 202 | 1 | 268 | 1 | 160 | 1 | 186 | 1 | 256 |
| 119 | | 193 | 1 | 200 | 1 | 270 | 1 | 162 | 1 | 186 | 1 | 244 |
| 119 | | 193 | 1 | 206 | 1 | 268 | 1 | 154 | 1 | 186 | 1 | 230 |
| 120 | | 193 | 1 | 216 | 1 | 276 | 1 | 158 | 1 | 186 | 1 | 242 |
| 120 | | 203 | 1 | 204 | 1 | 272 | 1 | 158 | 1 | 186 | 1 | 244 |
| 122 | | 183 | 1 | 200 | 1 | 268 | 1 | 154 | 1 | 186 | 1 | 242 |
| 122 | | 195 | 1 | 218 | 1 | 268 | 1 | 156 | 1 | 186 | 1 | 232 |

*FIG. 10A*

| at201 | | ca225 | | w3442 | | ca213 | | ga201 | | ga203 | |
|---|---|---|---|---|---|---|---|---|---|---|---|
| 1 | 178 | 1 | 176 | 1 | 10 | 1 | 126 | 1 | 150 | 1 | 208 | 1 |
| 1 | 178 | 1 | 172 | 1 | 18 | 1 | 124 | 1 | 150 | 1 | 208 | 1 |
| 1 | 178 | 1 | 172 | 1 | 20 | 1 | 124 | 1 | 142 | 1 | 204 | 1 |
| 1 | 170 | 1 | 170 | 1 | 10 | 1 | 128 | 1 | 150 | 1 | 188 | 1 |
| 1 | 178 | 1 | 174 | 1 | 20 | 1 | 126 | 1 | 158 | 1 | 216 | 1 |
| 1 | 170 | 1 | 160 | 1 | 14 | 1 | 122 | 1 | 150 | 1 | 188 | 1 |
| 1 | 178 | 1 | 172 | 1 | 24 | 1 | 124 | 1 | 150 | 1 | 212 | 1 |
| 1 | 178 | 1 | 160 | 1 | 22 | 1 | 132 | 1 | 150 | 1 | 188 | 1 |
| 1 | 170 | 1 | 160 | 1 | 10 | 1 | 126 | 1 | 150 | 1 | 188 | 1 |
| 1 | 186 | 1 | 174 | 1 | 14 | 1 | 126 | 1 | 150 | 1 | 192 | 1 |
| 1 | 170 | 1 | 172 | 1 | 10 | 1 | 126 | 1 | 150 | 1 | 188 | 1 |
| 1 | 194 | 1 | 172 | 1 | 16 | 1 | 124 | 1 | 150 | 1 | 188 | 1 |
| 1 | 170 | 1 | 176 | 1 | 22 | 0 | | 0 | 154 | 1 | 188 | 1 |
| 1 | 170 | 1 | 174 | 1 | 16 | 0 | | 0 | 150 | 1 | 216 | 1 |
| 1 | 178 | 1 | 172 | 1 | 22 | 1 | 126 | 1 | 150 | 1 | 188 | 1 |
| 1 | 178 | 1 | 172 | 1 | 22 | 1 | 126 | 1 | 150 | 1 | 192 | 1 |
| 1 | 170 | 1 | 172 | 1 | 16 | 0 | 124 | 1 | 150 | 1 | 208 | 1 |
| 1 | 170 | 1 | 174 | 1 | 10 | 0 | 126 | 1 | 150 | 1 | 188 | 1 |
| 1 | 178 | 1 | 160 | 1 | | 0 | 124 | 1 | 150 | 1 | 188 | 1 |
| 1 | 170 | 1 | 160 | 1 | | 0 | 128 | 1 | 150 | 1 | 188 | 1 |
| 1 | 170 | 1 | 174 | 0 | 24 | 1 | 126 | 1 | 150 | 1 | 212 | 1 |
| 1 | 178 | 1 | 172 | 0 | 18 | 1 | 124 | 1 | 150 | 1 | 192 | 1 |
| 1 | 170 | 1 | 174 | 0 | 22 | 1 | 124 | 1 | 146 | 1 | 216 | 1 |
| 1 | 170 | 1 | 172 | 0 | 16 | 1 | 124 | 1 | 150 | 1 | 192 | 1 |
| 1 | 178 | 1 | 172 | 1 | 10 | 1 | 124 | 0 | 150 | 1 | 188 | 1 |
| 1 | 170 | 1 | 172 | 1 | 10 | 1 | 126 | 0 | 150 | 1 | 212 | 1 |
| 1 | 178 | 1 | 172 | 1 | 10 | 1 | 124 | 0 | 142 | 1 | 212 | 1 |
| 1 | 178 | 1 | 174 | 1 | 16 | 1 | 126 | 0 | 158 | 1 | 212 | 1 |
| 1 | 170 | 1 | 172 | 1 | 18 | 0 | 124 | 1 | 150 | 1 | 216 | 1 |
| 1 | 178 | 1 | 172 | 1 | 10 | 0 | 126 | 1 | 150 | 1 | 188 | 1 |
| 1 | 178 | 1 | 174 | 1 | 18 | 0 | 112 | 1 | 154 | 1 | 192 | 1 |
| 1 | 178 | 1 | 172 | 1 | 10 | 0 | 126 | 1 | 150 | 1 | 200 | 1 |
| 1 | 178 | 1 | 160 | 1 | 16 | 1 | 124 | 1 | 150 | 1 | 204 | 1 |
| 1 | 178 | 1 | 160 | 1 | 26 | 1 | 124 | 1 | 150 | 1 | 188 | 1 |

*FIG. 10B* controls

| ca219 | 1105 | 18SCA20 | SC | KID |
|---|---|---|---|---|
| 241 | 1 | missing 173 | 1 | 100 |
| 241 | 1 | 177 | 1 | 100 |
| 235 | 1 | 173 | 1 | 100 |
| 245 | 1 | 175 | 1 | 100 |
| 235 | 1 | 173 | 1 | 103 |
| 235 | 1 | 181 | 1 | 103 |
| 241 | 1 | 173 | 1 | 103 |
| 241 | 1 | 173 | 1 | 103 |
| 235 | 1 | 181 | 1 | 106 |
| 241 | 1 | 173 | 1 | 106 |
| 241 | 1 | 173 | 1 | 106 |
| 241 | 1 | 173 | 1 | 106 |
| 241 | 1 | 173 | 1 | 109 |
| 241 | 1 | 173 | 1 | 109 |
| 241 | 1 | 173 | 1 | 109 |
| 245 | 1 | 175 | 1 | 109 |
| 235 | 1 | | 0 | 112 |
| 235 | 1 | | 0 | 112 |
| 243 | 1 | 181 | 0 | 112 |
| 235 | 1 | 173 | 0 | 112 |
| 241 | 1 | 173 | 1 | 115 |
| 241 | 1 | 173 | 1 | 115 |
| 241 | 1 | 173 | 1 | 115 |
| 241 | 1 | 173 | 1 | 115 |
| 241 | 1 | 173 | 1 | 118 |
| 241 | 1 | 173 | 1 | 118 |
| 241 | 1 | 173 | 1 | 118 |
| 241 | 1 | 177 | 1 | 118 |
| 241 | 1 | 173 | 1 | 121 |
| 241 | 1 | 173 | 1 | 121 |
| 241 | 1 | 173 | 1 | 121 |
| 235 | 1 | 181 | 1 | 121 |
| | 0 | 173 | 1 | 124 |
| | 0 | 173 | 1 | 124 |

*FIG. 10C* controls

| cont | sava5 | ca211 | | ca212 | | 1140 | | 59 | | ca231 | | ta201 |
|---|---|---|---|---|---|---|---|---|---|---|---|---|
| 123 | | 193 | 1 | 200 | 1 | 268 | 1 | 150 | 1 | 184 | 1 | 252 |
| 123 | | 195 | 1 | 216 | 1 | 268 | 1 | 154 | 1 | 184 | 1 | 232 |
| 125 | | 203 | 1 | 200 | 1 | 268 | 1 | 148 | 1 | 184 | 1 | 252 |
| 125 | | 205 | 1 | 202 | 1 | 268 | 1 | 148 | 1 | 188 | 1 | 250 |
| 126 | | 205 | 1 | 200 | 1 | 268 | 1 | 148 | 1 | 186 | 1 | 248 |
| 126 | | 195 | 1 | 204 | 1 | 268 | 1 | 150 | 1 | 186 | 1 | 246 |
| 128 | | 193 | 1 | 200 | 1 | 256 | 1 | 158 | 1 | 186 | 1 | |
| 128 | | 191 | 1 | 200 | 1 | 268 | 1 | 160 | 1 | 184 | 1 | |
| 129 | | 193 | 1 | 206 | 1 | 256 | 1 | 154 | 1 | 186 | 1 | 244 |
| 129 | | 195 | 1 | 216 | 1 | 268 | 1 | 150 | 1 | 184 | 1 | 250 |
| 131 | | 201 | 0 | 200 | 1 | 268 | 1 | 154 | 1 | 186 | 0 | 252 |
| 131 | | 197 | 0 | 200 | 1 | 268 | 1 | 150 | 1 | 184 | 0 | 244 |
| 132 | | 205 | 0 | 200 | 1 | 268 | 1 | 148 | 1 | 186 | 0 | 252 |
| 132 | | 203 | 0 | 200 | 1 | 268 | 1 | 158 | 1 | 184 | 0 | 248 |
| 134 | | 193 | 1 | 216 | 1 | 268 | 1 | 148 | 1 | 186 | 1 | 220 |
| 134 | | 205 | 1 | 202 | 1 | 266 | 1 | 160 | 1 | 186 | 1 | 230 |
| 135 | | 193 | 1 | 202 | 1 | 268 | 1 | 154 | 1 | 186 | 1 | 244 |
| 135 | | 205 | 1 | 202 | 1 | 268 | 1 | 154 | 1 | 184 | 1 | 230 |
| 138 | | 193 | 1 | 202 | 1 | 268 | 1 | 154 | 1 | 186 | 1 | 230 |
| 138 | | 207 | 1 | 200 | 1 | 280 | 1 | 148 | 1 | 184 | 1 | 252 |
| 137 | | 193 | 1 | 206 | 1 | 268 | 1 | 154 | 1 | 186 | 1 | 230 |
| 137 | | 201 | 1 | 216 | 1 | 270 | 1 | 148 | 1 | 184 | 1 | 256 |
| 144 | | | 0 | 200 | 1 | 256 | 1 | 154 | 1 | 186 | 1 | |
| 144 | | | 0 | 206 | 1 | 268 | 1 | 154 | 1 | 186 | 1 | |
| 68 | | 195 | 1 | 202 | 1 | 268 | 1 | 164 | 1 | 186 | 1 | |
| 68 | | 193 | 1 | 202 | 1 | 268 | 1 | 160 | 1 | 186 | 1 | |
| 69 | | 195 | 1 | 218 | 1 | 268 | 1 | 148 | 1 | 186 | 1 | 246 |
| 69 | | 201 | 1 | 216 | 1 | 268 | 1 | 158 | 1 | 186 | 1 | 230 |
| 72 | | 193 | 1 | 200 | 1 | 268 | 1 | 148 | 1 | 184 | 1 | |
| 72 | | 193 | 1 | 206 | 1 | 256 | 1 | 156 | 1 | 186 | 1 | |
| 71 | | 193 | 1 | 216 | 1 | 268 | 1 | 146 | 1 | 192 | 1 | 248 |
| 71 | | 193 | 1 | 206 | 1 | 256 | 1 | 156 | 1 | 186 | 1 | 232 |
| 74 | | 195 | 1 | 218 | 1 | 268 | 1 | 148 | 1 | 186 | 1 | 246 |
| 74 | | 205 | 1 | 200 | 1 | 268 | 1 | 158 | 1 | 186 | 1 | 222 |

*FIG. 10D*

| | at201 | | ca225 | | w3442 | | ca213 | | ga201 | | ga203 | | |
|---|---|---|---|---|---|---|---|---|---|---|---|---|---|
| | 1 | 170 | 1 | 160 | 1 | 10 | 1 | 126 | 1 | 154 | 0 | 188 | 1 |
| | 1 | 170 | 1 | 160 | 1 | 20 | 1 | 112 | 1 | 150 | 0 | 192 | 1 |
| | 1 | | 0 | 174 | 1 | 18 | 1 | 124 | 1 | | 0 | 212 | 1 |
| | 1 | | 0 | 172 | 1 | 16 | 1 | 124 | 1 | | 0 | 192 | 1 |
| | 1 | 170 | 1 | 160 | 1 | 14 | 1 | 128 | 0 | 150 | 1 | 188 | 1 |
| | 1 | 178 | 1 | 172 | 1 | 22 | 1 | 126 | 0 | 150 | 1 | 208 | 1 |
| | 0 | 170 | 1 | 174 | 1 | 14 | 1 | 112 | 1 | 158 | 1 | 188 | 1 |
| | 0 | 170 | 1 | 172 | 1 | 18 | 1 | 122 | 1 | 150 | 1 | 208 | 1 |
| | 1 | 170 | 1 | 174 | 1 | 10 | 1 | 112 | 1 | 158 | 1 | 188 | 1 |
| | 1 | 170 | 1 | 172 | 1 | 14 | 1 | 126 | 1 | 150 | 1 | 192 | 1 |
| | 0 | 186 | 0 | 176 | 0 | 18 | 1 | 126 | 1 | 150 | 1 | 188 | 1 |
| | 0 | 170 | 0 | 172 | 0 | 10 | 1 | 126 | 1 | 150 | 1 | 188 | 1 |
| | 0 | 186 | 0 | 174 | 0 | 18 | 1 | 124 | 1 | 150 | 1 | 212 | 1 |
| | 0 | 170 | 0 | 172 | 0 | 18 | 1 | 124 | 1 | 158 | 1 | 208 | 1 |
| | 1 | 170 | 1 | 174 | 1 | 14 | 1 | 124 | 1 | 150 | 1 | 208 | 1 |
| | 1 | 194 | 1 | 172 | 1 | 22 | 1 | 112 | 1 | 154 | 1 | 208 | 1 |
| | 1 | 170 | 1 | 160 | 1 | 18 | 1 | 124 | 1 | 154 | 1 | 208 | 1 |
| | 1 | 178 | 1 | 184 | 1 | 20 | 1 | 128 | 1 | 154 | 1 | 208 | 1 |
| | 1 | 178 | 1 | 172 | 0 | 10 | 1 | 124 | 1 | | 0 | 216 | 1 |
| | 1 | 178 | 1 | 174 | 0 | 20 | 1 | 126 | 1 | | 0 | 216 | 1 |
| | 1 | 178 | 1 | 172 | 0 | 10 | 1 | 126 | 1 | 150 | 1 | 192 | 1 |
| | 1 | 186 | 1 | 174 | 0 | 10 | 1 | 126 | 1 | 150 | 1 | 212 | 1 |
| | 0 | | 0 | 174 | 1 | 10 | 1 | 126 | 1 | 150 | 1 | 208 | 1 |
| | 0 | | 0 | 176 | 1 | 22 | 1 | 124 | 1 | 150 | 1 | 188 | 1 |
| | 0 | | 0 | 172 | 1 | 22 | 1 | 126 | 1 | 150 | 1 | 208 | 1 |
| | 0 | | 0 | 172 | 1 | 18 | 1 | 122 | 1 | 150 | 1 | 208 | 1 |
| | 1 | | 0 | 160 | 1 | 10 | 1 | 124 | 1 | 146 | 1 | 208 | 1 |
| | 1 | | 0 | 172 | 1 | 20 | 1 | 124 | 1 | 150 | 1 | 204 | 1 |
| | 0 | 170 | 1 | 174 | 1 | 16 | 1 | 124 | 1 | 150 | 1 | 188 | 1 |
| | 0 | 170 | 1 | 172 | 1 | 10 | 1 | 124 | 1 | 150 | 1 | 192 | 1 |
| | 1 | 170 | 1 | 174 | 1 | 16 | 1 | 124 | 1 | 154 | 1 | 196 | 1 |
| | 1 | 170 | 1 | 174 | 1 | 10 | 1 | 126 | 1 | 150 | 1 | 212 | 1 |
| | 1 | 170 | 1 | 160 | 1 | 10 | 1 | 124 | 1 | 154 | 1 | 216 | 1 |
| | 1 | 170 | 1 | 160 | 1 | 24 | 1 | 112 | 1 | 154 | 1 | 188 | 1 |

*FIG. 10E* controls

| ca219 | 1105 | 18SCA20 | SC | KID |
|---|---|---|---|---|
| 241 | 1 |  | 173 | 1 | 124 |
| 241 | 1 | 177 | 1 | 124 |
| 241 | 1 | 173 | 1 | 127 |
| 241 | 1 | 173 | 1 | 127 |
| 243 | 1 | 173 | 1 | 127 |
| 239 | 1 | 173 | 1 | 127 |
| 235 | 1 | 181 | 1 | 130 |
| 235 | 1 | 181 | 1 | 130 |
| 241 | 1 | 173 | 1 | 130 |
| 241 | 1 | 173 | 1 | 130 |
| 243 | 0 | 181 | 0 | 133 |
| 235 | 0 | 173 | 0 | 133 |
| 245 | 0 | 181 | 0 | 133 |
| 235 | 0 | 173 | 0 | 133 |
| 243 | 1 | 173 | 1 | 136 |
| 235 | 1 | 181 | 1 | 136 |
| 241 | 1 | 173 | 1 | 136 |
| 241 | 1 | 173 | 1 | 136 |
| 241 | 1 |  | 0 | 139 |
| 243 | 1 |  | 0 | 139 |
| 235 | 1 | 181 | 0 | 139 |
| 241 | 1 | 177 | 0 | 139 |
| 241 | 1 | 173 | 1 | 145 |
| 241 | 1 | 173 | 1 | 145 |
| 241 | 1 | 173 | 1 | 70 |
| 245 | 1 | 177 | 1 | 70 |
| 241 | 1 | 173 | 1 | 70 |
| 243 | 1 | 175 | 1 | 70 |
| 243 | 1 | 173 | 1 | 73 |
| 241 | 1 | 173 | 1 | 73 |
| 235 | 1 | 181 | 1 | 73 |
| 241 | 1 | 173 | 1 | 73 |
| 241 | 1 | 173 | 1 | 76 |
| 235 | 1 | 181 | 1 | 76 |

*FIG. 10F*

|  |  |  |  |  |  | controls |  |  |  |  |  |  |
|---|---|---|---|---|---|---|---|---|---|---|---|---|
| cont | sava5 | ca211 |  | ca212 |  | 1140 |  | 59 |  | ca231 |  | ta201 |
| 75 |  | 217 | 1 | 216 | 1 | 264 | 1 | 150 | 1 | 186 | 1 | 250 |
| 75 |  | 205 | 1 | 204 | 1 | 268 | 1 | 154 | 1 | 186 | 1 | 244 |
| 78 |  | 201 | 1 | 216 | 1 | 268 | 1 | 148 | 1 | 186 | 1 |  |
| 78 |  | 201 | 1 | 202 | 1 | 268 | 1 | 162 | 1 | 186 | 1 |  |
| 77 |  | 201 | 1 | 206 | 1 | 268 | 1 | 158 | 1 | 184 | 1 | 246 |
| 77 |  | 195 | 1 | 202 | 1 | 268 | 1 | 152 | 1 | 186 | 1 | 232 |
| 80 |  | 193 | 1 | 202 | 0 | 268 | 1 |  | 0 | 186 | 1 | 250 |
| 80 |  | 195 | 1 | 200 | 0 | 268 | 1 |  | 0 | 186 | 1 | 244 |
| 81 |  | 193 | 1 | 202 | 0 | 268 | 1 | 156 | 1 | 186 | 1 | 246 |
| 81 |  | 193 | 1 | 200 | 0 | 268 | 1 | 148 | 1 | 184 | 1 | 258 |
| 84 |  | 193 | 1 | 202 | 1 | 268 | 1 | 154 | 1 | 186 | 1 | 246 |
| 84 |  | 207 | 1 | 202 | 1 | 268 | 1 | 164 | 1 | 186 | 1 | 244 |
| 83 |  | 209 | 1 | 200 | 1 | 270 | 1 | 148 | 1 | 184 | 1 | 230 |
| 83 |  | 207 | 1 | 200 | 1 | 268 | 1 | 158 | 1 | 186 | 1 | 248 |
| 86 |  | 195 | 1 | 202 | 1 | 268 | 1 | 158 | 1 | 186 | 1 | 244 |
| 86 |  | 205 | 1 | 202 | 1 | 278 | 1 | 148 | 1 | 184 | 1 | 260 |
| 87 |  | 197 | 1 | 200 | 1 | 268 | 1 | 158 | 1 | 186 | 1 | 230 |
| 87 |  | 193 | 1 | 200 | 1 | 268 | 1 | 154 | 1 | 190 | 1 | 242 |
| 90 |  | 205 | 1 | 200 | 1 | 268 | 1 | 158 | 1 | 186 | 1 | 250 |
| 90 |  | 193 | 1 | 200 | 1 | 268 | 1 | 154 | 1 | 186 | 1 | 246 |
| 89 |  | 207 | 1 | 202 | 1 | 270 | 1 | 168 | 1 | 186 | 1 | 232 |
| 89 |  | 193 | 1 | 202 | 1 | 268 | 1 | 154 | 1 | 190 | 1 | 252 |
| 92 |  | 193 | 1 | 200 | 1 | 268 | 1 | 148 | 1 | 184 | 0 | 244 |
| 92 |  | 193 | 1 | 202 | 1 | 256 | 1 | 154 | 1 | 186 | 0 | 230 |
| 93 |  | 203 | 1 | 216 | 1 | 268 | 1 | 156 | 1 | 186 | 0 | 248 |
| 93 |  | 205 | 1 | 200 | 1 | 268 | 1 | 148 | 1 | 184 | 0 | 230 |
| 95 |  | 197 | 1 | 216 | 1 | 268 | 1 | 158 | 1 | 186 | 1 | 252 |
| 95 |  | 205 | 1 | 202 | 1 | 268 | 1 | 150 | 1 | 184 | 1 | 230 |
| 96 |  | 209 | 1 | 200 | 1 | 278 | 1 | 162 | 1 | 186 | 1 | 256 |
| 96 |  | 205 | 1 | 200 | 1 | 268 | 1 | 148 | 1 | 186 | 1 | 230 |
| 140 |  |  | 0 |  | 0 | 270 | 1 |  | 0 |  | 0 | 244 |
| 140 |  |  | 0 |  | 0 | 278 | 1 |  | 0 |  | 0 | 254 |
| 141 |  | 201 | 0 | 200 | 1 | 272 | 1 |  | 0 |  | 0 | 244 |
| 141 |  | 193 | 0 | 200 | 1 | 270 | 1 |  | 0 |  | 0 | 254 |

*FIG. 10G*

|   | at201 |   | ca225 |   | w3442 |   | ca213 |   | ga201 |   | ga203 |   |
|---|---|---|---|---|---|---|---|---|---|---|---|---|
| 1 | 170 | 1 | 180 | 1 | 12 | 1 | 124 | 1 | 150 | 1 | 192 | 1 |
| 1 | 170 | 1 | 172 | 1 | 16 | 1 | 124 | 1 | 146 | 1 | 192 | 1 |
| 0 | 174 | 1 | 172 | 1 |    | 0 | 124 | 1 | 150 | 1 | 192 | 0 |
| 0 | 170 | 1 | 174 | 1 |    | 0 | 126 | 1 | 150 | 1 | 188 | 0 |
| 1 | 170 | 1 | 160 | 1 | 22 | 1 | 124 | 1 | 150 | 1 | 192 | 0 |
| 1 | 178 | 1 | 174 | 1 | 20 | 1 | 122 | 1 | 146 | 1 | 188 | 0 |
| 1 | 178 | 1 | 160 | 1 | 10 | 1 | 124 | 1 | 150 | 1 | 208 | 1 |
| 1 | 178 | 1 | 172 | 1 | 28 | 1 | 124 | 1 | 150 | 1 | 208 | 1 |
| 1 | 194 | 1 | 172 | 1 | 10 | 1 | 126 | 1 | 150 | 1 | 188 | 1 |
| 1 | 186 | 1 | 174 | 1 | 10 | 1 | 124 | 1 | 150 | 1 | 208 | 1 |
| 1 | 170 | 1 | 172 | 1 | 14 | 1 | 126 | 1 | 158 | 1 | 188 | 1 |
| 1 | 170 | 1 | 178 | 1 | 10 | 1 | 124 | 1 | 150 | 1 | 188 | 1 |
| 1 | 178 | 1 | 172 | 1 | 26 | 1 | 124 | 1 | 150 | 1 | 208 | 1 |
| 1 | 170 | 1 | 174 | 1 | 10 | 1 | 112 | 1 | 146 | 1 | 192 | 1 |
| 1 | 170 | 1 | 160 | 1 | 14 | 1 | 124 | 1 | 158 | 1 | 208 | 1 |
| 1 | 170 | 1 | 172 | 1 | 20 | 1 | 120 | 1 | 150 | 1 | 188 | 1 |
| 1 | 178 | 1 | 172 | 1 | 10 | 1 | 124 | 1 | 158 | 1 | 188 | 1 |
| 1 | 170 | 1 | 172 | 1 | 16 | 1 | 126 | 1 | 154 | 1 | 188 | 1 |
| 1 | 170 | 1 | 172 | 1 | 18 | 1 | 124 | 1 | 158 | 1 | 208 | 1 |
| 1 | 186 | 1 | 172 | 1 | 10 | 1 | 124 | 1 | 150 | 1 | 188 | 1 |
| 1 | 178 | 0 | 176 | 1 | 22 | 1 | 126 | 1 | 154 | 1 | 212 | 1 |
| 1 | 170 | 0 | 172 | 1 | 16 | 1 | 126 | 1 | 150 | 1 | 188 | 1 |
| 1 | 170 | 0 | 174 | 1 | 10 | 1 | 124 | 1 | 150 | 1 | 208 | 1 |
| 1 | 178 | 0 | 172 | 1 | 10 | 1 | 124 | 1 | 154 | 1 | 188 | 1 |
| 1 | 170 | 1 | 174 | 1 | 14 | 1 | 126 | 1 | 150 | 1 | 204 | 1 |
| 1 | 178 | 1 | 174 | 1 | 10 | 1 | 126 | 1 | 150 | 1 | 188 | 1 |
| 1 | 178 | 1 | 174 | 1 | 20 | 1 | 126 | 1 | 150 | 1 | 192 | 0 |
| 1 | 178 | 1 | 160 | 1 | 10 | 1 | 126 | 1 | 150 | 1 | 188 | 0 |
| 1 | 170 | 1 | 160 | 1 | 14 | 1 | 128 | 1 | 150 | 1 | 192 | 0 |
| 1 | 178 | 1 | 160 | 1 | 14 | 1 | 128 | 1 | 150 | 1 | 188 | 0 |
| 1 |     | 0 |     | 0 | 10 | 1 |     | 0 | 150 | 1 | 188 | 1 |
| 1 | 186 | 1 |     | 0 | 10 | 1 |     | 0 | 158 | 1 | 188 | 1 |
| 1 | 170 | 1 | 172 | 1 | 10 | 1 |     | 0 |     | 0 | 216 | 1 |
| 1 | 170 | 1 | 160 | 1 | 10 | 1 |     | 0 |     | 0 | 212 | 1 |

*FIG. 10H*

| ca219 | | 1105 | 18SCA20 | SC | KID | |
|---|---|---|---|---|---|---|
| 241 | 1 | | 175 | 1 | 76 | controls |
| 235 | 1 | | 177 | 1 | 76 | |
| 241 | 1 | | 173 | 1 | 79 | |
| 241 | 1 | | 177 | 1 | 79 | |
| 241 | 1 | | 173 | 1 | 79 | |
| 241 | 1 | | 181 | 1 | 79 | |
| 241 | 1 | | | 0 | 82 | |
| 241 | 1 | | | 0 | 82 | |
| 241 | 1 | | 173 | 1 | 82 | |
| 241 | 1 | | 173 | 1 | 82 | |
| 241 | 1 | | 173 | 1 | 85 | |
| 241 | 1 | | 173 | 1 | 85 | |
| 241 | 1 | | 173 | 1 | 85 | |
| 241 | 1 | | 173 | 1 | 85 | |
| | 0 | | 173 | 1 | 88 | |
| | 0 | | 173 | 1 | 88 | |
| 235 | 1 | | 173 | 1 | 88 | |
| 235 | 1 | | 181 | 1 | 88 | |
| 245 | 1 | | 173 | 1 | 91 | |
| 241 | 1 | | 173 | 1 | 91 | |
| 241 | 1 | | 181 | 1 | 91 | |
| 241 | 1 | | 173 | 1 | 91 | |
| 241 | 1 | | 173 | 1 | 94 | |
| 241 | 1 | | 173 | 1 | 94 | |
| 241 | 1 | | 177 | 1 | 94 | |
| 235 | 1 | | 181 | 1 | 94 | |
| 241 | 1 | | 173 | 1 | 97 | |
| 245 | 1 | | 173 | 1 | 97 | |
| 221 | 1 | | 173 | 1 | 97 | |
| 241 | 1 | | 173 | 1 | 97 | |
| | 0 | | | 0 | 142 | |
| | 0 | | | 0 | 142 | |
| 241 | 1 | | 173 | 1 | 142 | |
| 241 | 1 | | 173 | 1 | 142 | |

*FIG. 10I*

| ca219 | | 1105 | 18SCA20 | SC | KID |
|---|---|---|---|---|---|
| 241 | 1 | | 177 | 1 | 145 |
| 235 | 1 | | 181 | 1 | 145 | controls

*FIG. 10K*

| cont | sava5 | ca211 | | ca212 | | 1140 | | 59 | | ca231 | | ta201 | | at201 | | ca225 | | w3442 | | ca213 | | ga201 | | ga203 | |
|---|---|---|---|---|---|---|---|---|---|---|---|---|---|---|---|---|---|---|---|---|---|---|---|---|---|
| 143 | | 193 | 1 | 200 | 1 | 278 | 1 | 148 | 1 | 184 | 1 | 252 | 1 | 170 | 1 | 184 | 1 | 18 | 1 | 124 | 1 | 150 | 0 | 192 | 1 |
| 143 | | 195 | 1 | 200 | 1 | 268 | 1 | 158 | 1 | 186 | 1 | 248 | 1 | | 1 | 178 | 1 | 18 | 1 | 124 | 1 | 146 | 0 | 188 | 1 | controls

*FIG. 10J*

AHR RESULTS IN DISEASE CHROMOSOMES

| | SAVA5 | CA211 | CA212 | 18S1140 | 18S59 | TA201 | CA231 | AT201 | CA225 | W3442 |
|---|---|---|---|---|---|---|---|---|---|---|
| SAVA5 | /// | 0.04<br>2% | | | 0.07<br>4% | | | | | |
| CA211 | 2-3 | /// | | | | | | | | |
| CA212 | | | /// | | | | | | | |
| 18S1140 | 2-6 | | | /// | 0.70<br>12% | 2.11<br>10% | 1.92<br>30% | | 1.28<br>20% | |
| 18S59 | | | | 2-4 | /// | | 2.45<br>18% | 0.53<br>10% | 1.16<br>12% | 4.18<br>17% |
| TA201 | | | | | | /// | 0.68<br>3% | 1.34<br>10% | 0.02<br>2% | 0.68<br>8% |
| CA231 | | | | 2-2 | 4-3 | 2-4 | /// | | 0.89<br>16% | |
| AT201 | | | | | 4-2 | 3-2 | 2-3 | /// | 0.18<br>4% | 0.03<br>4% |
| CA225 | | | | 2-3 | 4-2 | 3-3 | 2-1 | 1-1 | /// | |
| W3442 | | | | | 4-1 | 3-1 | 2-1 | 2-1 | | /// |

*FIG. 11*

METHODS FOR TREATING BIPOLAR MOOD DISORDER ASSOCIATED WITH MARKERS ON CHROMOSOME 18P

CROSS-REFERENCE TO RELATED APPLICATIONS

This application is a continuation application of U.S. application Ser. No. 08/916,683, filed Aug. 22, 1997, now abandoned, and claims the benefit of the filing date of United States Provisional Application Ser. No. 60/023,438, filed Aug. 23, 1996.

ACKNOWLEDGEMENTS

This invention was made with Government support under Grant Nos. RO1-MH49499, K21MH00916, awarded by the NIH. The U.S. Government has certain rights in this invention.

INTRODUCTION

Background

Bipolar Mood Disorder (BP)

Manic-depressive illness, or bipolar mood disorder (BP), is characterized by episodes of elevated mood (mania) and depression and is among the most prevalent and potentially devastating of psychiatric syndromes. The most severe and clinically distinctive forms of BP are BP-I (severe bipolar mood disorder) and SAD-M (schizoaffective disorder manic type), and are characterized by at least one full episode of mania, with or without episodes of major depression (defined by lowered mood, or depression, with associated disturbances in rhythmic behaviors such as sleeping, eating, and sexual activity). A milder form of BP is BP-II, bipolar mood disorder with hypomania and major depression. BP-I often co-segregates in families with more etiologically heterogeneous syndromes, such as unipolar major depressive disorder (MDD), which is a more broadly defined phenotype. See McInnes, L. A. and Freimer, N. B., Mapping genes for psychiatric disorders and behavioral traits, Curr. Opin. in Genet. and Develop., 5:376–381 (1995).

Treatment of Individuals With Bipolar Mood Disorder

An estimated 2–3 million people in the United States are affected by BP-I. Currently, individuals are typically evaluated for bipolar mood disorder using the clinical criteria set forth in the most current version of the American Psychiatric Association's *Diagnostic and Statistical Manual of Mental Disorders* (DSM). Many drugs have been used to treat individuals diagnosed with bipolar mood disorder, including lithium salts, carbamazepine and valproic acid. However, none of the currently available drugs is able to treat every individual diagnosed with severe BP-I (termed BP-I) and drug treatments are effective in only approximately 60–70% of individuals diagnosed with BP-I. Moreover, it is currently impossible to predict which drug treatments will be effective in particular BP-I affected individuals. Commonly, upon diagnosis affected individuals are prescribed one drug after another until one is found to be effective. Early prescription of an effective drug treatment is critical for several reasons, including the avoidance of extremely dangerous manic episodes and the risk of progressive deterioration if effective treatments are not found. Also, appropriate treatment may prevent depressive episodes in BP-I individuals; these episodes are also dangerous and are characterized by a high suicide rate. The high prevalence of the disorder, together with frequent occurrence of hospitalizations, psychosocial impairment, suicide and substance abuse, has made BP-I a major public health concern.

Genetic Basis for Bipolar Mood Disorder

Mapping genes for common diseases believed to be caused by multiple genes, such as BP-I, may be complicated by the typically imprecise definition of phenotypes, by etiologic heterogeneity and by uncertainty about the mode of genetic transmission of the disease trait. With psychiatric disorders there is even greater ambiguity in distinguishing between individuals who likely carry an affected genotype from those who are genetically unaffected. For example, one can define an affected phenotype for BP by including one or more of the broad grouping of diagnostic classifications that constitute the mood disorders: BP-I, SAD-M, MDD, and BP-II.

Thus, one of the greatest difficulties facing psychiatric geneticists is uncertainty regarding the validity of phenotype designations, since clinical diagnoses are based solely on clinical observation and subjective reports. Also, with complex traits such as psychiatric disorders, it is difficult to map the trait-causing genes genetically because: (1) the BP-I phenotype doesn't exhibit classic Mendelian recessive or dominant inheritance patterns attributable to a single genetic locus, (2) there may be incomplete penetrance i.e., individuals who inherit a predisposing allele may not manifest the disease; (3) the phenocopy phenomenon may occur, i.e., individuals who do not inherit a predisposing allele may nevertheless develop the disease due to environmental or random causes; (4) genetic heterogeneity may exist, in which case mutations in any one of several genes may result in identical phenotype.

The existence of one or more major genes associated with BP-I and with a clinically similar diagnostic category, SAD-M (schizoaffective disorder manic subtype), is supported by segregation analyses and twin studies (Bertelson et al., 1977; Freimer and Reus, 1992; Pauls et al., 1992). However, efforts to identify the chromosomal location of BP-I genes have yielded disappointing results in that reports of linkage between BP-I and markers on chromosomes X and 11 could not be independently replicated nor confirmed in the re-analyses of the original pedigrees (Baron et al., 1987; Egeland et al., 1987; Kelsoe et al., 1989; Baron et al., 1993). The possible localization of BP genes on chromosomes 18 (pericentromeric region) and 21q has been suggested, but in both cases the proposed candidate region is not well defined and there is equivocal support for either location (Berrettini et al. (1994) Proc. Natl. Acad. Sci. USA, 91, 5918–5921, Murray, J. C., et al. (1994) Science 265, 2049–2054; Pauls et al., Am. J. Hum. Genet. 57:636–643 (1995); Maier et al., Psych. Res. 59:7–15 (1995); Straub et al., Nature Genet., 8:291–296 (1994)). Recent investigations have led to the isolation of chromosome 18-specific brain transcripts which have been suggested to be positional candidates for bipolar disorder (Yoshikawa et al., Am. J. Med. Gen. 74, 140–149 (1997)).

Despite abundant evidence that BP has a major genetic component, linkage studies have not yet succeeded in definitively localizing a BP gene. This is mainly because mapping studies of psychiatric disorders have generally been conducted under a paradigm appropriate for mapping genes for simple Mendelian disorders, namely, using linkage analysis in the expectation of finding high lod scores that definitively signpost the location of disease genes. The follow up to early BP linkage studies, however, showed that even extremely high lod scores at a single location can be false positives. See Egeland, et al., Nature 325:783–787 (1987); Baron et al., Nature 326:289–292 (1987); Kelsoe et al., Nature, 342:238–243 (1989); and Baron et al., Nature Genet. 3:49–55 (1993). These earlier studies used largely uninformative markers and did not use stringent criteria for identifying affected individuals.

Linkage Disequilibrium Analysis

Linkage disequilibrium (LD) analysis is a powerful tool for mapping disease genes and may be particularly useful for investigating complex traits. LD mapping is based on the following expectations: for any two members of a population, it is expected that recombination events occurring over several generations will have shuffled their genomes, so that they share little in common with their ancestors. However, if these individuals are affected with a disease inherited from a common ancestor, the gene responsible for the disease and the markers that immediately surround it will likely be inherited without change, or IBD ("identical by descent"), from that ancestor. The size of the regions that remain shared (i.e. IBD) are inversely proportional to the number of generations separating the affected individuals and their common ancestor. Thus, "old" populations are suitable for fine scale mapping and recently founded ones are appropriate for using LD to roughly localize disease genes more approximately (Houwen et al., 1994, in particular FIG. 3 and accompanying text). Because isolated populations typically have had a small number of founders, they are particularly suitable for LD approaches; as indicated by several successful LD studies conducted in Finland (de la Chapelle, 1993).

LD analysis has been used in several positional cloning efforts (Kerem et al., 1989; MacDonald et al., 1992; Petrukhin et al., 1993; Hastbacka et al., 1992 and 1994), but in each case the initial localization had been achieved using conventional linkage methods. Positional cloning is the isolation of a gene solely on the basis of its chromosomal location, without regard to its biochemical function. Lander and Botstein (1986) proposed that LD mapping could be used to screen the human genome for disease loci, without conventional linkage analyses. This approach was not practical until a set of mapped markers covering the genome became available (Weissenbach et al., 1992). The feasibility of genome screening using LD mapping is now demonstrated by the applicants.

Identification of the chromosomal location of a gene responsible for causing severe bipolar mood disorder can facilitate diagnosis, treatment and genetic counseling of individuals in affected families.

Due to the severity of the disorder and the limitations of a purely phenotypic diagnosis of BP-I, there is a tremendous need to subtype individuals with BP-I genetically to confirm clinical diagnoses and to determine appropriate therapies based on their genotypic subtype.

SUMMARY OF THE INVENTION

The present invention comprises using genetic linkage and haplotype analysis to identify an individual having a bipolar mood disorder gene on the short arm of chromosome 18. In addition, the present invention provides markers linked to a gene responsible for susceptibility to bipolar mood disorder that will enable researchers to focus future analysis on that small chromosomal region and will accelerate the sequencing of a bipolar mood disorder gene located at 18p.

The present invention provides, for the first time, a localization of a BP-I susceptibility locus to a 300 to 500 kb region of the short arm of chromosome 18.

The present invention is directed to methods of detecting the presence of a bipolar mood disorder susceptibility locus in an individual, comprising analyzing a sample of DNA for the presence of a DNA polymorphism on the short arm of chromosome 18 between SAVA5 and ga203, wherein the DNA polymorphism is associated with a form of bipolar mood disorder. The invention includes the use of genetic markers in the roughly 500 kb region between the SAVA5 locus and the ga203 locus, inclusive, to diagnose bipolar mood disorder genetically in individuals and to confirm phenotypic diagnoses of bipolar mood disorder. Preferably, the sample of DNA is analyzed for the presence of a DNA polymorphism on the short arm of chromosome 18 in the roughly 300 kb region between D18S1140 and W3422.

In a further embodiment, the invention provides methods of classifying subtypes of bipolar mood disorder by identifying one of more DNA polymorphisms located within the 500 kb region between SAVA5 and ga203 loci, inclusive, on the short arm of chromosome 18 and analyzing DNA samples from individuals phenotypically diagnosed with bipolar mood disorder for the presence or absence of one or more of said DNA polymorphisms. Preferably, the sample of DNA is analyzed for the presence or absence of one or more of said DNA polymorphisms in the roughly 300 kb region between D18S1140 and W3422 on the short arm of chromosome 18.

In yet a further embodiment, the methods of the invention include a method of treating an individual diagnosed with bipolar mood disorder comprising identifying one or more DNA polymorphisms located within the 500 kb region of chromosome 18 between SAVA5 and ga203, analyzing DNA samples from individuals phenotypically diagnosed with bipolar mood disorder for the presence or absence of one or more of the DNA polymorphisms, and selecting a treatment plan that is most effective for individuals having a particular genotype within the 500 kb region of chromosome 18 between SAVA5 and ga203. Preferably, the sample of DNA is analyzed for the presence or absence of one or more DNA polymorphisms in the roughly 300 kb region between D18S1140 and W3422 on the short arm of chromosome 18.

BRIEF DESCRIPTION OF THE DRAWINGS

FIG. 2 is a table of lod scores for markers covering the entire human genome that exceeded the arbitrary coverage thresholds. Lod scores are shown for two markers on chromosome 18: D18S59 and D18S1105.

FIGS. 6A, 6B and 6C are a list of markers on chromosome 18, with map positions noted.

FIG. 7 describes 18p allele frequencies for disease chromosomes (aff 105) versus nontransmitted chromosomes (ntrans) and samples from a control population of Costa Rican students and their parents (control). The name of each marker used in this study is indicated on the left. The second column of numbers refers to allele length in base pairs.

FIG. 8 depicts haplotype analysis of individuals affected with BP-I. The column labelled 18p refers to the patient identifier, and each patient identifier is repeated with 2 rows to indicate allele results with each of the patient's two copies of chromosome 18. The columns labelled "PANR" and "MANR" refer to the paternal and maternal identifiers, respectively, associated with the particular patient, other than 0, 1 and 2, which indicate that parental samples were not available. The column headings to the right of "PANR" and "MANR" columns represent names of specific markers in the 18p region that were used in the haplotype analysis. The markers are listed in the order they appear on chromosome 18. The allele length (in base pairs) is indicated under the column heading each marker for a particular patient. In the column to the immediate right of each marker column, a "1" indicates that the phase is known, i.e., that it is known whether a particular allele is inherited from the paternal or maternal chromosome, and a "0" indicates that the phase is not definitely known. The shaded horizontal bars depict haplotypes of at least three markers which include a 154 allele length at D18S59, other than patients 218, 225, 232, 234, 311, 314 and 458, where the stippled region depicts small sections that do not have the 154 allele at D18S59. The hatched regions depict uncertainty as to whether the individual has the affected haplotype, as the phase is not known with certainty. In addition, the presence of an allele length of 232 (or 234) with marker ta201 is thought to result from a highly mutable allele and may not be distinct from the 230 allele. Similarly, the 202 allele at ca212 may not be distinct from the 200 allele at ca212. Patients 246, 247, 248, 311, 316, 367, 384, 501, 531, 587, 536, 684, 667 and 669 exhibit a 242, 244, 250, 252 or 214 allele at marker ta201 which indicates a potential marker location. Patients 488, 435 and 236 exhibit haplotypes that are distinct from the pedigrees that were analyzed.

FIG. 9 depicts haplotype analysis of nontransmitted chromosomes from parents of individuals affected with BP-I. The labels "ERSN" and "KID" refer to the parental and patient identifiers, respectively. As above, allele length is provided in base pairs below each marker with an indication as to whether phase was known (1) or not known (0) given to the right of these values. The markers, shading and allele characteristics described for FIG. 8 also apply to this figure.

FIG. 10 depicts haplotype analysis of control samples obtained from an unscreened population of students of the University of Costa Rica and their parents representing the general population. Identifiers are provided in the column headed "cont", allele length and phase determination given in the remainder of the table. The markers, shading and allele characteristics described for FIG. 8 also apply to this figure. Complete data for all markers are not given as indicated by blank boxes, or the terms "miss" or "missing".

FIG. 11 depicts Ancestral Haplotype Reconstruction results in disease chromosomes.

DESCRIPTION OF SPECIFIC EMBODIMENTS

Figure 1A:
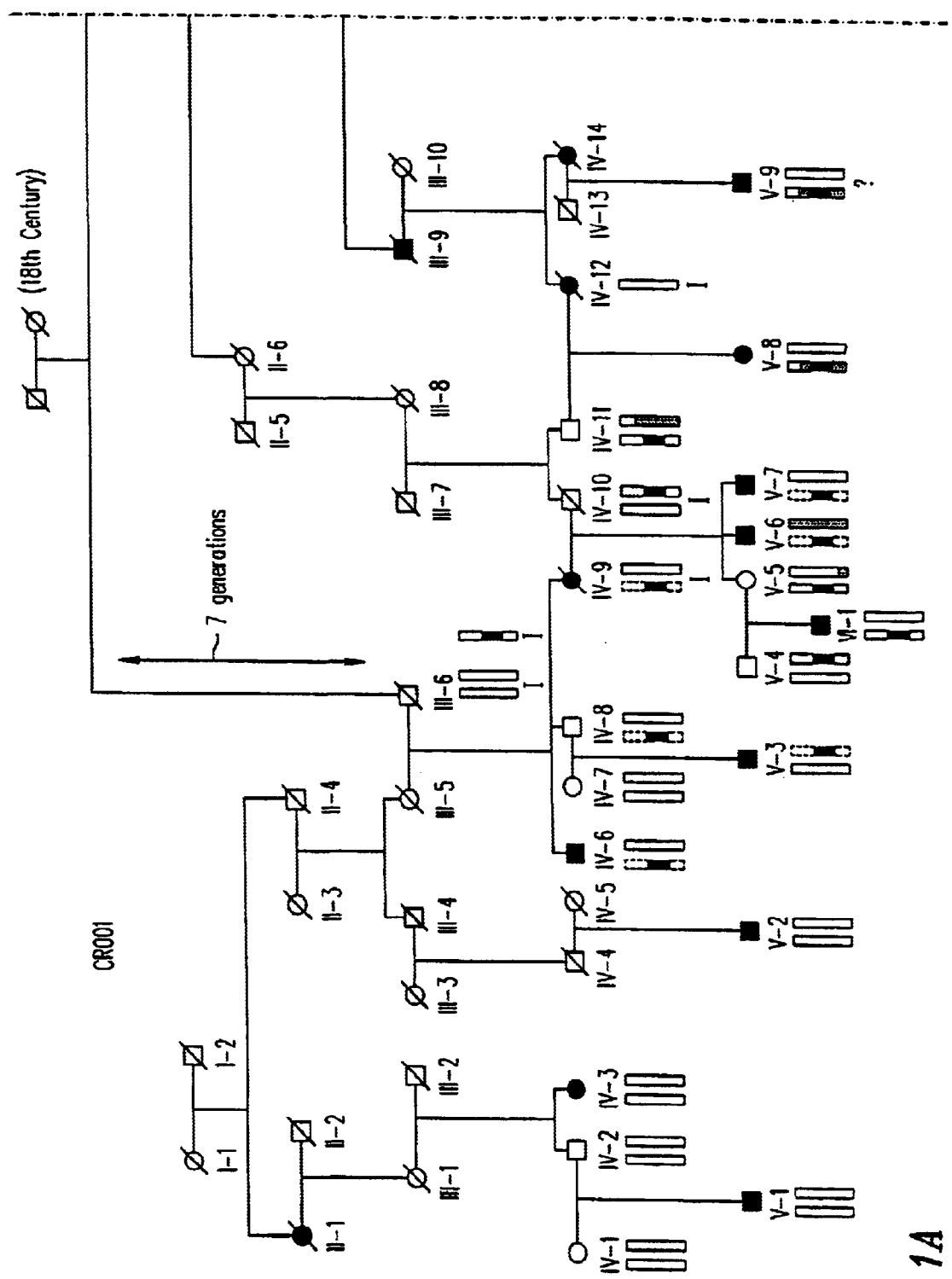
FIG. 1 is a pedigree chart showing two families, CR001 and CR004. Affected individuals are denoted by black symbols, deceased individuals by a diagonal slash. A schematic of each individual's haplotype (where available) is shown below the ID number. Recombinations are denoted by "-x"; consanguineous marriages by a double bar, and the conserved haplotype as black shading within the haplotype bars. The larger conserved region for CR004 is stippled, the larger conserved region for CR001 is indicated by a dashed outline. An "I" underneath the haplotype bars indicates inferred haplotype. A "?" indicates phase is uncertain. The connection between CR001 and CR004, dating to an 18th Century founding couple, is indicated by the dashed lines joining individuals III-6 and I-4.

The recent availability of highly polymorphic, genetically mapped markers covering the human genome (Weissenbach, J., et al. (1996) Nature 359, 794–801, Murray, J. C., et al. (1994) Science 265, 2049–2054, Gyapay, G., et al. (1994) Nature Genet 7,246–339) has allowed the development of a multi-stage paradigm for mapping genes for complex traits. In the first stages, complete genome screening (e.g. through lod score analysis) is used to identify possible localizations for disease genes. Subsequently, the regions highlighted by the screening study are more intensively investigated to confirm the initial localizations and delineate clear candidate regions. Finally, fine mapping methods (such as haplotype or linkage disequilibrium (LD) analysis) or candidate gene approaches are used for positional cloning of disease genes.

Our genome screening study for BP employed the following strategies. Unlike previous genetic studies of BP, only those individuals with the most severe and clinically distinctive forms of BP (BP-I and schizoaffective disorder manic type, SAD-M) were considered as affected, rather than including those diagnosed with a milder form of BP (BP-II) or with unipolar major depressive disorder (MDD). Two large pedigrees (CR001 and CR004) were selected from a genetically homogeneous population, that of the Central Valley of Costa Rica (as described in Escamilla, M. A., et al., (1996) Neuropsychiat. Genet. 67, 244–253, and in Freimer, N. B., et al. (1996) Neuropsychiat. Genet. 67, 254–263, both incorporated by reference herein). The entire human genome was screened for linkage using mapped microsatellite markers and a model for genetic analysis in which most of the linkage information was derived from affected individuals. The goal of this stringent linkage analysis was to identify all regions potentially harboring major genes for BP-I in the study population. Empirically determined lod score thresholds (using linkage simulation analyses) were derived, to suggest regions worthy of further investigation.

Identification of all suggestive regions and weighing the relative importance of findings required complete screening of the genome. The coverage approach was developed to gauge the progress of this effort. Conventionally, the thoroughness of genome screening is evaluated by excluding genome regions from linkage under given genetic models. This approach, which is highly sensitive to misspecification of genetic models, may be poorly suited for genome screening studies of complex traits; it is tied to the expectation of finding linkage at a single locus and demonstrating absence of linkage at all other locations in the genome. Additionally, exclusion analyses do not differentiate between genome regions where linkage is not excluded because markers are uninformative in the study population from those in which the genotype data are simply ambiguous. In contrast, the coverage approach is designed for studies aimed at genome screening rather than for studies where the goal is to demonstrate a single unequivocal linkage finding, and it provides explicit data regarding the informativeness of markers in the study pedigrees. Its use lessens the possibility that one would prematurely dismiss a given genome region as being unpromising for further study.

Because the exact genetic length of chromosomes is not clearly established, it is impossible to be certain that one has screened the entire genome. Although we report coverage of about 94% of the genome (under the 90%) dominant model) at the thresholds described above, this probably represents an underestimate. The remaining coverage gaps in our study occur predominantly at or near telomeres; as the upper bound estimates for the length of each chromosome were used, it is likely that the actual coverage gaps in these regions are smaller than our conservative assessment.

The presence of consistently positive lod scores over a given region was considered to be of greater significance than isolated peak lod scores. Such clustering suggests true co-segregation of markers and phenotypes (i.e. alleles are shared identically by descent rather than identically by state) and is more readily observed in analyses of a few large pedigrees (as in our study) than in examination of several smaller families. The data presented herein indicates clustering of positive lod scores in the region of the telomere of 18p.

The genome screen was conducted in two stages. The Stage I screen identified areas suggestive of linkage, so that those areas could be saturated with available markers, and so that regions, referred to as 'coverage gaps', could be pinpointed where markers were insufficiently informative in our sample to detect evidence of linkage. The Stage II screen followed up on regions flanking each marker that yielded peak lod scores approximately equal to or greater than the thresholds used for the coverage calculations, which were deemed regions of interest, and filled in coverage gaps. The results of the complete genome screen (Stages I and II) using 473 markers is described below.

In addition, linkage disequilibrium analysis of an independently collected sample of 48 unrelated BP-I patients was initially conducted. These patients were from the same ancestral population as the patients in the CR001 and CR004 pedigrees. The LD analysis was conducted with markers on the short arm of chromosome 18 (18p), in a 5 centimorgan (cM) region ("5 cM 18pter region") extending from the end of the 18p telomere to a distance of 5 cM along the short arm of chromosome 18 (18p). The LD analysis gave evidence of LD in this region, particularly at marker D18S59 and also at D18S476. LD analysis of further BP-I patients from the CRCV with markers in this 5 cM 18pter region was conducted to confirm and fine map a BP-I gene in this region. This approach, using additional BP-I patients from this CRCV population and additional markers identifies the region of maximum LD and can precisely localize a BP-I susceptibility gene.

Fine mapping of 5 cM 18pter region resulted in the identification of two DNA markers (D18S1140 and W3422) defining the boundaries of BP-I as approximately 300 kb, thus allowing a systematic search for the BP-I gene(s).

A conservative approach to linkage analysis was used in that almost all of the information for linkage is derived from individuals with a severe, narrowly defined phenotype. While this approach made it very unlikely that lod scores greater than conventional thresholds of statistical significance (e.g. $\leq 3$) would be obtained, it provided confidence in the robustness of the most suggestive findings.

Direct cDNA selection can be used to isolate segments of expressed DNA from the 300 kb region between D18S1140 and W3422 (M. Lovett, J. Kere, L. M. Hinton, Proc. Natl. Acad. Sci. USA 88 9628–9632 (1991); Y.-S. Jou et al., Genomics 24 410–413 (1994)). By using bacterial artificial chromosomes (BAC) (e.g., commercially available from Research Genetics Inc. Huntsville, Ala.), a group of cDNAs can be identified, and hybridization and PCR-amplification experiments can be used to determine if these cDNA segments are derived from the 300 kb region.

The cDNAs can then be used to determine whether specific sequences are expressed at lower levels (or not at all) in affected individuals compared to non-carrier individuals. Measurement of mRNA levels in lymphoblastoid cell lines can be used as an initial screen. The cell lines are prepared by drawing blood from individuals, transforming the lymphoblasts with EBV and growing the immortalized cells in culture. Total RNA and DNA are extracted from the cultured human lymphoblastoid cell lines. Northern blot hybridization is used to determine reduced levels of a specific sequence compared to levels from an unaffected, non-carrier individual as a result of mutations in the BP-I gene on the chromosomes from these affected individuals which results in decreased levels of mature mRNA and play a primary role in BP-I. Thus, alterations in gene sequences in affected individuals can be determined.

The polymerase chain reaction (PCR) is used to amplify the gene and to determine its sequence from affected individuals. Sequence comparison with unaffected, non-carrier individuals is carried out to identify polymorphisms in the gene sequence that are responsible for BP-I.

The identification of the biochemical defect that causes BP-I provides a basis for treatments for this disease. In addition, knowledge that certain mutations in the gene are responsible for the disease allows mutation detection tests to be used as a definitive diagnosis for BP-I.

Thus, the present invention allows the isolation of a nucleic acid molecule that can be used in the identification of the presence (or absence) of a mutation in the BP-I gene a human and thus can be used in the diagnosis of BP-I or in the genetic counseling of individuals, for example those with a family history of BP-I (although the general population can be screened as well). In particular, it should be noted that any mutation in the BP-I gene away from the normal gene sequence is an indication of a potential genetic flaw; even so-called "silent" mutations that do not encode a different amino acid at the location of the mutation are potential disease mutations, since such mutations can introduce into (or remove from) the gene an untranslated genetic signal that interferes with the transcription or translation of the gene. Thus, advice can be given to a patient concerning the potential for transmission of BP-I if any mutation is present. While an offspring with the mutation in question may or may not have symptoms of BP-I, patient care and monitoring can be selected that will be appropriate for the potential presence of the disease; such additional care and/or monitoring can be eliminated (along with the concurrent costs) if there are no differences from the normal gene sequence. As additional information (if any) becomes available (e.g., that a given silent mutation or conservative replacement mutation does or does not result in BP-I), the advice given for a particular mutation may change. However, the change in advice given does not alter the initial determination of the presence or absence of mutations in the gene causing BP-I.

Generally, mutations are identified in the human gene for use in a method of detecting the presence of a genetic defect that causes or may cause BP-I, or that can or may transmit BP-I to an offspring of the human. Initially, the practitioner will be looking simply for differences from the sequence identified as being normal and not associated with disease, since any deviation from this sequence has the potential of causing disease, which is a sufficient basis for initial diagnosis, particularly if the different (but still unconfirmed) gene is found in a person with a family history of BP-I. As specific mutations are identified as being positively correlated with BP-I (or its absence), practitioners will in some cases focus on identifying one or more specific mutations of the gene that changes the sequence of a protein product of the gene or that results in the gene not being transcribed or translated. However, simple identification of the presence or absence of any mutation in the gene of a patient will continue to be a viable part of genetic analysis for diagnosis, therapy and counseling.

The actual technique used to identify the gene or gene mutant is not itself part of the practice of the invention. Any of the many techniques to identify gene mutations, whether now known or later developed, can be used, such as direct sequencing of the gene from affected individuals, hybridization with specific probes, which includes the technique known as allele-specific oligonucleotide hybridization, either without amplification or after amplification of the region being detected, such as by PCR. Other analysis techniques include single-strand conformation polymorphism (SSCP), restriction fragment length polymorphism (RFLP), enzymatic mismatch cleavage techniques and transcription/translation analysis. All of these techniques are described in a number of patents and other publications; see, for example, "Laboratory Protocols for Mutation Detection" (1996) Oxford University Press, Editor; Ulf Landegrun.

Depending on the patient being tested, different identification techniques can be selected to achieve particularly advantageous results. For example, for a group of patients known to be associated with particular mutations of the gene, oligonucleotide ligation assays, "mini-sequencing" or allele-specific oligonucleotide (ASO) hybridization can be used. For screening of individuals who are not known to be associated with a particular mutation, single-strand conformation polymorphism, total sequencing of genetic and/or cDNA and comparison with standard sequences are preferred.

In many identification techniques, some amplification of the host genomic DNA (or of messenger RNA) will take place to provide for greater sensitivity of analysis. In such cases it is not necessary to amplify the entire gene, merely the part of the gene or the specific location within the gene that is being detected. Thus, the method of the invention generally comprises amplification (such as via PCR) of at least a segment of the gene, with the segment being selected for the particular analysis being conducted by the diagnostician.

The patient on whom diagnosis is being carried out can be an adult, as is usually the case for genetic counseling or a newborn, or prenatal diagnosis can be carried out on a fetus. Blood samples are usually used for genetic analysis of adults or newborns (e.g., screening of dried blood on filter paper), while samples for prenatal diagnosis are usually obtained by amniocentesis or chorionic villus biopsy.

Prior to the present invention, affected individuals were prescribed one drug after another until one was found to be effective. As BP-I was diagnosed using clinical criteria, no correlation between using a particular drug and its efficacy in a given case was observed. As a result of the present invention, BP-I subtypes can be diagnosed at the molecular level and effective treatment predicted.

For example, lithium salts, carbamazepine and valproic acid have all been prescribed for BP-I affected individuals with serendipitous results. An individual can now be diagnosed with bipolar mood disorder by analyzing genetic material from that individual for the presence or absence of one or more nucleic acid mutations as described above. As a result of this diagnosis at the molecular level, an effective treatment can be determined by collecting data to obtain a statistically significant correlation of a particular treatment with the different subtypes of BP-I. Thus, the practitioner is able to select a specific drug for the treatment of a particular sub-type of BP-I and does not merely rely on trial and error.

Alternatively, the full-length normal genes for BP-I from humans, as well as shorter genes that produce functional proteins, can be used to correct BP-I in a human patient by supplying to the human an effective amount of a gene product of the human gene, either by gene therapy or by in vitro production of the protein followed by administration of the protein. It should be recognized that the various techniques for administering genetic materials or gene products are well known and are not themselves part of the invention. The invention merely involves supplying the genetic materials or proteins identified as a result of the present invention in place of the genetic materials or proteins previously administered. For example, techniques for transforming cells to produce gene products are described in U.S. Pat. No. 5,283,185 entitled "Method for Delivering Nucleic Acid into Cells," as well as in numerous scientific articles, such as Felgner et al., "Lipofection: A Highly Efficient, Lipid-Mediated DNA-Transfection Procedure," *Proc. Natl. Acad. Sci. U.S.A.*, 84, 7413–7417 (1987); techniques for in vivo protein production are described in, for example, Mueller et al., "Laboratory Methods—Efficient Transfection and Expression of Heterologous Genes in PC12 Cells," *DNA and Cell Biol.*, 9(3), 221–229 (1990).

Administration of proteins and other molecules to overcome a deficiency disease is well known (e.g., administration of insulin to correct for high blood sugar in diabetes) that further discussion of this technique is not necessary. Some modification of existing techniques may be required for particular applications, but those modifications are within the skill level of the ordinary practitioner using existing knowledge and the guidance provided in this specification.

The invention now being generally described, the following examples are provided for purposes of illustration only and are not to be considered to limit the invention.

EXAMPLES

Pedigrees

Two independently ascertained Costa Rican pedigrees. (CR001 and CR004) were chosen because they contained a high density of individuals with BP-I and because their ancestry could be traced to the founding population of the Central Valley of Costa Rica. The current population of the Central Valley (consisting of about two million people) is predominantly descended from a small number of Spanish and Amerindian founders in the 16th and 17th centuries (Escamilla, M. A., et al., (1996) Neuropsychiat. Genet. 67, 244–253). Studies of several inherited diseases have confirmed the genetic isolation of this population (Leon, P., et al. (1992) Proc. Natl. Acad. Sci. USA. 89, 5181–5184; Uhrhammer, N., et al. (1992) Am. J. Hum. Genet. 57, 103–111). An extensive description of pedigrees CR001 and CR004 has ben published (Freimer, N. B., et al. (1996)

Neuropsychiat. Genet. 67, 254–263). In the course of the study, two links between these pedigrees were discovered. However, the families were analyzed separately because these links were discovered after the simulation analyses were completed and after the genome screening study had been initiated.

All available adult members of these families were interviewed in Spanish using the Schedule for Affective Disorders and Schizophrenia Lifetime version (SADS-L) (Endicott, J. et al, (1978) Arch. Gen. Psych. 35, 837–844). Individuals who received a psychiatric diagnosis were interviewed again in Spanish by a research psychiatrist using the Diagnostic Interview for Genetic Studies (DIGS) (Nurnberger, J. L. et al. (1994) Arch. Gen. Psychiat. 51, 849–859). This recently developed instrument is similar to, but more detailed than SADS-L. The interviews and medical records were then reviewed by two blinded best estimators who reached a consensus diagnosis. The diagnostic procedures are described in detail in Freimer, N. B., et al. (1996) Neuropsychiat. Genet. 67, 254–263 (incorporated by reference herein).

Unrelated CRCV BP-I Patient Study

BP localizations obtained through the CRCV pedigree studies were confirmed by genotyping an independently collected sample of 48 unrelated BP-I patients from the CRCV. In this fine mapping LD analysis, 48 unrelated BP-I patients from the CRCV were identified and genotyped using microsatellite markers spaced at narrow intervals across chromosome 18. As these patients are descended from the same ancestral population as the patients in the pedigrees previously studied (CR001 and CR004), many of them should share disease susceptibility alleles inherited identically by descent (IBD) from one or a few common ancestors, and linkage disequilibrium (LD) should be present at marker loci surrounding the disease genes.

The sample of 48 BP-I patients included 25 women and 23 men who were recruited from psychiatric hospitals and clinics in the CRCV. These patients were ascertained only on the basis of diagnosis and CV ancestry, and were not selected on the basis of history of BP illness in family members. A structured interview of each patient was conducted by a psychiatrist, and medical and hospital records were collected. Ascertainment and diagnostic procedures were as described above. However, in order to lessen further the probability of phenocopies among this unrelated sample, for which we lacked pedigree information, the affected phenotype was defined even more narrowly than in the pedigree study. Individuals considered affected in this study had to have suffered at least two disabling episodes of mania (requiring hospitalization) and a first onset of the illness before age 45.

Genealogical research on each of the 48 BP-I patients confirmed that on average, 70% of their great-grandparents were born in the CRCV. Individuals whose great-grandparents were born in the CRCV were considered likely to be descended from the original Spanish and Amerindian founders of the CRCV. Genealogical research showed that 2 patients are first cousins and the remaining 46 have no relationship within the past 4 generations.

Genotyping Pedigree Studies

Linkage simulations were used to select the most informative individuals from pedigrees CR001 and CR004 for genotyping studies (Freimer, N. B., et al. (1996) Neuropsychiat. Genet. 67, 254–263). Under a 90% dominant model, simulation analyses with these individuals suggested that evidence of linkage would likely be detected (e.g. a probability of 92% of obtaining lod>1.0 in the combined data set) using markers with an average heterozygosity of 0.75 spaced at 10 cM intervals (as discussed in Freimer, N. B., et al. (1996) Neuropsychiat. Genet. 67, 254–263). For the Stage I screen, the most polymorphic markers (307 in total) were chosen, placed at approximately 10 cM intervals on the 1992 Genethon map (Houwen, R., et al. (1992) Nature 359, 794–801). These markers were then supplemented by a small number of markers from the Cooperative Human Linkage Center (CHLC) public database. For the Stage II screen, 166 markers were added from newer Genethon and CHLC maps as they became available (Murray, J. C. et al. (1994) Science 265, 2049–2054, Gyapay, G., et al. (1994) Nature Genet. 7,246–339) and from the public database of the Utah Center for Genome Research, all of which are publicly available. DNA samples (from individuals in the CEPH families) that were used for size standards for Genethon and CHLC markers were included in the experiments to permit comparison of allele sizes between members of the CRCV population and individuals in the CEPH database. Genotyping procedures were as described previously (DiRienzo, A. et al. (1994) Proc. Natl. Acad. Sci. USA 91, 3166–3170 (incorporated by reference herein)). Briefly, one of the two PCR primers was labeled radioactively using a polynucleotide kinase and PCR products were run on polyacrylamide gels. Autoradiographs were scored independently by two raters. Data for each marker were entered into the computer database twice and the resultant files were compared for discrepancies.

Genotyping of Unrelated BP-I CRCV Patients

Twenty-seven markers were used to genotype all 48 individuals (as well as 53 individuals used to establish genetic phase) at approximately 5 cM intervals along the entire chromosome 18. It was hypothesized that such a screen would permit the evaluation of evidence in the 18pter region and also to investigate other regions on chromosome 18 in which linkage to BP has been suggested by other groups in other populations. For each individual, two-marker haplotypes in each of the 26 inter-marker intervals were investigated. For 38 of the 48 BP-I patients, genotypes of parents or children were available to assist in phase determination. Because of phase ambiguities in the remaining 10 individuals, minimal and maximal two-marker haplotype sharing was evaluated as follows: (1) Minimal: the number of individuals (and chromosomes) who definitely shared a chromosomal segment defined by a particular pair of alleles (phase known chromosomes) and (2) Maximal: the number of individuals (and chromosomes) who could possibly share a chromosomal segment defined by a particular pair of alleles (includes phase unknown chromosomes). The threshold used to identify areas of high IBD sharing of chromosomes in this initial screen was designated as maximal sharing of a two-marker haplotype by 50% or more of the 48 individuals (or 25% or more of the 96 chromosomes).

Arbitrary thresholds were designated to identify possible areas of high IBD sharing among the 48 patients. Eight of the 26 regions passed this screen. Within each of these 3 regions, one to three additional markers were typed to permit detection of LD, if present, over regions of one to two cM.

A total of 42 chromosome 18 markers were used to genotype the study sample: D18S1140, D18S59, D18S476, D18S481, D18S391, D18S452, D18S843, D18S464, D18S1153, D18S378, D18S53, D18S453, D18S40, D18S66, D18S56, D18S57, D18S467, D18S460, D18S450, D18S474, D18S69, D18S64, D18S1134, D18S1147, D18S60, D18S68, D18S55, D18S477, D18S61, D18S488, D18S485, D18S541, D18S870, D18S469, D18S874, D18S380, D18S1121, D18S1009, D18S844, D18S554, D18S461, D18S70 (from pter to qter). Of these 42 markers, four are located within the 5 cM 18pter region extending from the telomere of 18p to marker D18S481 (inclusive), which is approximately 5 cM from the telomere of 18p. This region is referred to as the 5 cM 18pter region. The four markers tested in the 5 cM 18pter region are: D18S59, D18S1140, D18S476 and D18S481.

For each marker the likelihood that a particular allele (or alleles) is over-represented on disease chromosomes, as compared to nondisease chromosomes was evaluated. The results of this likelihood test provide a conservative but powerful measure of LD between two loci.

Pedigree Statistical Analysis

Two-point linkage analyses were performed for all markers. Marker allele frequencies were estimated from the combined data set with correction for dependency due to family relationships (Boehnke, M. (1991) Am. J. Hum. Genet. 48, 22–25). Me linkage analyses for Stages I and II included the 65 individuals who were genotyped as well as an additional 65 individuals who had been diagnostically evaluated but not genotyped. Only individuals with BP-I were considered affected with the exception of two persons, one in each family, who carry diagnoses of schizoaffective disorder manic type (SAD-M). The SAD-M individuals were included as affected because BP-I and SAD-M are often difficult to distinguish from each other based on their clinical presentation and course of illness (Goodwin, F. K. et al. (1990) in Manic Depressive Illness (Oxford University Press, New York), pp. 373–401; Freiner, N. B et al. (1993) in The Molecular and Genetic Basis of Neurological Disease, pp. 951–965; Freimer, N. B. et al. (1996) Neuropsychiat. Genet. 67, 254–263; and Freimer, N. B. et al (1996) Nature Genetics 12:436–441, all incorporated by reference herein). In all, 20 individuals were designated as affected within CR004 (Copeman, J. B., et al. (1995) Nature Genet. 9, 80–85 available for genotyping) and 10 individuals from CR001 (Kelsoe, J. R. et al. (1989) Nature 342, 238–243 available for genotyping). The phenotype for all other individuals was designated as unknown except for 17 individuals who were designated as unaffected because they had been thoroughly clinically evaluated, showed no evidence of any psychiatric disorder, and were well beyond the age of risk (50) for BP-I (linkage simulation studies indicated that these unaffected individuals contributed little information to the linkage analysis).

Linkage analyses were performed using a nearly dominant model (assuming penetrance of 0.81 for heterozygous individuals of 0.9 for homozygotes with the disease mutation). This model was chosen from five different single-locus models (ranging from recessive to nearly dominant) due to its consistency with the segregation patterns of BP in the two pedigrees and because it had demonstrated the greatest power to detect linkage in simulation studies (Freimer, N. B., et al. (1996) Neuropsychiat. Genet. 67, 254–263). Based on Costa Rican epidemiological surveys Escamilla, M. A., et al., (1996) Neuropsychiat. Genet. 67, 244–253, the population prevalence of BP-I was assumed to be 0.015 (and thus the frequency of the disease allele was assumed to be 0.003)(based on epidemiological surveys in Costa Rica, Adis, G. (1992) "Disordenes mentales en Costa Rica: Observaciones Epidemiologicas," (San Jose, Costa Rica: Editorial Nacional de Salud y Seguridad Social)). The frequency of BP-I in individuals without the disease allele was conservatively set at 0.01 which effectively specified a population phenocopy rate of 0.67 (i.e., an affected individual in the general population has a $\frac{2}{3}$ probability of being a phenocopy). For multiply affected families, the probability that a gene segregates is highly increased, which implies that affected individuals in our study pedigree have a lower probability to be phenocopies than affected individuals in the general population, particularly those with several affected close relatives (the exact probabilities are dependent on the degree of relationship between patients and the number of intervening unaffected individuals). These parameters were chosen to ensure that most of the linkage information derives from affected individuals. The rationale for selecting these parameters and results of analyses that demonstrate the conservatism of this model are described by Freimer, N. B., et al. (1996) Neuropsychiat. Genet. 67, 254–263. The LINKAGE package (Lathrop et al., (1984) Proc. Natl. Acad. Sci. USA 81, 3443–3446) was used for lod score analysis and to obtain maximum likelihood estimates of the marker allele frequencies, taking into account the existing family relationships (see Boehnke, Am. J. Hum. Gent. 48, 22–25 (1991)).

Unrelated BP-I CRCV Patient Statistical Analysis

A likelihood test of disequilibrium (J. Terwilliger, Am. J. Hum. Genet. 56, 777 (1995)) was used to estimate a single parameter, lambda, that quantifies the over-representation of marker alleles on disease chromosomes as compared to non-disease chromosomes. We chose this method of analysis over another commonly used disequilibrium analysis method, the transmission disequilibrium test (TDT, R. Spielman et al., Am. J. Hum. Genet. 52, 506 (1993)) because data from all 48 BP-I patients could be used in the likelihood approach. Effective use of the TDT requires phase-known, heterozygous parental chromosomes. We do not have parental genotypes for 20 of the 48 BP-I patients. Simulations indicated that with our data, the likelihood test of disequilibrium would be more powerful than the TDT. Lambda has been shown to be a superior measure for LD fine mapping, compared to other frequently used measures, because it is directly related to the recombination fraction between the disease and the marker loci. Non-disease chromosomes were chosen from the phase-known chromosomes of parents, spouses and children of affected individuals, if available. Designation of chromosomes of family members as non-disease in a disorder such as: BP-I, which is not fully penetrant, necessitates specifying a model of disease transmission. The same model of transmission was employed in this LD likelihood test as was used in the initial genome screen of the pedigrees CR001 and CR002 described herein. One parameter was specified differently from the genome screen: the phenocopy rate was set to zero in the LD likelihood analysis. A phenocopy rate was not specified in the transmission model because the effect of phenocopies will be "absorbed" by the lambda parameter, in that presence of phenocopies in our sample will serve to erode the association between marker alleles and disease, and hence reduce the estimate of lambda.

Coverage

To access coverage for a marker, the number of informative meioses at the estimated recombination fraction was calculated using the estimate of the variance (the inverse of the information matrix) (Petrukhin, K. E. et al. (1993) Genomics 15, 76–85). Alternatively, when the estimated frequency of recombination was close to 0 or 1, Edwards' equation was applied to calculate the equivalent number of observations (Edwards, J. H. (1971) Ann. Hum. Genet. 34, 229–250). These meioses represent the amount of linkage information provided by the marker, given the pedigree structure and the genetic model applied. Linkage to the marker in question was then assumed and the lod score that would be observed as a disease gene is hypothetically moved in increments away from that marker was calculated. All regions around a marker that would have generated a lod score that exceeded our thresholds for possible linkage (0.8 in CR001, 1.2 in CR004, and 1.6 in the combined data) were considered covered, These lod score thresholds were derived from simulation analyses showing the expected distribution of lod scores under linkage and non-linkage (Freimer, N. B., et al. (1996) Neuropsychiat. Genet. 67, 254–263, and approximately represent a result that is 250 times more likely to occur in linked simulations than in unlinked simulations. Coverage maps were constructed (FIG. 1) by superimposing the regions covered by each marker on the genetic map of each chromosome. At the end of the Stage II screen, a total of 473 microsatellite markers had been typed with genome coverage (in the combined data set) of over 94%. Possible coverage gaps are indicated by unshaded areas and are mainly concentrated near telomeres. Because the coverage calculations make use of marker informativeness within the pedigrees the coverage approach thus permits detection of instances where markers with expected high heterozygosities are uninformative in our data set.

Pedigree Linkage Analysis Results

Figure 1B:
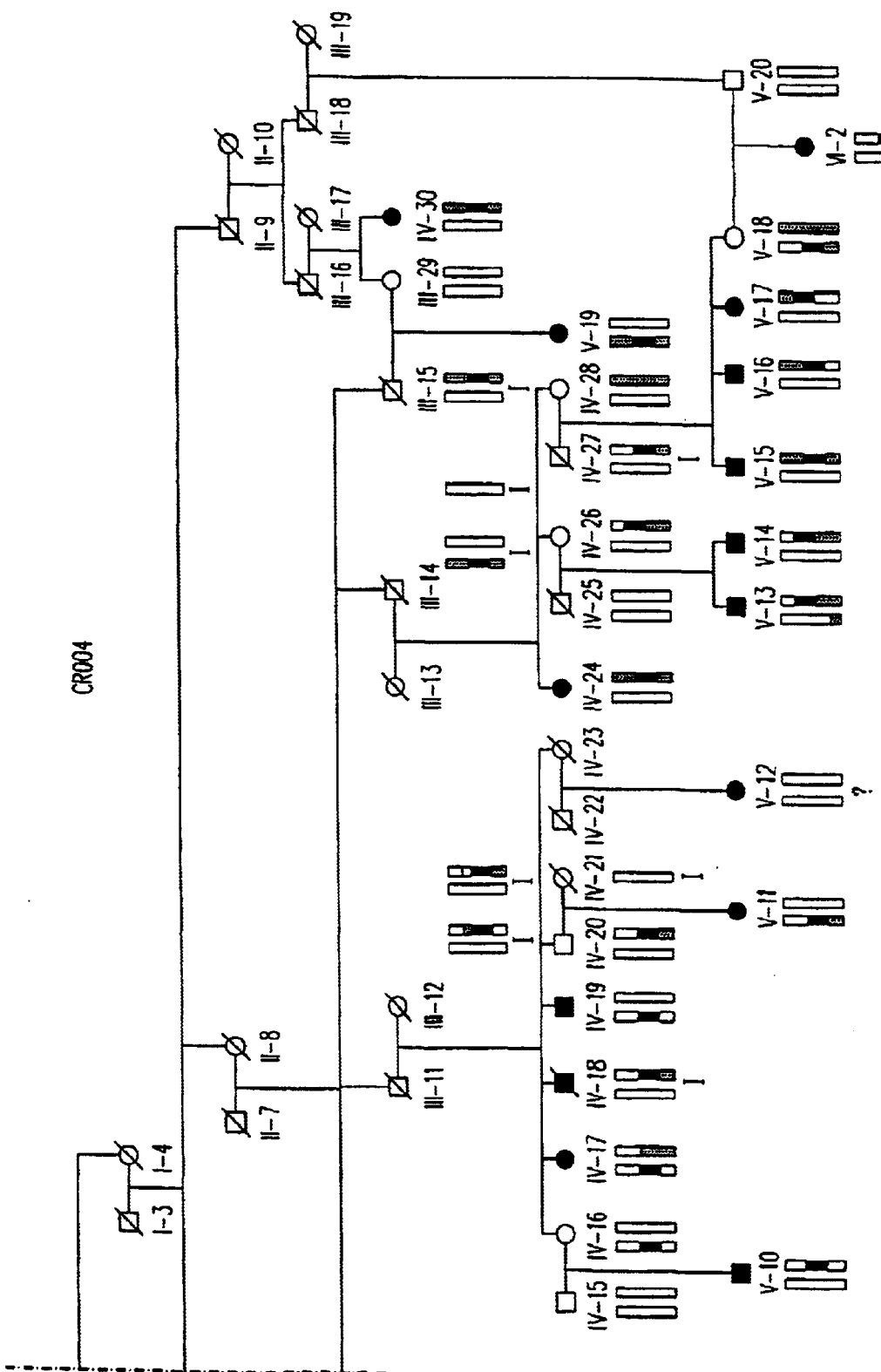
Figure 3:
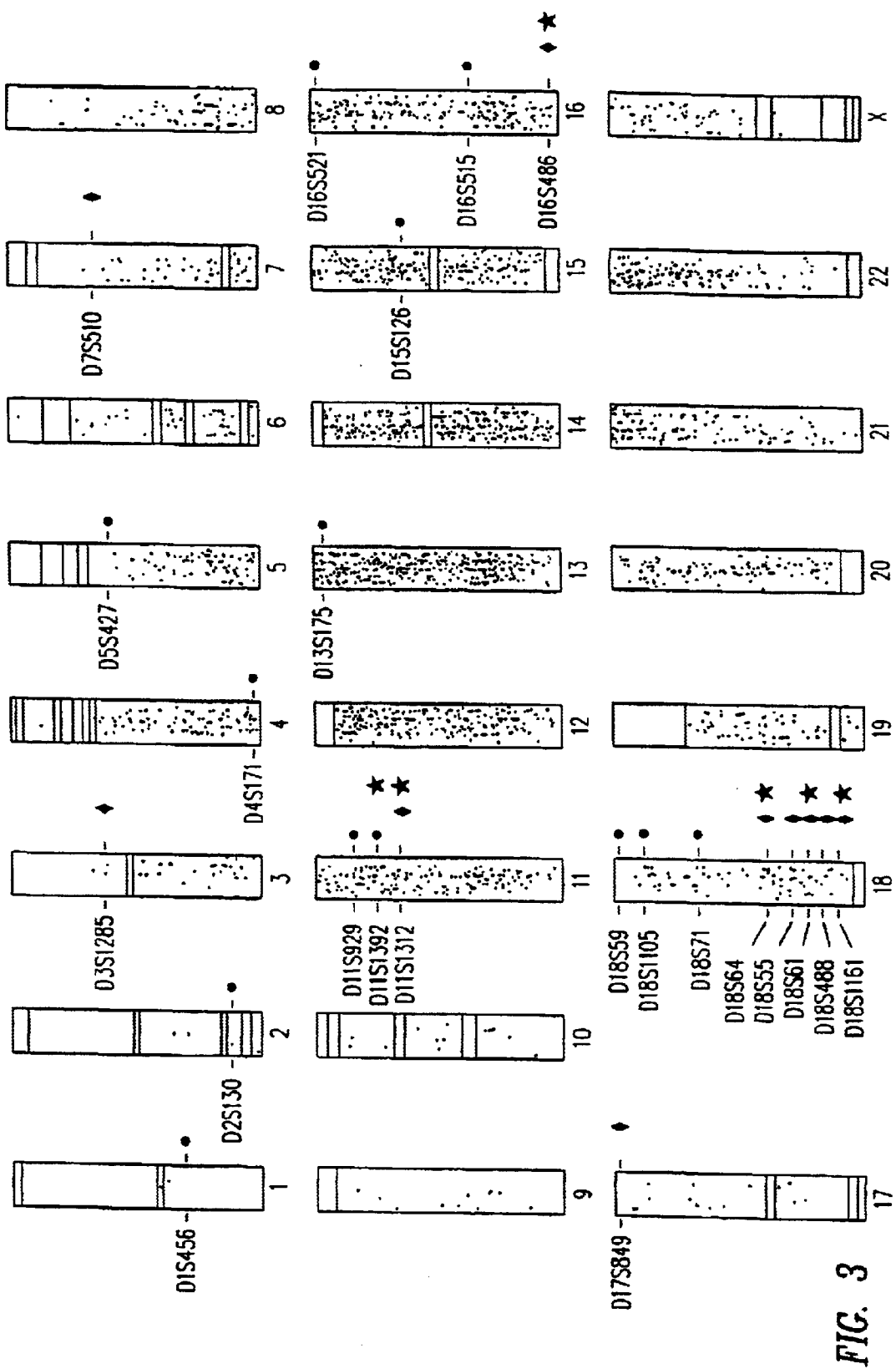
FIG. 3 depicts the extent of marker coverage used in the pedigree genome screening study for each chromosome. Coverage is defined as regions for which a lod score of at least 1.6 would have been detected (in the combined data set) for markers truly linked to BP-I under the model employed. Areas that remain uncovered (at this threshold) are unshaded. Markers for which lod scores were obtained that exceeded the empirically determined coverage thresholds in CR001, CR004, or the combined data set, are shown at their approximate chromosomal location. The symbols to the right of the chromosome indicate the thresholds exceeded at that marker: a circle signifies that the lod score at a marker exceeded the threshold of 0.8 in CR001, a diamond signifies that the lod score exceeded the threshold of 1.2 in CR004, and a star signifies that the lod score exceeded the threshold of 1.6 in the combined data set.
Figure 4A:
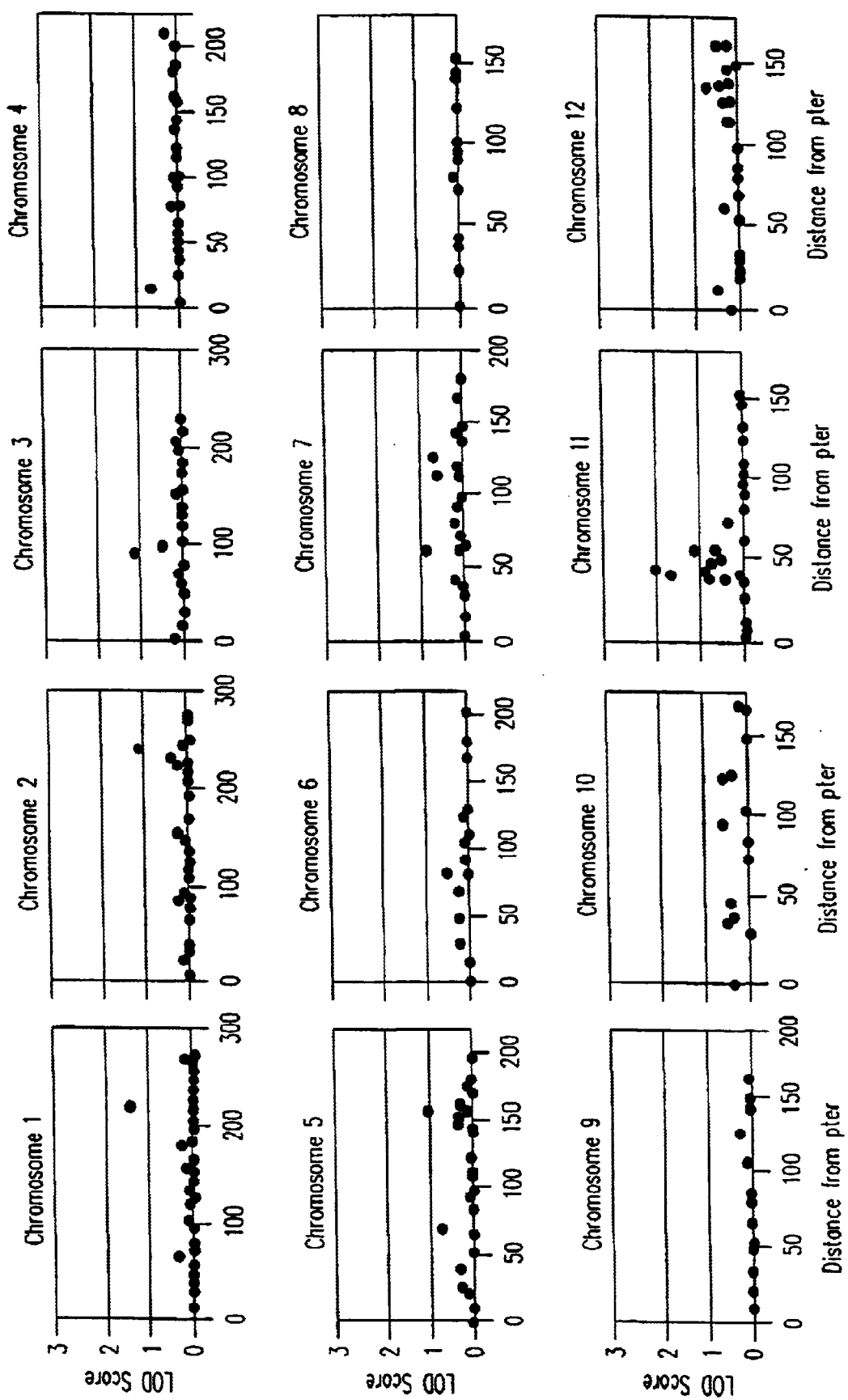
FIGS. 4A and 4B depicts the Lod score for the maximum likelihood estimate of theta in the combined sample for the 473 microsatellite markers typed in the pedigree genome screen. The MLEs of theta were appointed to the following categories: theta<0.10; 0.10≦theta≦0.40; theta≧0.40. Note that the scale for the x-axis (distance from pter) changes with chromosomes.
Figure 4B:
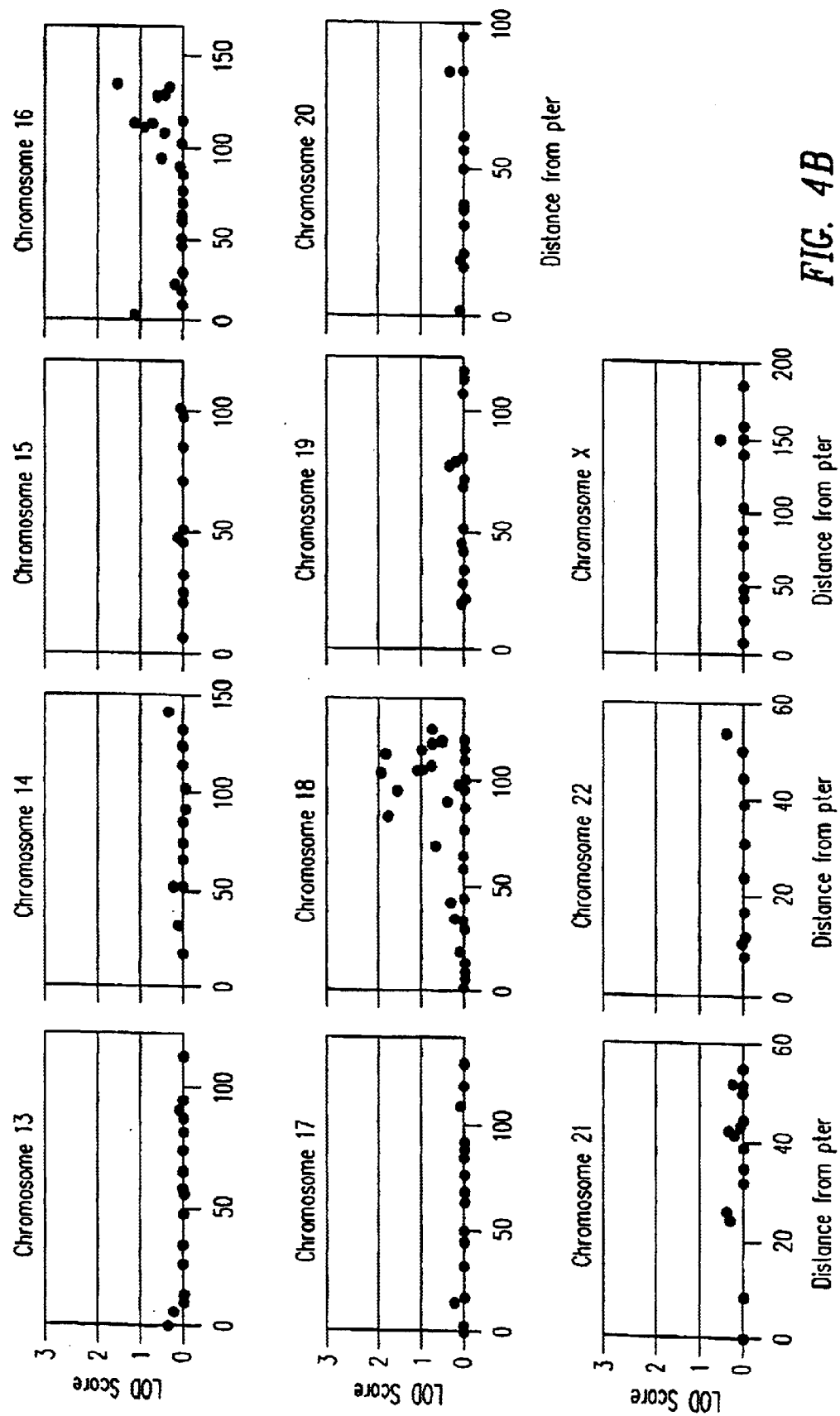
Figure 5:
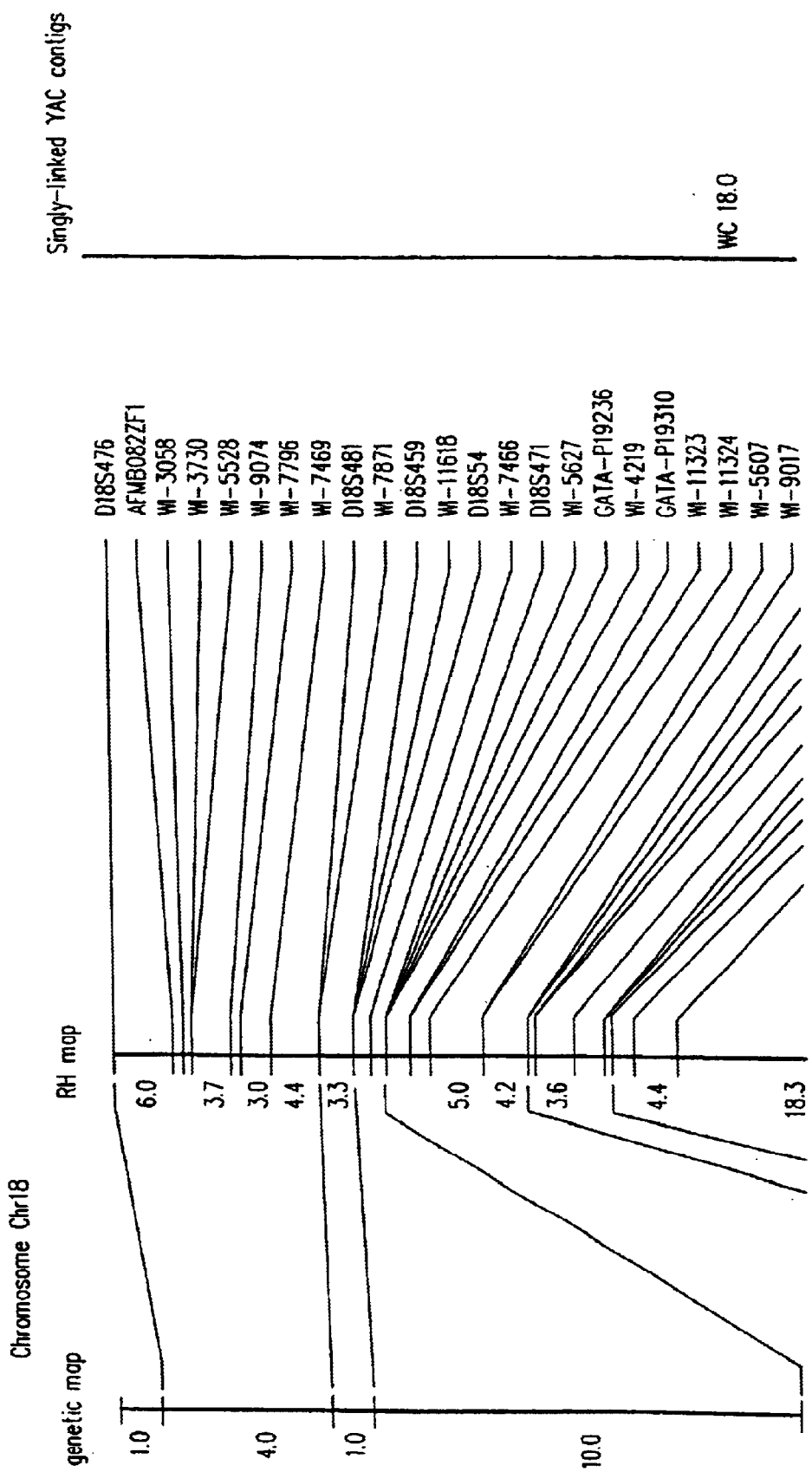
FIG. 5 is a portion of an integrated map of the 5 cM 18pter region of chromosome 18.

Of the 473 microsatellites analyzed with two-point linkage tests, 23 markers exceeded the empirically determined thresholds designated for the coverage calculations (in either CR001, CR004, or in the combined data set). The location of these markers, the peak lod scores obtained in each family and in the combined data set, and the maximum likelihood estimate of the recombination fraction (θ) at which these lod scores were observed are indicated in Table 1. The approximate chromosomal locations of these markers are also depicted in FIG. 1. The distribution of lod scores (for the maximum likelihood estimate of θ in the combined data set) across the genome is displayed by chromosome in FIG. 2.

The threshold was exceeded for pedigree CR001 in two adjacent markers near the 18p telomere (D18S59 and D18S1105), but CR004 displayed no suggestion of linkage in this region.

In the genome screen, the highest lod score observed for family CR001 alone was at D18S59 (1.32 at θ=0.0), located near pter. All affected members of CR001 shared alleles at markers in the 18pter region.

Unrelated BP-I CRCV Patient Study Results

Out of the forty-two markers tested, eight displayed evidence of over-representation of a particular allele on disease chromosomes. Eight of the 42 markers had −2*ln (likelihood ratio) statistics>1.0. Three other markers had −2*ln(likelihood ratio) statistics>0 and <0.62. The results are shown in Table I:

TABLE I

| Marker | Allele Size | Frequency on non-disease Chromosomes | Frequency on Disease Chromosomes |
|---|---|---|---|
| D18S59 | 154 | 0.121 | 0.572 |
| D18S476 | 271 | 0.470 | 0.771 |
| D18S467 | 172 | 0.384 | 0.693 |
| D18S61 | 177 | 0.074 | 0.326 |
| D18S485 | 182 | 0.237 | 0.586 |
| D18S870 | 179 | 0.405 | 0.657 |
| D18S469 | 234 | 0.128 | 0.450 |
| D18S1121 | 168 | 0.171 | 0.553 |

Evidence for association was found at markers located near the telomere of the short arm of chromosome 18. D18S59 displayed the strongest evidence for LD (−2*ln (likelihood ratio) of 8.3, p=0.002) of all the chromosome 18 markers tested. An adjacent marker, D18S476 (−2*ln (likelihood ratio) of 1.3), also provided evidence of LD. In our genome screening pedigree study we observed the single highest lod score for pedigree CR001 of any marker in the entire genome at D18S59. Furthermore, the alleles at D18S59 and D18S476 that are over-represented among the BP-I patients from the population sample (154 b.p. and 271 b.p. respectively) are observed in all BP-I patients from pedigree CR001.

The LD and pedigree findings in the 5 cM 18pter region denote a clearly delineated region that contains a BP-I susceptibility locus. This region is distinct from other regions on chromosome 18 that have been suggested as linked to mood disorder phenotypes (more broadly defined than BP-I). See FIGS. 6A, 6B, 6C. In contrast to previous reports by Berrettini et al. and Stine et al., suggesting possible linkage between mood disorder and markers in the pericentromeric region of chromosome 18, our results did not show any evidence for association of BP-I with any pericentromeric markers (D18S378, D18S53, D18S453 or D18S40).

Identification of New Markers From the 5 cM 18pter Region

Cloned human genomic DNA covering the target region is assembled. Microsatellite sequences from these clones are identified. A sufficient area around the repeat to enable development of a PCR assay for genomic DNA is sequenced, and it is confirmed that the microsatellite sequence is polymorphic, as several uninformative microsatellites are expected in any set. Several methods have been routinely used to identify microsatellites from cloned DNA, and at this time no single one is clearly preferable (Weber, 1990, Hudson et al., 1992). Most of these require screening an excessive number of small insert clones or performing extensive subcloning using clones with larger inserts.

New strategies have recently been developed which permit the use of the several different microsatellites to be found within a single large insert clone without requiring extensive subcloning. A method for direct identification of microsatellites from yeast artificial chromosomes (YACs) provides several new markers from the target region. This procedure is based on a subtractive hybridization step that permits separation of the target DNA from the vector background. This step is useful because the human DNA (the YAC) constitutes only a small proportion of the total yeast genomic DNA.

YAC clones (with inserts averaging about 750 Kb of human genomic DNA) that span the 5 cM 18pter region have already been identified by the CEPH/Geréthon consortium (Cohen et al., 1993) and are publicly available. The markers from YACs that have been mapped to portions of the candidate region that are not well represented by currently available markers are first isolated. By typing these markers in the families and the "LD" sample, as described above, it is possible to narrow the candidate region, perhaps to a size of less than one to two cM, thus permitting limitation of the segment in which more extensive mapping efforts are applied.

Briefly, the microsatellite identification procedure is performed as follows: A subtractive hybridization is performed using genomic DNA from a target YAC together with an equivalent amount of a control DNA. This procedure separates the YAC DNA from that of the yeast vector. Following the subtraction procedure the subtracted YAC DNA is purified, digested with restriction enzymes and cloned into a plasmid vector (Ostrander et al., 1992). The cloned products of each YAC are screened using a CA(15) oligonucleotide probe (i.e. an oligonucleotide having 15 CA repeats). Each positive clone (i.e. those that contain TG-repeats) is sequenced to identify primers for PCR to genotype the BP-I samples.

An alternative approach, based on using a set of degenerate sequencing primers that anneal directly to the repeat sequence, permitting direct thermal cycle sequencing (Browne & Litt, 1992), can also be used.

Once the candidate region is narrowed to a size of less than about 500 to 1000 Kb, a contiguous array (contig) of clones with smaller inserts than YACs, mainly P1 clones, is developed. P1 clones are phage clones specially designed to accommodate inserts of up to 100 Kb (Shepherd et al., 1994).

Development of a Physical Map of the 5 cM 18pter Region

In parallel with the genetic mapping, a physical map of the 5 cM 18pter region is developed. The backbone of this effort is the assembly of contigs of large insert clones. Low resolution contigs for most of the human genome are already available using the YACs developed by CEPH (Cohen et al., 1993). Although these have been individually verified and checked for overlap with other YACs, there is a high rate of chimerism in the YACs and insufficient evidence to definitively confirm the order of the YACS. In addition, because of their large size these YACs are particularly cumbersome to work with. Nevertheless, they provide a useful framework to start constructing high resolution contigs.

Once a candidate region of less than about five cM is delineated, the studies to develop a physical map are commenced. Because of the disadvantages of relying solely on YACs, and because positional cloning is facilitated by the availability of a higher resolution map, contigs are generated using P1 clones once the candidate region is narrowed to less than one Mb, by LD mapping in the expanded population sample using the new markers identified from the YACs.

Once a region of 500–1000 Kb or less is defined, physical mapping and cloning are computed using P1 clones rather than YACS, and P1 contigs over such a region are constructed. The P1s are used to identify additional markers for the further positional cloning steps as well as the screening for rearrangements.

The starting point of contig construction is the microsatellite sequences and non-polymorphic STSs that derive from the few YACs that surround the genetically determined candidate region. These STSs are used to screen the P1 library. The ends of the P1s are cloned using inverse PCR and used to order the P1s relative to each other. Amplification in a new P1 will indicate that it overlaps with the previous one. Fluorescent in situ hybridization (FISH) permits ordering of the majority of the P1s (Pinkel, 1988; Lichter, 1991). The original set of P1s serves as building blocks of the complete contig; each end clone is used to re-screen the library and in this way P1s are added to the map.

From each P1 additional microsatellites are identified as previously described. This allows further reduction of the candidate region. When the region is narrowed to less than one Mb in size, positional cloning efforts are initiated.

Fine Mapping of 5 cM 18pter Region

In order to delineate further regions of BP-I susceptibility within the 5 cM 18pter region, additional unrelated BP-I patients from the CRCV as well as other populations can be diagnosed and genotyped both with the markers described herein as well as additional markers in the 5 cM 18pter region that are known as well those yet to be identified. Additional markers are available from the Cooperative Human Linkage Center (CHLC) public database, from newer Genethon and CHLC maps as they become available (Murray, J. C. et al. (1994) Science 265, 2049–2054, Gyapay, G., et al. (1994) Nature Genet. 7,246–339) and from the public database of the Utah Center for Genome Research (all of which are incorporated by reference herein). The web addresses for Genethon and CHLC are: Genethon (http://www.genethon.fr/genethon_en.html), CHLC (http://gopher.chlc.org/HomePage.html). These databases are all linked, and one of ordinary skill in the art can readily access the information available from these databases.

The markers shown in FIG. 6A, from number 1 to 22 or 23 can be used to genotype the CRCV pedigrees and unrelated BP-I patients described herein as well as other BP-I affected individuals and pedigrees. See FIG. 6A (portion of a chromosome 18 map available from the Whitehead Institute, web address: http://133.30.8.1:8080/=@=:www.genome.wi.mit.edu. (incorporated herein by reference)). The fine mapping techniques described herein in conjunction with the teachings regarding the 5 cM 18pter region can be used to narrow the BP-I susceptibility region further.

The following markers (listed in order of occurrence from the telomere towards the centromere) were used to delineate regions of BP-I susceptibility within the 5 cM 18pter region: SAVA5, ca211, ca212, D18S1140, D18S59, ca231, ta201, AT201, ca225, w3442, ca213, ga201, ga203, ca219, D18S1105, ca209, ca202, D18S1146, GATA (referred to in the figures as 166d05) and D18S476. The markers SAVA5, D18S1140, D18S59, ta201, at201, w3442, ga201, ga203, D18S1105, D18S1146, GATA and D18S476 were used in both the haplotype analysis (FIG. 8) and the AHR analysis (FIG. 11) to delineate the BP-I susceptibility locus to the 500 kb region defined by the markers SAVA5 and ga203 and the 300 kb region defined by D18S1140 and W3422. The other markers were used in both haplotype and the AHR analyses as confirmatory evidence for the localizations. Blood samples from 105 affected individuals were tested for the presence of marker haplotypes and compared to marker haplotypes detected on the non-transmitted chromosome in samples obtained from the parent(s) of the affected individuals when available (71 cases) or to markers detected in samples obtained from a control population of students attending the University of Costa Rica (52 samples). The non-transmitted chromosomes are well matched as controls allowing the affected haplotype of the transmitted chromosome to be more easily discerned than through comparison with data obtained from the general population that may contain individuals who carry the affected haplotype but do not exhibit clinical symptoms of bipolar mood disorder.

FIG. 7 provides 18p allele frequencies for disease (aff 105) versus nontransmitted (ntrans) chromosomes and samples from the control population of students (control). The name of each marker used in this study is indicated on the left. The second column of numbers refers to allele length in basepairs. This data provides evidence of over-representation of a particular allele on disease chromosomes.

FIG. 8 summarizes the results obtained with affected individuals. The column labelled 18p refers to the patient identifier, and each patient identifier is repeated to indicate results with both copies of chromosome 18. The labels "PANR" and "MANR" refer to the paternal and maternal identifier, respectively, associated with the particular patient, other than 0, 1 and 2, which indicate that parental samples were not available. The allele length (base pairs) is indicated under each marker for a particular patient; the length of the horizontal bar in the figure reflects whether haplotypes are IBD or IBS, with IBD haplotypes with common ancestors having longer bars than randomly inherited IBS haplotypes. To the right of each marker, a "1" indicates that the phase is known, i.e., that it is known whether a particular allele is inherited from the paternal or maternal chromosome, and a "0" indicates that the phase is not known for sure. The determination of phase allows the practitioner to conclude that marker alleles are linked in a haplotype on the same disease causing chromosome.

FIG. 9 provides similar data for non-transmitted chromosomes obtained from parental samples. Some individuals exhibited the affected haplotype indicating that the parent was homozygous; however, these regions of identity were typically much shorter than those regions observed in affected individuals, indicating that they were IBS.

FIG. 10 similarly provides data for an unscreened population of students from the University of Costa Rica and their parents (52 samples in total). The data demonstrate that there is a lower incidence of the affected haplotype in the general population as compared with FIG. 8 and that the affected haplotype is typically shorter similar to the results obtained with non-transmitted chromosomes. However, the results for the general population is less distinctive than that observed for non-transmitted chromosomes in allowing one to map the affected haplotype.

Comparison of the affected haplotype with non-transmitted chromosome markers indicate that the region of maximal sharing between affected individuals occurs between 1140t and w3442 on chromosome 18. This region encompasses approximately 300 kb.

The data was analyzed further using Ancestral Haplotype Reconstruction (AHR), a likelihood method for measuring LD. Data from affected individuals are examined in 2-marker segments. Within each segment, the multinomial likelihood of each of the possible ancestral haplotypes giving rise to the observed sample of disease haplotypes is calculated. This likelihood is calculated assuming some fraction, α, of disease chromosomes are associated with this 2-marker segment, and (1−α) are linked to this segment. These haplotype likelihoods are weighted by the probability of observing that haplotype in the population, and summed to create an overall likelihood for the 2-marker segment. This segment likelihood is compared to the null likelihood, which assumes the disease and markers are unlinked (and therefore α=0), and a LOD score is generated. The LOD score is maximized over the parameter α. Details of these calculations are presented in Appendix A. The results of this analysis are shown in FIG. 11. The percentages given above the diagonal line demarcated by the filled boxes indicate the percentage of disease chromosomes hypothesized to be true chromosomes from a common founder. For example, 17% of chromosomes obtained from affected individuals have the 18S59 to W3442 region; i.e., as each individual has two chromosome copies, 34% of individuals have this region. The number above each percentage indicates the LOD score. The numbers given below the diagonal line demarcated by the filled boxes indicate the alleles inherited from a common founder, with the number prior to the dash indicating the allele of the marker identified in the column heading and the number following the dash indicating the allele of the marker identified in the row heading. The marker alleles are referred to as follows:

| MARKER  | #  | ALLELE LENGTH |
|---------|----|---------------|
| SAVA5   | 2  | 229           |
| CA211   | 3  | 195           |
| 18S1140 | 2  | 268           |
| 18S59   | 4  | 154           |
| 18S59   | 6  | 158           |
| TA201   | 2  | 220           |
| TA201   | 3  | 230           |
| CA231   | 2  | 186           |
| CA231   | 4  | 202           |
| AT201   | 1  | 170           |
| AT201   | 2  | 178           |
| CA225   | 1  | 160           |
| CA225   | 3  | 172           |
| W3442   | 1  | 10            |

Blank boxes indicate no positive evidence for linking the indicated region to the affected chromosome.

Use of P1 Clones to Identify Candidate cDNAs for Screening for Mutations in the DNA of BP-I Patients The P1 clones described above are used to identify candidate cDNAs. The candidate cDNAs are subsequently screened for mutations in DNA from BP-I patients. From the minimal candidate region defined by genetic mapping experiments a segment is left that is sufficiently large to contain multiple different genes.

Identification of Coding Sequences

Coding sequences from the surrounding DNA are identified, and these sequences are screened until a probable candidate cDNA is found. Much of the human genome will be sequenced over the next few years, in which case it may become feasible to identify coding sequences through database screening. Candidates may also be identified by scanning databases consisting of partially sequenced cDNAs (Adams et al., 1991), known as expressed sequence tags, or ESTs. These resources are already largely developed, and include upwards of 100,000 cDNAs, the majority expressed primarily in the brain. It is not yet clear, however, that the complete set of cDNAs will be mapped to specific chromosomal locations in the near future, and that their data will soon be made publicly available. The database can be used to identify all cDNAs that map to the minimal candidate region for BP-I. These cDNAs are then used as probes to hybridize to the P1 contig, and new microsatellites are isolated, which are used to genotype the "LD" sample.

Maximal linkage disequilibrium in the vicinity of one or two cDNAs is identified. These cDNAs are the first ones used to screen patient DNA for mutations. Database screening has already been used to identify a gene responsible for familial colon cancer (Papadopolous et al., 1993).

Coding sequences are also identified by exon amplification (Duyk et al., 1990; Buckler et al., 1991). Exon amplification targets exons in genomic DNA by identifying the consensus splice sequences that flank exon-intron boundaries. Briefly, exons are trapped in the process of cloning genomic DNA (e.g. from P1s) into an expression vector (Zhang et al., 1994). These clones are transfected into COS cells, RT-PCR is performed on total or cytoplasmic RNA isolated from the COS cells using primers that are complementary to the splicing vector. Exon amplification is tedious but routine; for example, the system developed by Buckler et al. (1991). This method is probably preferable to another widely used approach, direct selection, which involves screening cDNAs using large insert clone contigs, with several steps to maximize the efficiency of hybridization and recovery of the appropriate hybrid (Lovett et al., 1991). Although direct selection is more efficient than exon amplification (Del Mastro et al., 1994), it may not be practical as it depends on the candidate cDNA being expressed in the tissue from which the cDNA library was made; there is no prior information to indicate the tissue or developmental stage in which BP-I genes would be expressed.

Once cDNAs are identified the most plausible candidates are screened by direct sequencing, SSCP or using chemical cleavage assays (Cotton et al. 1988).

The data are also evaluated for clues to the possible identity or mode of action of BP-I mutations. For example, it is known that trinucleotide repeat expansion is associated with the phenomenon of anticipation, or the tendency for a phenotype to become more severe and display an earlier age of onset in the lower generations of a pedigree (Ballabio, 1993). Several investigators have suggested that segregation patterns of BP-I are consistent with anticipation (McInnis et al., 1993; Nylander et al., 1994). The apparent transmission of BP-I, in association with the conserved 18q23 haplotype is constant with anticipation. Therefore, once the candidate region is narrowed to its minimal extent, the P1 clones are screened using trinucleotide repeat oligonucleotides (Hummerich et al., 1994). A PCR assay is developed and patient DNAs are screened for expanded alleles.

Genetic and physical data help to map the bipolar mood disorder gene to the 5 cM 18pter region of chromosome 18. New markers from this region are tested in order to locate the bipolar mood disorder gene in a region small enough to provide higher quality genetic tests for bipolar mood disorder, and to specifically find the mutated gene. Narrowing down the region in which the gene is located will lead to sequencing of the bipolar mood disorder gene as well as cloning thereof. Further genetic analysis employing, for example, new polymorphisms flanking D18S59 and D18S476 as well as the use of cosmids, yeast artificial chromosome (YAC) clones, or mixtures thereof, are employed in the narrowing down process. The next step in narrowing down the candidate region includes cloning of the chromosomal region 18pter including proximal and distal markers in a contig formed by overlapping cosmids and YACS. Subsequent subcloning in cosmids, plasmids or phages will generate additional probes for more detailed mapping.

The next step of cloning the gene involves exon trapping, screening of cDNA libraries, Northern blots or rt PCR (reverse transcriptase PCR) of samples from affected and unaffected individuals, direct sequencing of exons or testing exons by SSCP (single strand conformation polymorphism), RNase protection or chemical cleavage.

Flanking markers on both sides of the bipolar mood disorder gene combined with D18S59 and D18S476 or a number of well-positioned markers that cover the chromosomal region (5 cM 18pter) carrying the disease gene, can give a high probability of affected or non-affected chromosomes in the range of 80–90% accuracy, depending on the informativeness of the markers used and their distance from the disease gene. Using current markers linked to bipolar mood disorder, and assuming closer flanking markers will be identified, a genetic test for families with bipolar mood disorder will be for diagnosis in conjunction with clinical evaluation, screening of risk and carrier testing in healthy siblings. In the future, subsequent delineation of closely linked markers which may show strong disequilibrium with the disorder, or identification of the defective gene, could allow screening of the entire at-risk population to identify carriers, and provide improved treatments.

Treatment of BP-I Patients Using Genotype Data

Using the fine mapping techniques described herein, BP-I susceptibility loci or genes in the 5 cM 18pter region in particular in the region #1 between SAVA5 and ga203, are identified and used to genotype patients diagnosed phenotypically with BP-I. Preferably, markers in the roughly 500 kb region defined by SAVA5 and ga203, inclusive, are used. More preferably, markers in either the region defined by D18S59 and w3422, inclusive, are used.

Genotyping with the markers described herein as well as additional markers permits confirmation of phenotypic BP-I diagnoses or assist with ambiguous clinical phenotypes which make it difficult to distinguish between BP-I and other possible psychiatric illnesses. A patient's genotype in the 5 cM 18pter region is determined and compared with previously determined genotypes of other individuals previously diagnosed with BP-I. Once an individual is genotyped as having a BP-I susceptibility locus in the 5 cM 18pter region, the individual is treated with any of the known methods effective in treating at least certain individuals affected with BP-I, such as the administration of lithium salts, carbamazepine or valproic acid.

Studies are conducted correlating effective treatments with BP-I genotypes in the 5 cM 18pter region to determine the most effective treatments for particular genotypes. BP-I patients can then be genotyped in the 5 cM 18pter region and the statistically most effective treatment can be determined as a first course of therapy.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

Appendix A

Consider the original mutation to have occurred on a chromosomal segment between two markers A and B. At the time the mutation was introduced, there were $n_a$ alleles at marker A and $n_b$ alleles at marker B. On the chromosome containing the disease mutation both marker A and marker B carried allele X. The probability that after g generations an affected individual carrying the original disease mutation would still have allele X at markers A and B is:

$(1-\theta_1)^g(1-\theta_2)^g$ $+(1-\theta_1)^g(1-$ $(1-\theta_2)^g)f(X_B)+(1$ $-(1-\theta_1)^g)(1-\theta_2)^g f$ $(X_A)+(1-(1-\theta_1)^g)(1$ $-(1-\theta_2)^g)f(X_A)f$ $(X_B)$ eq (1)

where $\theta_1$ is the recombination fraction between disease and marker A, $\theta_2$ is the re-combination fraction between disease and marker B, g is the number of generations since founding (i.e. since the mutation was introduced into the population), $f(X_A)$ is the population frequency of the X-allele at marker A and $f(X_B)$ is the population frequency of the X-allele at marker B. This equation includes terms for the possibility of recombination between the markers and the disease locus, with the X-allele at the markers then being identical by state (IBS) rather than IBD. The probabilities of an affected individual with the original mutation having other haplotypes can be formulated similarly. The probability of having allele Z at marker B (where Z is any allele at marker B besides X) would be:

$(1-\theta_1)^g(1-(1-\theta_2)^g)f(Z_B)+(1-(1-\theta_1)^g)(1-(1-\theta_2)^g)f(X_A)f(Z_B)$ eq (2)

where $f(Z_B)$ is the frequency of allele Z at marker B in the population. The probability of having allele Z at marker A (where Z is any allele at marker B besides X) would be:

$(1-\theta_2)^g(1-(1-\theta_1)^g)f(Z_A)+(1-(1-\theta_1)^g)(1-(1-\theta_2)^g)f(X_B)f(Z_A)$ eq (3)

where $f(Z_A)$ is the frequency of allele Z at marker A in the population. Finally, the probability of having allele Z at both markers A and B would be:

$(1-(1-\theta_1)^g)(1-(1-\theta_2)^g)f(Z_A)f(Z_B)$ eq (4)

These probabilities assume (1) no interference in recombination and (2) the same marker alleles are present now as were present g generations ago, in similar frequencies. If, for example, marker A has $n_a$ alleles and marker B has $n_b$ alleles, then these probabilities form a $(n_a)\cdot(n_b)$ by $(n_a)\cdot(n_b)$ transition matrix, with row i containing the probabilities that founder haplotype i gave rise to each of the $(n_a)\cdot(n_b)$ different haplotypes in g generations. The rows of this transition matrix sum to 1.

In simulations, the haplotype frequencies in the disease population were formulated using these transition probabilities, assuming the disease arose on a haplotype with the "1" allele at each of the two markers.

Once these transition probabilities are estimated, the likelihood of a particular founder chromosome giving rise to the observed sample of disease haplotypes in g generations is easily estimated. For example, if one assumed that the disease mutation arose on a chromosome with the X-allele at both markers, the likelihood ($L_{X-X}$) that this chromosome was the founder of the present-day sampled disease chromosomes is given by the multinomial:

$$L_{X-X} = \prod_{i=1}^{K}(P_{X-X,i})^{Y_i}$$ eq (5)

where i indexes the K potential haplotypes for the two markers ($K=(n_a)(n_b)$), $p_{x-x,i}$ is the probability that the ancestral disease chromosome with the X-allele at both markers gave rise to a haplotype of type i in g generations (taken from the transition matrix), and $Y_i$ is the observed number of haplotype i in the sample ($\Sigma_i(Y_i)$=the number of chromosomes in the sample to be analyzed). The likelihood in eq (5) assumes that all affected individuals are independent. While, after many generations of separation from a common ancestor one might consider these individuals to be independent, they are in fact related through a complex and unknown pedigree. The simplification of considering individuals as independent makes the likelihood much more tractable to compute.

The K likelihoods are then summed, and weighted by the probability of observing that particular haplotype in the population to produce an overall likelihood for the 2-marker segment:

$$L = \sum_{i=1}^{K} f_i L_i.$$ eq (6)

where $f_i$ is the frequency of haplotype i in the population. This overall likelihood calculation parallels the approach taken by Terwilliger (1995, eq (2)). The haplotype frequencies are estimated from the sample of normal chromosomes. In the event that the haplotype resulting in the largest contribution to the overall likelihood in eq (6) is not observed in the normal sample, the upper 95% confidence interval for this frequency is used, and the remaining haplotype frequencies resealed accordingly.

This overall likelihood is compared to the null likelihood, which is generated in exactly the same manner, except that it is assumed the markers were unlinked to the disease locus ($\theta_1=\theta_2=0.5$ in, for example, eqs (1–4)). The $\log_{10}$ of this likelihood ratio is a LOD score. One might consider to use in the null likelihood transition probabilities calculated under the assumption of linkage equilibrium. Under this null the cells of the transition matrix are computed by multiplication of allele frequencies, assuming independence of marker loci. These two forms of the null likelihood are equivalent in value for g of approximately 20 or greater, and for g<20 the values are nearly equivalent.

Because $\theta_1$ and $\theta_2$ are obviously unknown, the putative disease locus is set to be in the middle of the segment and therefore $\theta_1$ and $\theta_2$ are one-half the genetic distance (converted to recombination fraction by the Haldane mapping function, (Ott 1991)) between the two marker loci forming the segment. In fact one could estimate $\theta_1$ and $\theta_2$, or their ratio, and the method could easily be modified to do so, however for our purposes finding a linked segment is suitable.

This basic procedure has been modified to deal with heterogeneity in the sample of disease chromosomes. Not all chromosomes in the disease sample may be true disease chromosomes from a common founder. Individuals heterozygous for the disease mutation will add one chromosome to the disease sample that will not be a true disease chromosome. Additionally, affected individuals not linked to the particular chromosomal segment being analyzed (either because they are phenocopies or because of locus heterogeneity) will contribute two chromosomes to the affected sample that do not harbor this disease locus. When the null hypothesis of no linkage is not true, some fraction, α, of the chromosomes in the disease sample will associated with this chromosomal segment, and (1−α) will not be associated. We decided to examine α in steps of 0.1, from 1.0 to 0.0, and for each step in α produce a new transition matrix under the alternative hypothesis and calculate a LOD score. If we call the transition matrix calculated under the alternative hypothesis (where the disease locus is hypothesized to be in the middle of the 2-marker segment) $T_a$ and call the transition matrix calculated under the null hypothesis (where the disease locus is unlinked to the 2-marker segment) $T_n$, then a new transition matrix for the alternative hypothesis is calculated as:

$$T^*_a = \alpha T_a + (1-\alpha) T_n \qquad \text{eq (7)}$$

The transition matrix under the null uses α=0. The LOD score is then maximized over the one parameter α.

What is claimed is:

1. A method of detecting an increased susceptibility to bipolar mood disorder (BP) in an individual comprising:
a) analyzing a sample of DNA from a test individual for the presence of a DNA polymorphism associated with BP on the short arm of chromosome 18 between SAVA5 and ga203 b) performing a pedigree analysis by analyzing DNA samples obtained from family members of the test individual for the presence of the DNA polymorphism and correlating the presence or absence of the DNA polymorphism with a phenotypic diagnosis of bipolar mood disorder for said individual, wherein a correlation indicates that the test individual has an increased susceptibility to develop BP.

2. The method of claim 1, wherein said DNA polymorphism is located on the short arm of chromosome 18 between and inclusive of D18S1140 and ga203.

3. The method of claim 1, wherein said DNA polymorphism is located on the short arm of chromosome 18 between and inclusive of SAVA5 and W3422.

4. The method of claim 1, wherein said DNA polymorphism is located on the short arm of chromosome 18 between and inclusive of D18S11 and W3422.

5. The method of claim 1, wherein said DNA polymorphism is located on the short arm of chromosome 18 between and inclusive of D18S1140 and at201.

6. The method of claim 1, wherein said DNA polymorphism is located on the short arm of chromosome 18 between and inclusive of D18S1140 and ta201.

7. The method of claim 1, wherein said DNA polymorphism is located on the short arm of chromosome 18 between and inclusive of D18S59 and ta201.

8. The method of claim 1, wherein the polymorphism is a polymorphic microsatellite marker.

9. The method of claim 8, wherein the polymorphism is a single nucleotide polymorphism.

10. A method of detecting an increased susceptibility to bipolar mood disorder (BP) in an individual comprising:
analyzing a DNA sample from said individual for the presence of a polymorphic microsatellite marker, wherein the marker is a 154 base pair allele at D18S59, and wherein the presence of the marker is indicative of an increased susceptibility to BP.

11. A method of detecting an increased susceptibility to bipolar mood disorder (BP) in an individual comprising
analyzing a DNA sample from said individual for the presence of a polymorphic microsatellite marker, wherein the marker a 271 base pair allele at D18S476, and wherein the presence of the marker is indicative of an increased susceptibility to BP.

* * * * *